(12) United States Patent
Chan et al.

(10) Patent No.: US 9,546,131 B2
(45) Date of Patent: Jan. 17, 2017

(54) SUBSTITUTED BIARYL ALKYL AMIDES

(71) Applicant: BioTheryX, Inc., Chappaqua, NY (US)

(72) Inventors: Kyle W. H. Chan, San Diego, CA (US); Frank Mercurio, Rancho Sante Fe, CA (US); David I. Stirling, Basking Ridge, NJ (US)

(73) Assignee: BIOTHERYX, INC., Chappaqua, NY (US)

( * ) Notice: Subject to any disclaimer, the term of this patent is extended or adjusted under 35 U.S.C. 154(b) by 79 days.

(21) Appl. No.: 14/447,473

(22) Filed: Jul. 30, 2014

(65) Prior Publication Data

US 2014/0336235 A1 Nov. 13, 2014

Related U.S. Application Data

(62) Division of application No. 13/653,115, filed on Oct. 16, 2012, now Pat. No. 8,822,527.

(60) Provisional application No. 61/548,076, filed on Oct. 17, 2011.

(51) Int. Cl.
| | |
|---|---|
| *C07C 235/78* | (2006.01) |
| *C07C 229/34* | (2006.01) |
| *C07D 307/24* | (2006.01) |
| *C07D 207/16* | (2006.01) |
| *C07C 233/63* | (2006.01) |
| *C07C 235/12* | (2006.01) |
| *C07C 237/12* | (2006.01) |
| *C07C 233/47* | (2006.01) |
| *C07C 235/20* | (2006.01) |
| *C07C 271/22* | (2006.01) |

(52) U.S. Cl.
CPC .......... *C07C 235/78* (2013.01); *C07C 229/34* (2013.01); *C07C 233/47* (2013.01); *C07C 233/63* (2013.01); *C07C 235/12* (2013.01); *C07C 235/20* (2013.01); *C07C 237/12* (2013.01); *C07C 271/22* (2013.01); *C07D 207/16* (2013.01); *C07D 307/24* (2013.01); *C07B 2200/07* (2013.01)

(58) Field of Classification Search
None
See application file for complete search history.

(56) References Cited

U.S. PATENT DOCUMENTS

| | | | |
|---|---|---|---|
| 6,239,134 | B1 | 5/2001 | Sabb et al. |
| 7,109,243 | B2 | 9/2006 | Liu et al. |
| 2005/0032787 | A1 | 2/2005 | Giannessi et al. |
| 2005/0049310 | A1 | 3/2005 | Mjalli et al. |
| 2005/0059705 | A1 | 3/2005 | Mjalli et al. |
| 2005/0059713 | A1 | 3/2005 | Mjalli et al. |
| 2006/0128748 | A1 | 6/2006 | Mjalli et al. |
| 2007/0004725 | A1 | 1/2007 | Dey et al. |
| 2007/0043035 | A1 | 2/2007 | Gurram et al. |
| 2007/0149525 | A1 | 6/2007 | Hom et al. |
| 2007/0197481 | A1 | 8/2007 | Qian et al. |
| 2008/0175795 | A1 | 7/2008 | Neogi et al. |
| 2009/0011475 | A1 | 1/2009 | Sugi et al. |
| 2009/0111832 | A1 | 4/2009 | Barrow et al. |
| 2010/0022767 | A1 | 1/2010 | Kaiser et al. |
| 2010/0197668 | A1 | 8/2010 | Baudoin et al. |
| 2010/0305131 | A1 | 12/2010 | Coppola et al. |
| 2011/0039851 | A1 | 2/2011 | Dey et al. |
| 2011/0160198 | A1 | 6/2011 | Mjalli et al. |
| 2013/0102649 | A1 | 4/2013 | Chan et al. |

FOREIGN PATENT DOCUMENTS

| | | |
|---|---|---|
| CN | 101555211 | 10/2009 |
| JP | 10101655 | 4/1998 |
| JP | 10101656 | 4/1998 |
| JP | 2007-501844 | 2/2007 |
| JP | 2007-537163 | 12/2007 |
| JP | 2011-529500 | 12/2011 |
| JP | 2014-503534 | 2/2014 |
| WO | WO 99/12896 | 3/1999 |
| WO | WO 00/51999 | 9/2000 |
| WO | WO 2004/084842 | 10/2004 |
| WO | WO 2005/014533 | 2/2005 |
| WO | WO 2005/107762 | 11/2005 |
| WO | WO 2006/015279 | 2/2006 |
| WO | WO 2008/138561 | 11/2008 |
| WO | WO 2010/014554 | 2/2010 |
| WO | WO 2011/048091 | 4/2011 |
| WO | WO 2012/082853 | 6/2012 |

OTHER PUBLICATIONS

Abushanab, et al., "The Chemistry of L-Ascorbic and D-Isoascorbic Acids. 1. The Preparation of Chiral Butanetriols and -tetrols," J. Org. Chem. (1988) 53, 2598-2602.
Adams, "Proteasome inhibitors as new anticancer drugs," Current Opinion in Oncology, 2002, 14(6): 628-634.
Adams, et al., "Proteasome inhibitors: A novel class of potent and effective antitumor agents," Cancer Research, 1999, 59(11): 2615-2622.
Biochemistry (1972) 11(5):942-944.
Ceccarelli et al., "An allosteric inhibitor of the human Cdc34 ubiquitin-conjugating enzyme," Cell (2011) 145(7):1075-1087.
Chalker, et al., "A Convenient Catalyst for Aqueous and Protein Suzuki-Miyaura Cross-Coupling," J. Am. Chem. Soc. (2009) 131:16346-16347.
Chandrasekhar, et al., "Synthesis of protected (2R,3R,4S)-4,7-diamino-2,3-dihydroxyheptanoic acid, a constituent of callipeltins A and D," Tetrahedron Letters (2006) 47:7307-7309.
Chen, et al., "Nickel-Catalyzed Cross-Coupling of Aryl Phosphates with Arylboronic Acids," J. Org. Chem. (2011) 76:2338-2344.
Dick, et al., "Building on bortezomib: second-generation proteasome inhibitors as anti-cancer therapy," Drug Discovery Today, 2010, 15(5-6): 243-249.
Ermolenko, et al., "Diastereoselective Synthesis of All Eight L-Hexoses from L-Ascorbic Acid," J. Org. Chem. (2005) 71:693-703.

(Continued)

*Primary Examiner* — Kamal Saeed
(74) *Attorney, Agent, or Firm* — Knobbe Martens Olson & Bear LLP

(57) ABSTRACT

Disclosed herein are substituted biaryl alkyl amide compounds, methods of synthesizing substituted biaryl alkyl amide compounds and methods of treating diseases and/or conditions with substituted biaryl alkyl amide compounds.

27 Claims, 3 Drawing Sheets

(56) References Cited

OTHER PUBLICATIONS

Fingl et al., General Principles, The Pharmacological Basis of Therapeutics, (5th Ed., 1975) Ch.1, p. 1-46, (Goodman et al. ed, Macmillan Publishing Co.).

Kisselev, et al., "Proteasome inhibitors: from research tools to drug candidates," Chemistry and Biology, 2001, 8(8): 739-758.

Kotkar, et al., "Organocatalytic Sequential α-Amination-Horner-Wadsworth-Emmons Olefination of Aldehydes: Enantioselective Synthesis of γ-Amino-α, β-Unsaturated Esters," Organic Letters (2007) 9(6):1001-1004.

Kotz, "Celgene skips SKP2," SicBX, 2011, 4(28).

Legesse-Miller, et al., "Let-7 Overexpression Leads to an Increased Fraction of Cells in $G_2$/M, Direct Down-regulation of Cdc34, and Stabilization of Wee1 Kinase in Primary Fibroblasts," Journal of Biological Chemistry (2009) 284(11):6605-6609.

Myung, et al., "The Ubiquitin-Proteasome Pathway and Proteasome Inhibitors," Medicinal Research Reviews, 2001, 21(4): 245-273.

Orlowski, et al., "Proteasome Inhibitors in Cancer Therapy: Lessons from the First Decade," Clinical Cancer Research, 2008, 14(6): 1649-1657.

Pan, et al., "Diastereoselective Aldol Reaction of N, N-Dibenzyl-a-amino Aldehydes with Ketones Catalyzed by Proline,"Organic Letters (2004) 6(6):1009-1012.

Wei, et al., "Cdc34-mediated Degration of ATF5 is Blocked by Cisplatin," Journal of Biological Chemistry (2008) 283(27):18773-18781.

Yoo, et al., "Intramolecular Nucleophilic Epoxidation of γ-Amino-α,β-Unsaturated Esters with an N-Hydroperoxymethyl Group," Synlett., (2005) 11:1707-1710.

International Search Report and Written Opinion dated Feb. 4, 2013 in PCT/US2012/060464, filed Oct. 16, 2012.

Amendment and Response to Office Action dated Apr. 10, 2014 in U.S. Appl. No. 13/653,115, filed Oct. 16, 2012.

Notice of Allowance and Fee(s) Due dated Apr. 25, 2014 in U.S. Appl. No. 13/653,115, filed Oct. 16, 2012.

SUBSTITUTED BIARYL ALKYL AMIDES

CROSS-REFERENCE TO RELATED APPLICATIONS

The present application is a divisional of U.S. application Ser. No. 13/653,115, filed Oct. 16, 2012, which claims the benefit of priority to U.S. Provisional Appl. No. 61/548,076, filed Oct. 17, 2011, each of which is hereby incorporated herein by reference in its entirety.

FIELD

The present application relates to the fields of chemistry, biochemistry and medicine. More particularly, disclosed herein are substituted biaryl alkyl amide compounds, pharmaceutical compositions that include one or more substituted biaryl alkyl amide compounds and methods of synthesizing the same. Also disclosed herein are methods of treating diseases and/or conditions with substituted biaryl alkyl amide compounds.

BACKGROUND

The ubiquitin-proteasome system (UPS) plays an important role in many cellular processes. The UPS affects the stability, interactions, and localization of many biological proteins. The UPS can be perturbed in many diseases, such as neoplastic diseases, age-related diseases, neurological diseases, immunological diseases, and infectious diseases. Accordingly, a need exists to develop compounds and compositions that effectively modulate the UPS.

SUMMARY

Some embodiments disclosed herein relate to a compound of Formula (I) or a pharmaceutically acceptable salt thereof. Some embodiments disclosed herein relate to a pharmaceutical composition that includes one or more compounds of Formula (I).

Some embodiments disclosed herein relate to a compound of Formula (I) that has the structure of Formula (II), or a pharmaceutically acceptable salt thereof. Some embodiments disclosed herein relate to a compound of Formula (I) that has the structure of Formula (III), or a pharmaceutically acceptable salt thereof. Some embodiments disclosed herein relate to a compound of Formula (I) that has the structure of Formula (IV), or a pharmaceutically acceptable salt thereof. Some embodiments disclosed herein relate to a compound of Formula (I) that has the structure of Formula (V), or a pharmaceutically acceptable salt thereof. Some embodiments disclosed herein relate to a compound of Formula (I) that has the structure of Formula (VI), or a pharmaceutically acceptable salt thereof. Some embodiments disclosed herein relate to a pharmaceutical composition that includes one or more compounds of Formula (I) that have the structure of Formula (II), (III), (IV), (V), and/or (VI).

Some embodiments disclosed herein relate to a compound of Formula (Ia), (Ib), (Ic) or (Id), or a pharmaceutically acceptable salt thereof, or a pharmaceutical composition that includes one or more compounds of Formula (Ia), (Ib), (Ic) or (Id).

Some embodiments disclosed herein relate to methods for inhibiting the ubiquitin-proteasome system in a subject that can include administering to a subject a compound of Formula (I), (Ia), (Ib), (Ic), (Id), (II), (III), (IV), (V), and/or (VI), or a pharmaceutically acceptable salt thereof, or a pharmaceutical composition that includes one or more compounds of Formula (I), (Ia), (Ib), (Ic), (Id), (II), (III), (IV), (V), and/or (VI) in a therapeutically effective amount sufficient to inhibit the ubiquitin-proteasome system in the subject. In some embodiments, the subject can be a human.

Some embodiments disclosed herein relate to methods for inhibiting Cdc34 in a subject that can include administering to a subject a compound of Formula (I), (Ia), (Ib), (Ic), (Id), (II), (III), (IV), (V), and/or (VI), or a pharmaceutically acceptable salt thereof, or a pharmaceutical composition that includes one or more compounds of Formula (I), (Ia), (Ib), (Ic), (Id), (II), (III), (IV), (V), and/or (VI) in a therapeutically effective amount sufficient to inhibit Cdc34 in the subject. In some embodiments, the subject can be a human. In some embodiments, the Cdc34 can be hCdc34.

Some embodiments disclosed herein relate to methods for inhibiting cellular proliferation in a subject comprising administering to the subject a compound of Formula (I), (Ia), (Ib), (Ic), (Id), (II), (III), (IV), (V), and/or (VI), or a pharmaceutically acceptable salt thereof, or a pharmaceutical composition that includes one or more compounds of Formula (I), (Ia), (Ib), (Ic), (Id), (II), (III), (IV), (V), and/or (VI) in a therapeutically effective amount sufficient to inhibit cellular proliferation in said subject. In some embodiments, the subject can be a human.

Some embodiments disclosed herein relate to methods for ameliorating a condition selected from among a neoplastic disease, a neurological disease, an immunological disease, and an infectious disease that can include administering to a subject suffering from the condition a therapeutically effective amount of a compound of Formula (I), (Ia), (Ib), (Ic), (Id), (II), (III), (IV), (V), and/or (VI), or a pharmaceutically acceptable salt thereof, or a pharmaceutical composition that includes one or more compounds of Formula (I), (Ia), (Ib), (Ic), (Id), (II), (III), (IV), (V), and/or (VI). In some embodiments, the neoplastic disease can be cancer. In some embodiments, the subject can be a human.

Some embodiments disclosed herein relate to methods for identifying a candidate therapeutic compound that can include determining the effective amount of a compound of Formula (I), (Ia), (Ib), (Ic), (Id), (II), (III), (IV), (V), and/or (VI), or a pharmaceutically acceptable salt thereof, on the extent of ubiquitination of p27$^{Kip1}$ by an SCF$^{Skp2}$ E3 complex, such that the compound is identified as a candidate therapeutic compound if the compound significantly reduces the extent of ubiquitination.

Some embodiments disclosed herein relate to methods for determining the effect of a candidate therapeutic compound that can include determining the effective amount of a compound of Formula (I), (Ia), (Ib), (Ic), (Id), (II), (III), (IV), (V), and/or (VI), or a pharmaceutically acceptable salt thereof, on the extent of ubiquitin chain initiation or ubiquitin chain length, such that the compound is identified as a candidate therapeutic compound if the compound significantly reduces said extent of ubiquitin chain initiation or ubiquitin chain length.

DETAILED DESCRIPTION OF THE PREFERRED EMBODIMENTS

Definitions

Figure 1:
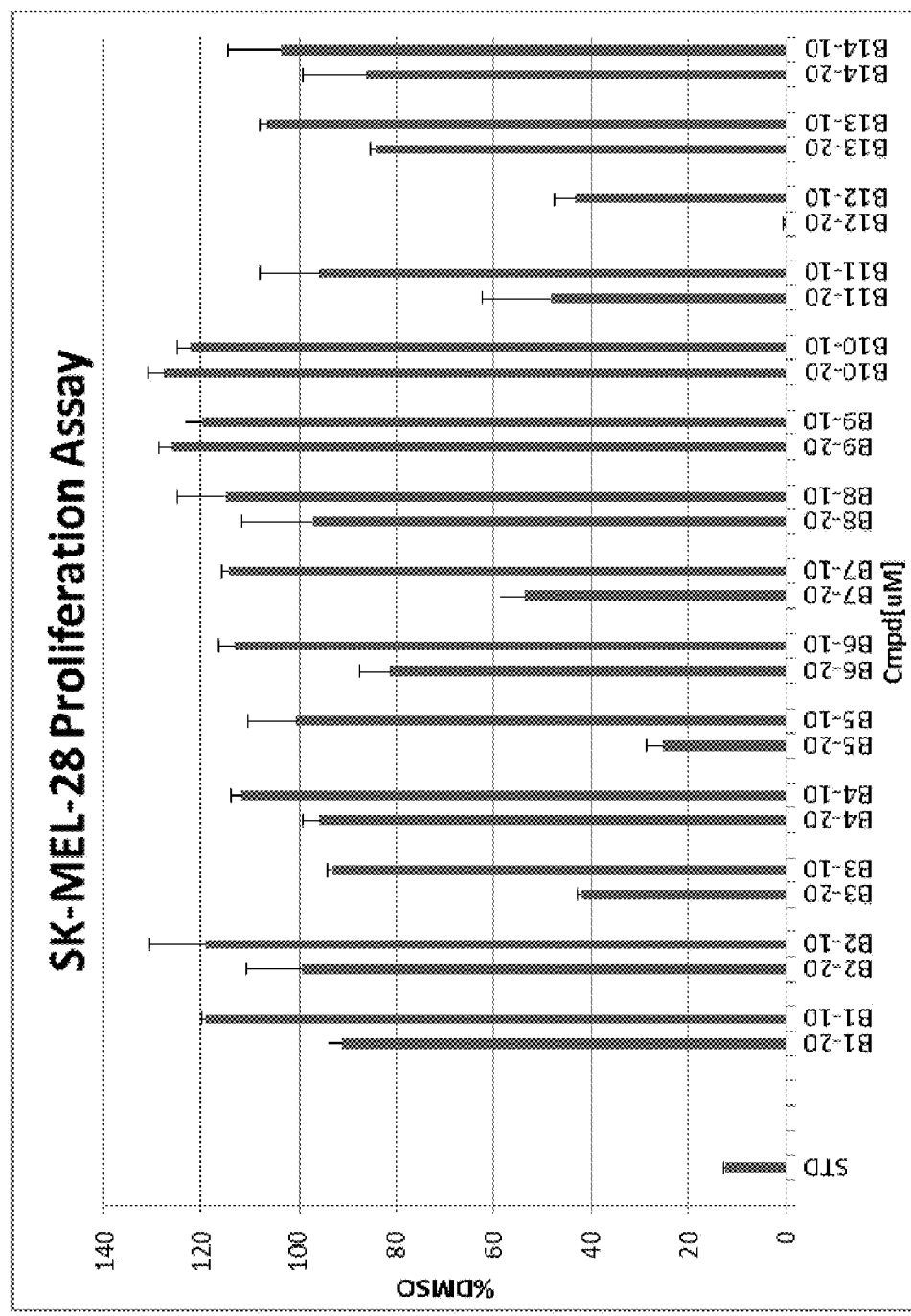
FIG. 1 illustrates the proliferation assay results in the SK-MEL-28 (metastatic melanoma) cell line. Compounds B1 through B14 were tested in 20 μM and 10 μM concentration respectively.

As used herein, common organic abbreviations are defined as follows:
Ac Acetyl
Ac$_2$O Acetic anhydride
aq. Aqueous
Bn Benzyl
Bz Benzoyl
BOC or Boc tert-Butoxycarbonyl
Bu n-Butyl
cat. Catalytic
Cbz Carbobenzyloxy
CDI 1,1'-carbonyldiimidazole
° C. Temperature in degrees Centigrade
DBU 1,8-Diazabicyclo[5.4.0]undec-7-ene
DCE 1,2-Dichloroethane
DCM Methylene chloride
DIEA Diisopropylethylamine
(DHQ)$_2$PHAL Hydroquinine 1,4-phthalazinediyl diether
DMA Dimethylacetamide
DME Dimethoxyethane
DMF N,N'-Dimethylformamide
DMSO Dimethylsulfoxide
DPPA Diphenylphosphoryl azide
ee % Enantiomeric excess
Et Ethyl
EtOAc or EA Ethyl acetate
g Gram(s)
h or hr Hour(s)
HATU 2-(1H-7-azabenzotriazol-1-yl)-1,1,3,3-tetramethyl uronium hexafluorophosphate
HOBT N-Hydroxybenzotriazole
iPr Isopropyl
LCMS Liquid chromatography-mass spectrometry
LDA Lithium diisopropylamide
LiHMDS Lithium bis(trimethylsilyl)amide
m or min Minute(s)
mCPBA meta-Chloroperoxybenzoic Acid
MeOH Methanol
MeCN Acetonitrile
mL Milliliter(s)
MTBE Methyl tertiary-butyl ether
NH$_4$OAc Ammonium acetate
NMO N-Methylmorpholine-N-Oxide
PE Petroleum ether
PG Protecting group
Pd/C Palladium on activated carbon
Pd(dppf)Cl$_2$ 1,1'-Bis(diphenylphosphino)ferrocene-palladium(II)dichloride
Ph Phenyl
ppt Precipitate
PMBC 4-Methoxybenzyl chloride
RCM Ring closing metathesis
rt Room temperature
sBuLi sec-Butyllithium
SFC Supercritical fluid chromatography
TBAF Tetrabutylammonium fluoride
TEA Triethylamine
TCDI 1,1'-Thiocarbonyl diimidazole
TEMPO 2,2,6,6-Tetramethylpiperidin-1-yl)oxyl
Tert, t tertiary
TFA Trifluoroacetic acid
TFAA Trifluoroacetic acid anhydride
THF Tetrahydrofuran
TLC Thin-layer chromatography
TMEDA Tetramethylethylenediamine
TMSNCO trimethylsilyl isocyanate
μL Microliter(s)

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. In addition, the term "comprising" is to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

As used herein, any "R" group(s) such as, without limitation, R, $R^1$, $R^2$, $R^3$, $R^4$, $R^5$, $R^6$, $R^7$, $R^8$, and $R^9$ represent substituents that can be attached to the indicated atom. An R group may be substituted or unsubstituted. If two "R" groups are described as being "taken together" the R groups and the atoms they are attached to can form a cycloalkyl, aryl, heteroaryl or heterocyclyl. For example, without limitation, if $R^{1a}$ and $R^{1b}$ of an $NR^{1a}R^{1b}$ group are indicated to be "taken together," it means that they are covalently bonded to one another to form a ring:

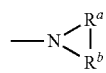

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl or aryl group, or the total number of carbon atoms and heteroatoms in a heteroalkyl, heterocyclyl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

As used herein, "alkoxy" refers to the formula —OR wherein R is an alkyl, an alkenyl, an alkynyl, a cycloalkyl, a cycloalkenyl or a cycloalkynyl is defined as above. A non-limiting list of alkoxys are methoxy, ethoxy, n-propoxy, 1-methylethoxy (isopropoxy), n-butoxy, iso-butoxy, sec-butoxy and tert-butoxy. An alkoxy may be substituted or unsubstituted.

As used herein, "acyl" refers to a hydrogen, alkyl, alkenyl, alkynyl, or aryl connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "aminoalkyl" refers to an optionally substituted amino group connected, as a substituent, via a lower alkylene group. Examples include $H_2N$—O—$(CH_2)_n$—, or (Boc)-NH—$(CH_2)_n$—, wherein n is an integer in the range of 1 to 6.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or unsubstituted.

As used herein, "aryloxy" and "arylthio" refers to RO— and RS—, in which R is an aryl, such as but not limited to phenyl. Both an aryloxy and arylthio may be substituted or unsubstituted.

As used herein, "arylalkoxy" refers to an alkoxy group in which one or more of the hydrogen atoms are replaced by an aryl group (e.g., —$OCH_2Ph$).

The term "amino" as used herein refers to a —$NH_2$ group.

As used herein, the term "hydroxy" refers to a —OH group.

A "cyano" group refers to a "—C≡N" group.

The term "azido" as used herein refers to a —$N_3$ group.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972), the disclosure of which is incorporated herein by reference in its entirety).

The term "pharmaceutically acceptable salt," especially when referring to a pharmaceutically acceptable salt of the compound of Formula (I), (Ia), (Ib), (Ic), (Id), (II), (III), (IV), (V) or (VI), refers to any pharmaceutically acceptable salts of a compound. Exemplary salts include an acid addition salt of a compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine. Exemplary pharmaceutically acceptable salts are the alkali metal salts (sodium or potassium), the alkaline earth metal salts (calcium or magnesium), or ammonium salts derived from ammonia or from pharmaceutically acceptable organic amines, for example $C_1$-$C_7$ alkylamine, cyclohexylamine, triethanolamine, ethylenediamine or tris-(hydroxymethyl)-aminomethane. With respect to compounds that are basic amines, exemplary pharmaceutically acceptable salts are acid addition salts of pharmaceutically acceptable inorganic or organic acids, for example, hydrohalic, sulfuric, phosphoric acid or aliphatic or aromatic carboxylic or sulfonic acid, for example acetic, succinic, lactic, malic, tartaric, citric, ascorbic, nicotinic, methanesulfonic, p-toluensulfonic or naphthalenesulfonic acid.

The term "pharmaceutical composition" refers to a mixture of one or more compounds disclosed herein with other chemical components, such as diluents or carriers.

The term "physiologically acceptable" defines a carrier, diluent or excipient that does not abrogate the biological activity and properties of the compound.

As used herein, a "carrier" refers to a compound that facilitates the incorporation of a compound into cells or tissues.

As used herein, an "excipient" refers to an inert substance that is added to a pharmaceutical composition to provide, without limitation, bulk, consistency, stability, binding ability, lubrication, disintegrating ability etc., to the composition.

A "diluent" is a type of excipient. A "diluent" refers to an ingredient in a pharmaceutical composition that lacks pharmacological activity but may be pharmaceutically necessary or desirable.

As used herein, the term "subject" refers to a mammal. Exemplary mammals include, but are not limited to, humans, domestic animals (e.g., a dog, cat, or the like), farm animals (e.g., a cow, a sheep, a pig, a horse, or the like) or laboratory animals (e.g., a monkey, a rat, a mouse, a rabbit, a guinea pig, or the like).

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance.

The term "therapeutically effective amount" is used to indicate an amount of an active compound, or pharmaceutical agent, that elicits a biological or medicinal response.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

II. The Ubiquitin-Proteasome System (UPS)

The ubiquitin-proteasome system (UPS) controls the stability, interactions, and localization of many thousands of proteins across virtually all cellular processes. The UPS degrades damaged proteins and provides an important biological mechanism for removing dysfunctional proteins created by transcription, translation and/or folding errors.

The UPS conjugates ubiquitin onto lysine residues of damaged proteins. Ubiquitin is a highly conserved 76-amino acid polypeptide that is abundantly present in eukaryotic cells. Ubiquitin conjugation by the UPS is catalyzed by an enzymatic cascade of at least three classes of enzymes: (i) E1, (ii) E2, and (iii) E3. The E1 enzyme activates ubiquitin as a thioester and transfers the activated ubiquitin to a catalytic cysteine residue of E2. The E2 enzyme is a serves as a ubiquitin carrier. The E3 enzyme is a ubiquitin protein ligase that attaches the activated ubiquitin to the damaged protein. The resulting ubiquitylated protein can be targeted to lysosomes or proteasomes.

In certain diseases the UPS becomes compromised, either leading to excessive accumulation of unwanted proteins or the abnormal degradation of desired proteins. Perturbation of the UPS is involved in a number of neoplastic diseases, age-related diseases, neurological diseases, immunological diseases, and infectious diseases. For example, an overactive UPS can lead to the degradation of desired proteins, such as degradation of tumor suppressor proteins. Alternatively, an underactive UPS can lead to the accumulation of undesired proteins, such as accumulation of oncogenic proteins. A malfunctioning UPS can lead to unregulated cellular proliferation and the formation of one or more neoplasms. Accordingly, there is a need for compounds and compositions that can regulate the UPS. Desired biological properties of such compounds and compositions include one or more of the following: high efficacy, high potency, low toxicity, high stability, specificity for UPS components, and a long biological half-life.

III. Compounds

Compounds of Formula (I) can regulate the UPS. For example, compounds of Formula (I) can inhibit Cdc34, which is the primary E2 enzyme for the cullin-RING ligase (CRL) superfamily class of E3 enzymes. In some embodiments, compounds of Formula (I) can inhibit hCdc34.

Some embodiments disclosed herein relate to a compound of Formula (I) or a pharmaceutically acceptable salt thereof:

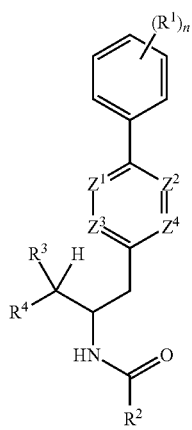

wherein: n can be selected from 0, 1, 2, 3, 4, and 5; each $R^1$ can be independently selected from halo, cyano, and azido; $Z^1$, $Z^2$, $Z^3$, and $Z^4$ can be each independently —CH— or —N—; $R^2$ can be selected from an optionally substituted ($C_{1-6}$ alkoxy)$C_{1-6}$ alkyl, an optionally substituted $C_{6-10}$ aryl, an optionally substituted $C_{5-10}$ heteroaryl, an optionally substituted (aryloxy)$C_{1-6}$ alkyl, an optionally substituted $C_{3-7}$ heterocyclyl, an optionally substituted $C_{3-7}$ cycloalkyl, an optionally substituted haloalkyl, and an optionally substituted aminoalkyl; $R^3$ can be hydrogen or —OH; $R^4$ can be selected from an optionally substituted $C_{3-6}$ cycloalkyl, an optionally substituted $C_{3-6}$ heterocyclyl, an optionally substituted $C_{6-10}$ aryl, an optionally substituted $C_{5-10}$ heteroaryl,

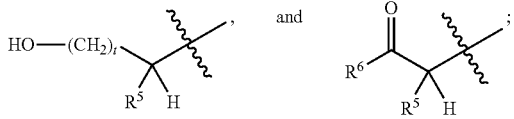

or $R^3$ and $R^4$ together form an optionally substituted $C_{3-6}$ heterocyclic ring; $R^5$ can be hydrogen or —OH; $R^6$ can be selected from —OH, —NHR$^7$, an optionally substituted $C_{1-6}$ alkyl, an optionally substituted $C_{1-6}$ alkoxy, an optionally substituted $C_{6-10}$ aryl, an optionally substituted $C_{5-10}$ heteroaryl, an optionally substituted aryloxy, or an optionally substituted arylalkoxy; $R^7$ can be hydrogen or an optionally substituted $C_{1-6}$ alkyl; t can be selected from 0, 1, 2, 3, 4, and 5; provided that if n is 2, both $R^1$ are chloro, $R^2$ is methoxymethyl, $R^3$ is —OH, $R^4$ is —CH(OH)CH$_2$OH or

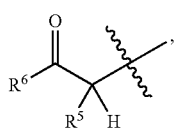

$R^5$ is —OH, and $R^6$ is —OH, —NHR$^7$, or methoxy; then at least one of $Z^1$, $Z^2$, $Z^3$, and $Z^4$ is —N—; further provided that if n is 2, both $R^1$ are chloro, $R^2$ is methoxymethyl or phenyl, $R^3$ is hydrogen, $R^4$ is

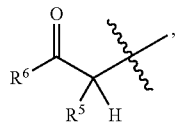

$R^5$ is hydrogen, and $R^6$ is —OH; then at least one of $Z^1$, $Z^2$, $Z^3$, and $Z^4$ is —N—; provided that if n is 2, both $R^1$ are chloro, $R^2$ is methoxymethyl, and $R^3$ and $R^4$ together form an optionally substituted heterocyclic ring, then at least one of $Z^1$, $Z^2$, $Z^3$, and $Z^4$ is —N—; provided that if n is 2, both $R^1$ are chloro, $R^2$ is methoxymethyl, $R^3$ is —OH, $R^4$ is

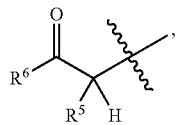

$R^5$ is —OH, then $R^6$ cannot be —OH, —NH(CH$_2$)$_3$OCH$_3$, or —NH(CH$_2$)$_3$N(CH$_3$)$_2$; provided that if n is 2, both $R^1$ are chloro, $R^2$ is methoxymethyl, $R^3$ is —OH, $R^4$ is

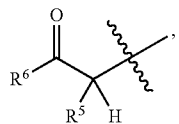

$R^5$ is —OH, $R^6$ is methoxy, then the compound cannot be

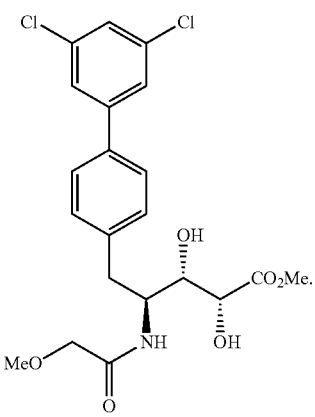 [SMILES: COCC(=O)N[C@@H](Cc1ccc(-c2cc(Cl)cc(Cl)c2)cc1)[C@H](O)[C@@H](O)C(=O)OC]

Some embodiments disclosed herein relate to a compound of Formula (I) or a pharmaceutically acceptable salt thereof, wherein: n can be selected from 0, 1, 2, 3, 4, and 5; each $R^1$ can be independently selected from halo, cyano, and azido; $Z^1$, $Z^2$, $Z^3$, and $Z^4$ can be each independently —CH— or —N—; $R^2$ can be selected from an optionally substituted ($C_{1-6}$ alkoxy)$C_{1-6}$ alkyl, an optionally substituted $C_{6-10}$ aryl, and an optionally substituted $C_{5-10}$ heteroaryl; $R^3$ can be hydrogen or —OH; $R^4$ can be selected from an optionally substituted $C_{3-6}$ cycloalkyl, an optionally substituted $C_{3-6}$ heterocyclyl, an optionally substituted $C_{6-10}$ aryl, an optionally substituted $C_{5-10}$ heteroaryl, and

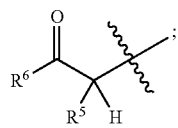

$R^5$ can be hydrogen or —OH; $R^6$ can be selected from —OH, an optionally substituted $C_{1-6}$ alkyl, an optionally substituted $C_{2-6}$ alkoxy, an optionally substituted $C_{6-10}$ aryl, an optionally substituted $C_{5-10}$ heteroaryl; $R^7$ can be hydrogen or an optionally substituted $C_{1-6}$ alkyl; and provided that if $R^4$ is

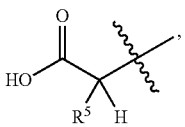

then $R^3$ and $R^5$ cannot be the same.

In some embodiments, n can be selected from the group consisting of 1, 2, 3, 4, and 5. In some embodiments, n can be 1 or 2. In some embodiments, n can be 2.

In some embodiments, each $R^1$ can be independently halo. In some embodiments, each $R^1$ can be independently chloro, fluoro, or bromo. In some embodiments, each $R^1$ can be chloro.

In some embodiments, $Z^1$ and $Z^2$ are each —CH—. In some embodiments, $Z^3$ and $Z^4$ are each —CH—. In some embodiments, $Z^3$ and $Z^4$ are each —N—. In some embodiments, $Z^3$ can be —CH—, and $Z^4$ can be —N—. In some embodiments, $Z^3$ can be —N—, and $Z^4$ can be —CH—. In some embodiments, each of $Z^1$, $Z^2$, $Z^3$, and $Z^4$ can be —CH—.

In some embodiments, $R^2$ can be ($C_{1-6}$ alkoxy)$C_{1-6}$ alkyl. In some embodiments, $R^2$ can be methoxymethyl. In some embodiments, $R^2$ can be ethoxymethyl. In some embodiments, $R^2$ can be $C_{6-10}$ aryl. In some embodiments, $R^2$ can be phenyl. In some embodiments, $R^2$ can be $C_{5-10}$ heteroaryl. In some embodiments, $R^2$ can be furanyl. In some embodiments, $R^2$ can be (aryloxy)$C_{1-6}$ alkyl. In some embodiments, $R^2$ can be phenoxymethyl. In some embodiments, $R^2$ can be $C_{3-7}$ heterocyclyl. In some embodiments, $R^2$ is selected from optionally substituted tetrahydrofuranyl or optionally substituted pyrrolidinyl. In some embodiments, the nitrogen atom in pyrrolidinyl is protected with a t-butyloxycarbonyl (Boc) protecting group. In some embodiments, $R^2$ can be $C_{3-7}$ cycloalkyl. In some embodiments, $R^2$ can be cyclopentyl. In some embodiments, $R^2$ can be haloalkyl. In some embodiments, $R^2$ can be selected from —$CH_2Cl$, —$CH_2Br$, —$CH_2CH_2Cl$, —$CH_2CH_2Br$, —CH(Cl)$CH_3$ or —CH(Br)$CH_3$. In some embodiments, $R^2$ can be optionally substituted Aminoalkyl. In some embodiments, $R^2$ can be selected from —$CH_2NH_2$, —$CH_2NH(Boc)$, —CH($NH_2$)$CH_3$, and —CH(Boc-NH)$CH_3$.

In some embodiments, $R^3$ can be hydrogen. In some embodiments, $R^3$ can be —OH.

In some embodiments, $R^4$ can be $C_{3-6}$ cycloalkyl. In some embodiments, $R^4$ can be cyclohexyl. In some embodiments, $R^4$ can be $C_{3-6}$ heterocyclyl. In some embodiments, $R^4$ can be 1,4,-dioxan-2-one-3-yl. In some embodiments, $R^4$ can be $C_{6-10}$ aryl. In some embodiments, $R^4$ can be phenyl. In some embodiments, $R^4$ can be phenol-2-yl. In some embodiments, $R^4$ can be $C_{5-10}$ heteroaryl. In some embodiments, $R^4$ can be In some embodiments, $R^4$ can be

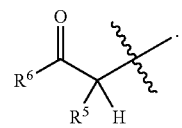

In some embodiments, $R^4$ can be

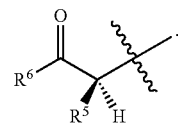

In some embodiments, $R^4$ can be

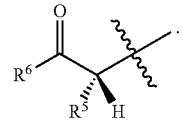

In some embodiments, $R^5$ can be hydrogen. In some embodiments, $R^5$ can be —OH.

In some embodiments, $R^6$ can be selected from the group consisting of —OH, —$NHR^7$, an optionally substituted $C_{1-6}$ alkoxy, and an optionally substituted arylalkoxy. In some embodiments, $R^6$ can be —OH. In some embodiments, $R^6$ can be —$OCH_2Ph$. In some embodiments, $R^6$ can be —$OCH_2CH_3$. In some embodiments, $R^6$ can be a substituted $C_{1-6}$ alkyl. In some embodiments, the $C_{1-6}$ alkyl can be substituted with one or more groups selected from among halogen, —OH, —COOH, —$NR^8R^9$, $C_{1-6}$ alkoxy, and $C_{5-10}$ heteroaryl; wherein $R^8$ and $R^9$ are each independently hydrogen or $C_{1-6}$ alkyl. In some embodiments, the $C_{1-6}$ alkyl can be substituted with —COOH or $C_{5-10}$ heteroaryl. In some embodiments, $R^6$ can be $C_{6-10}$ aryl. In some embodiments, $R^6$ can be phenyl. In some embodiments, $R^6$ can be —$NHR^7$.

In some embodiments, $R^7$ can be an optionally substituted $C_{1-6}$ alkyl. In some embodiments, the $C_{1-6}$ alkyl can be substituted with one or more groups selected from $C_{1-6}$ alkoxy and —$NR^8R^9$; wherein $R^8$ and $R^9$ are each independently hydrogen or $C_{1-6}$ alkyl.

In some embodiments, $R^3$ and $R^4$ together form an optionally substituted $C_{3-6}$ heterocyclic ring.

In some embodiments, the compound of Formula (I) can have the structure of Formula (II), or a pharmaceutically acceptable salt thereof:

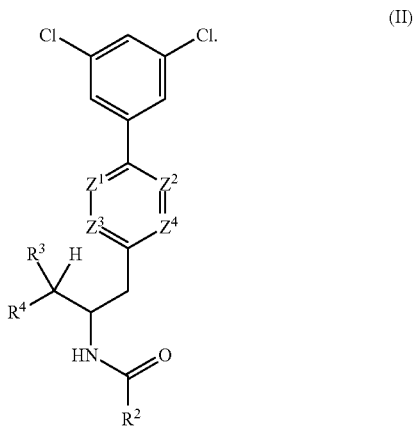

(II)

In some embodiments, the compound of Formula (I) can have the structure of Formula (III), or a pharmaceutically acceptable salt thereof:

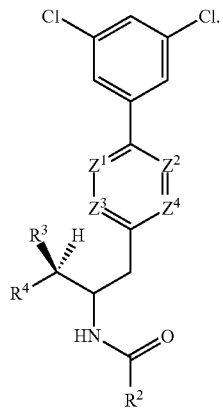

(III)

In some embodiments, the compound of Formula (I) can have the structure of Formula (IV), or a pharmaceutically acceptable salt thereof:

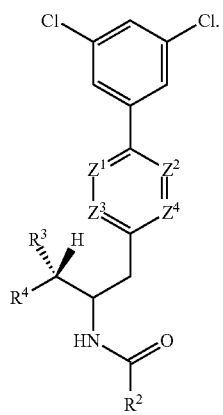

(IV)

In some embodiments, the compound of Formula (I) can have the structure of Formula (V), or a pharmaceutically acceptable salt thereof:

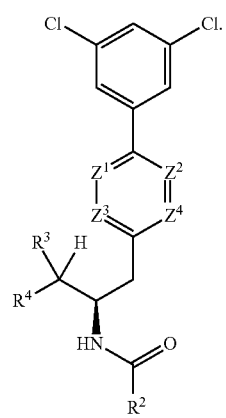

(V)

In some embodiments, the compound of Formula (I) can have the structure of Formula (VI), or a pharmaceutically acceptable salt thereof:

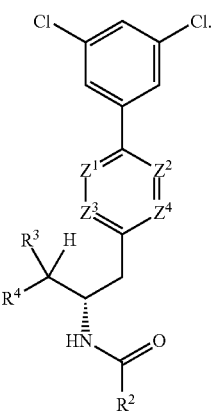

(VI)

In some embodiments, $R^4$ of Formula (II), Formula (III), Formula (IV), Formula (V) or Formula (VI) can be selected from selected from

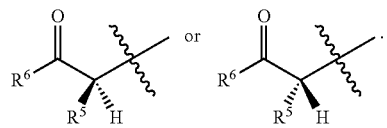

Examples of compounds of Formula (I) include, but are not limited to the following:

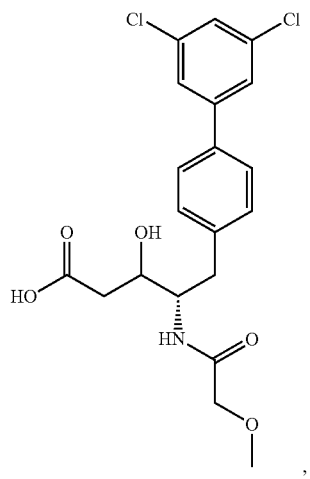

17
-continued
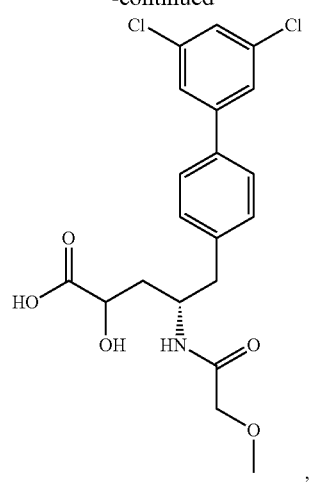
18
-continued
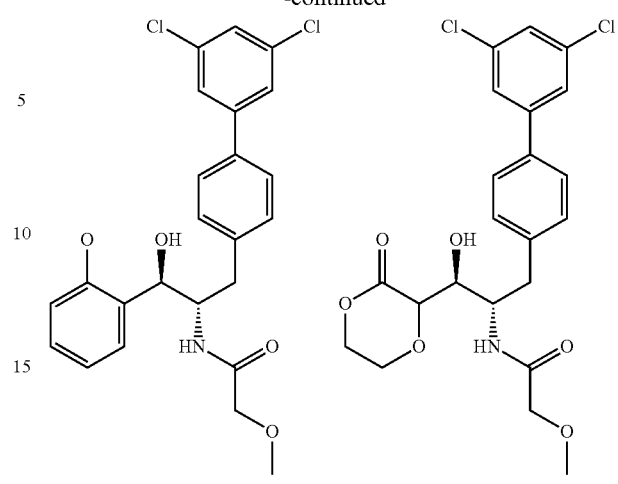
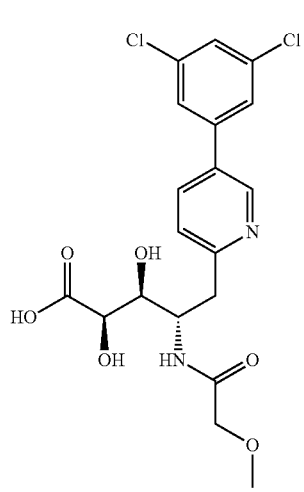
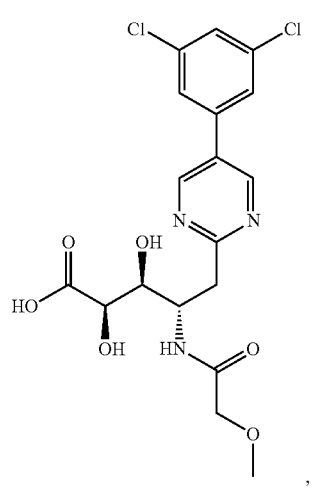
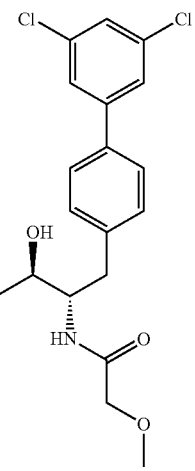

-continued
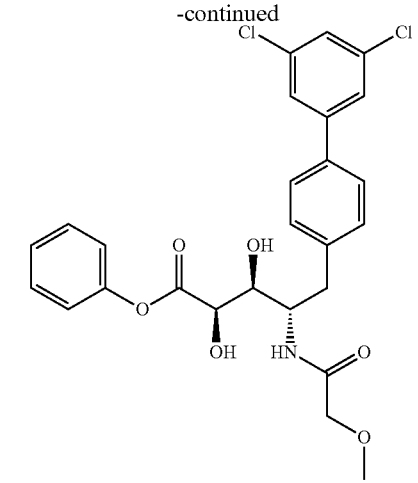
,
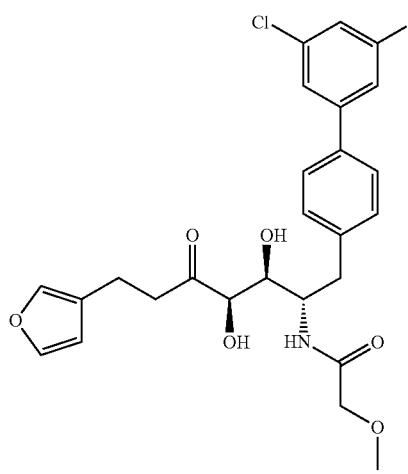
, and
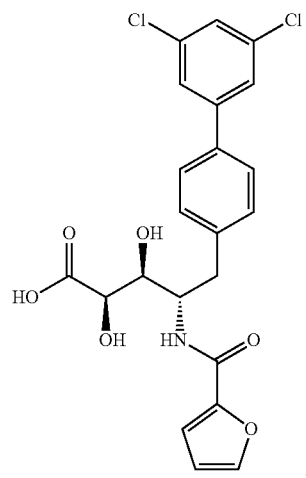
,
and pharmaceutically acceptable salts thereof.
In some embodiments, examples of compounds of Formula (I) is selected from Table 1, compounds B1 through B15.
TABLE 1
| | |
|---|---|
| B1 | 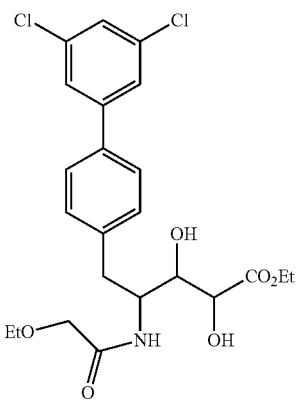 [SMILES: CCOCC(=O)NC(Cc1ccc(-c2cc(Cl)cc(Cl)c2)cc1)C(O)C(O)C(=O)OCC] |
| B2 | 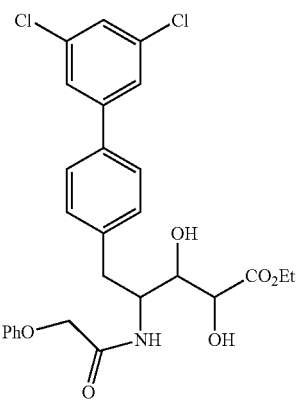 |
| B3 | 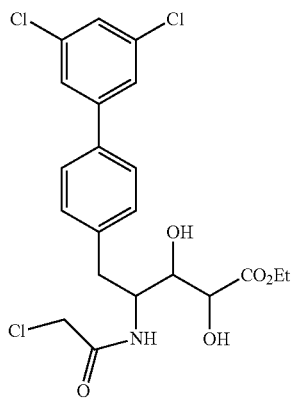 [SMILES: CCOC(=O)C(O)C(O)C(Cc1ccc(-c2cc(Cl)cc(Cl)c2)cc1)NC(=O)CCl] |
| B4 | 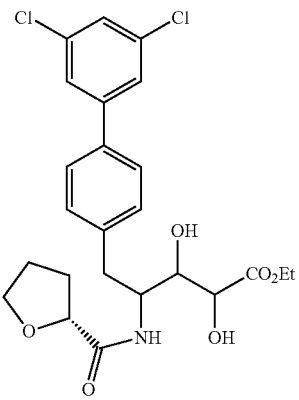 [SMILES: CCOC(=O)C(O)C(O)C(Cc1ccc(-c2cc(Cl)cc(Cl)c2)cc1)NC(=O)[C@H]1CCCO1] |

TABLE 1-continued
| B5 | 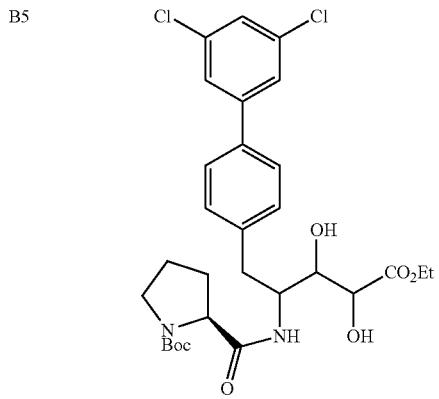 |
| B6 | 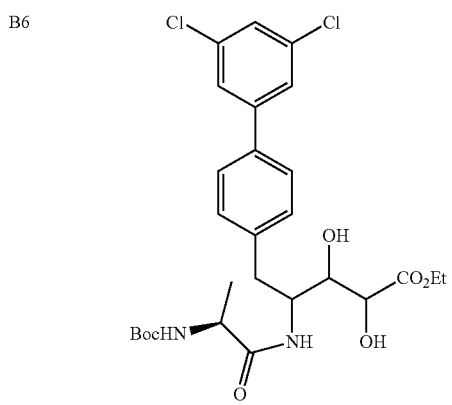 |
| B7 | 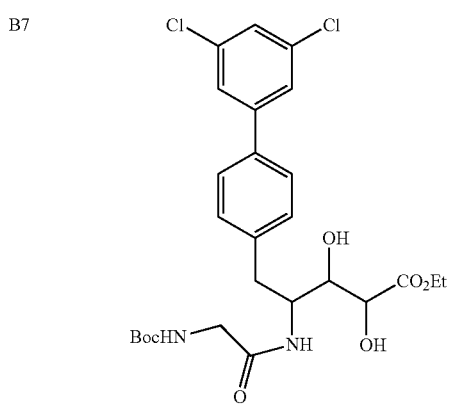 |
| B8 | 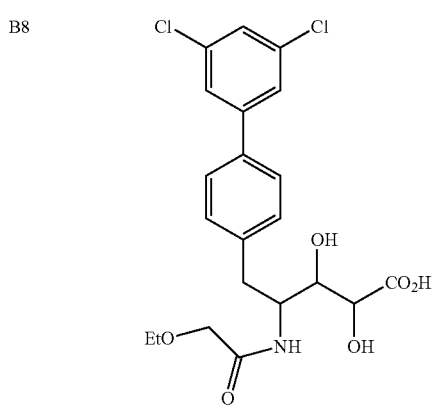 |
| B9 | 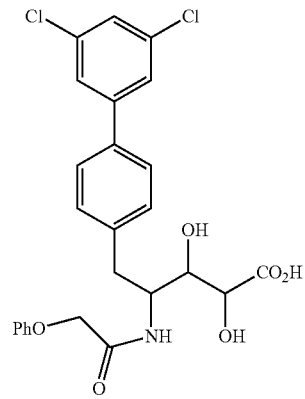 [SMILES: O=C(COc1ccccc1)NC(Cc1ccc(-c2cc(Cl)cc(Cl)c2)cc1)C(O)C(O)C(=O)O] |
| B10 | 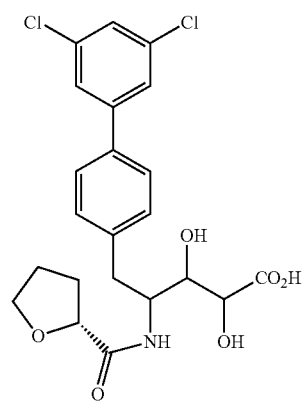 [SMILES: O=C(O)C(O)C(O)C(Cc1ccc(-c2cc(Cl)cc(Cl)c2)cc1)NC(=O)[C@H]1CCCO1] |
| B11 | 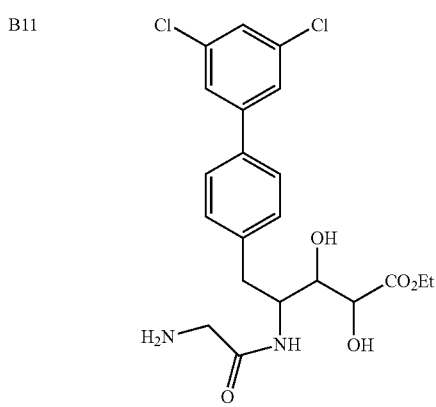 |
| B12 | 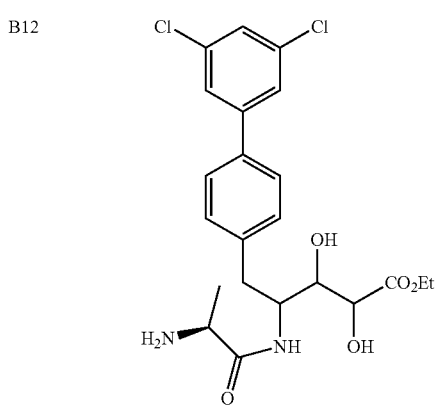 |

TABLE 1-continued
| | |
|---|---|
| B13 | 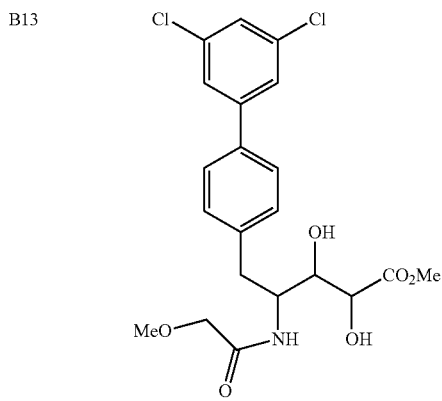 |
| B14 | 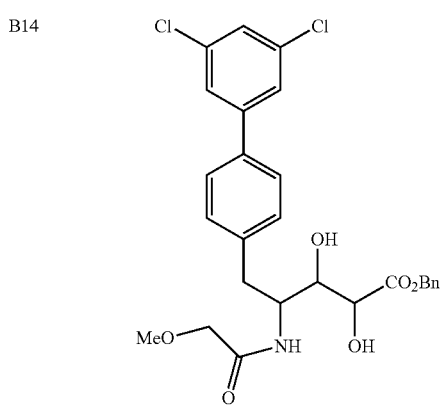 |
| B15 | 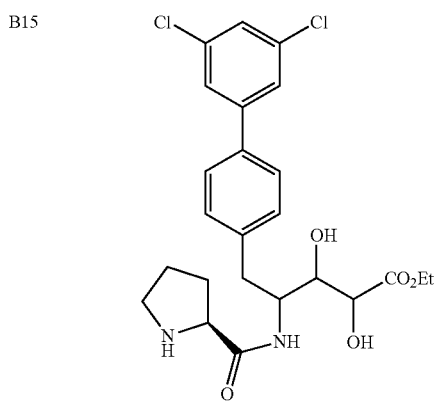 |
TABLE 2
| | |
|---|---|
| C1 | 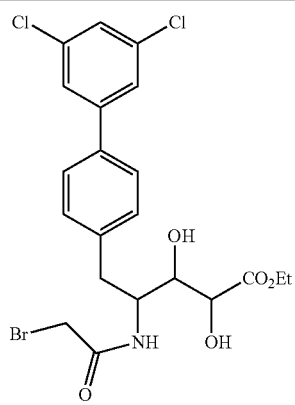 |
| C2 | 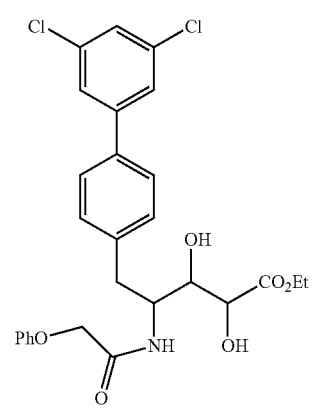 [SMILES: CCOC(=O)C(O)C(O)C(Cc1ccc(-c2cc(Cl)cc(Cl)c2)cc1)NC(=O)COc1ccccc1] |
| C3 | 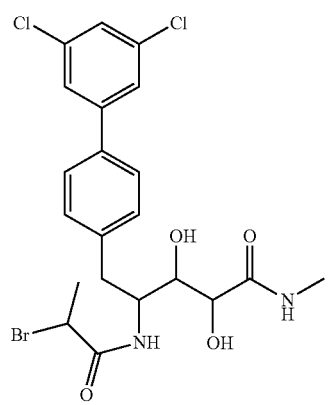 [SMILES: CNC(=O)C(O)C(O)C(Cc1ccc(-c2cc(Cl)cc(Cl)c2)cc1)NC(=O)C(C)Br] |
| C4 | 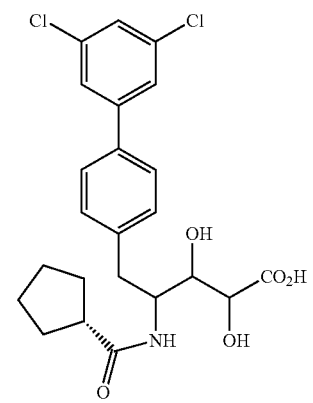 |
In some embodiments, examples of compounds of Formula (I) is selected from Table 2, compounds C1 through C5.

TABLE 2-continued

C5
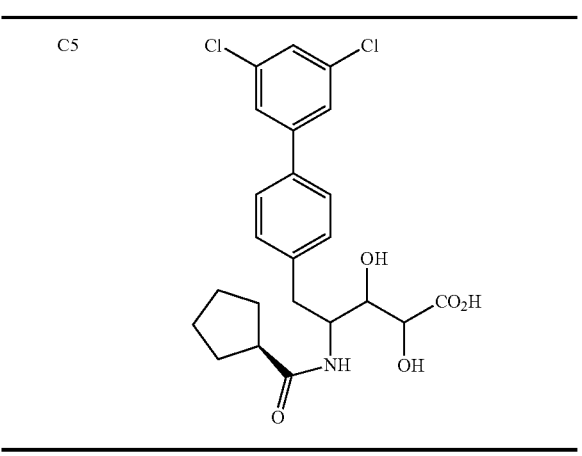

In some embodiments, the exemplary compounds can be enriched with respect to the shown stereochemistry in an amount >50%, ≥60%, ≥70%, ≥80%, ≥90%, ≥95%, or ≥98% as compared to the amount of other stereoisomer impurities.

Some embodiments disclosed herein relate to a compound of Formula (Ia), (Ib), (Ic) or (Id), or a pharmaceutically acceptable salt thereof:

(Ia)
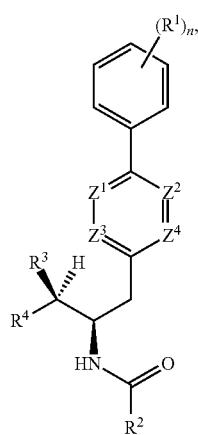

(Ib)
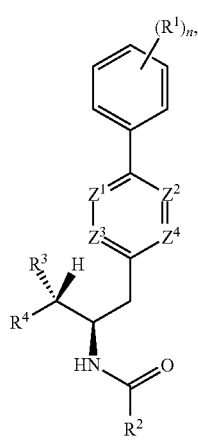

(Ic)
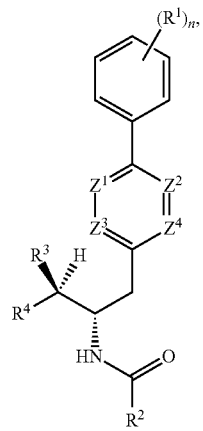

(Id)
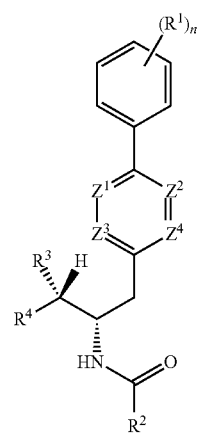

wherein: n can be selected from 0, 1, 2, 3, 4, and 5; each $R^1$ can be independently selected from halo, cyano, and azido; $Z^1$, $Z^2$, $Z^3$, and $Z^4$ are each independently —CH— or —N—; $R^2$ can be selected from an optionally substituted ($C_{1-6}$ alkoxy)$C_{1-6}$ alkyl, an optionally substituted $C_{6-10}$ aryl, an optionally substituted $C_{5-10}$ heteroaryl, an optionally substituted (aryloxy)$C_{1-6}$ alkyl, an optionally substituted $C_{3-7}$ heterocyclyl, an optionally substituted $C_{3-7}$ cycloalkyl, an optionally substituted haloalkyl, and an optionally substituted aminoalkyl; $R^3$ can be hydrogen or —OH; $R^4$ can be selected from an optionally substituted $C_{3-6}$ cycloalkyl, an optionally substituted $C_{3-6}$ heterocyclyl, an optionally substituted $C_{6-10}$ aryl, an optionally substituted $C_{5-10}$ heteroaryl, $$HO-(CH_2)_t \overset{R^5}{\underset{H}{\diagdown}}, \quad HO-(CH_2)_t \overset{R^5}{\underset{H}{\diagdown}},$$

$$\overset{O}{\underset{R^6}{\diagdown}} \overset{R^5}{\underset{H}{\diagdown}}, \text{ and } \overset{O}{\underset{R^6}{\diagdown}} \overset{R^5}{\underset{H}{\diagdown}};$$

or $R^3$ and $R^4$ together form an optionally substituted $C_{3-6}$ heterocyclic ring; $R^5$ can be hydrogen or —OH; $R^6$ can be selected from —OH, —$NHR^7$, an optionally substituted $C_{1-6}$ alkyl, an optionally substituted $C_{1-6}$ alkoxyl, an optionally substituted $C_{6-10}$ aryl, an optionally substituted $C_{5-10}$ heteroaryl an optionally substituted aryloxy, or an optionally substituted arylalkoxy; $R^7$ can be hydrogen or an optionally substituted $C_{1-6}$ alkyl; and t can be selected from the group consisting of 0, 1, 2, 3, 4, and 5, provided that if n is 2, both $R^1$ are chloro, $R^2$ is methoxymethyl, $R^3$ is —OH, $R^4$ is

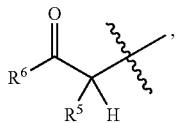

$R^5$ is —OH, then $R^6$ cannot be —OH, —NH(CH$_2$)$_3$OCH$_3$, or —NH(CH$_2$)$_3$N(CH$_3$)$_2$; provided that if n is 2, both $R^1$ are chloro, $R^2$ is methoxymethyl, $R^3$ is —OH, $R^4$ is

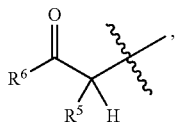

$R^5$ is —OH, $R^6$ is methoxy, then the compound cannot be

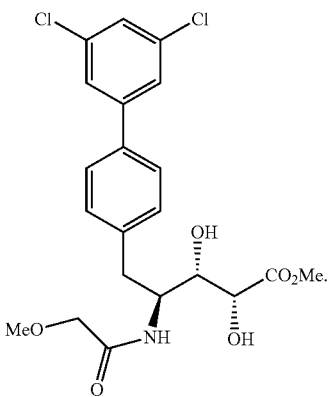 [SMILES: COCC(=O)N[C@@H](Cc1ccc(-c2cc(Cl)cc(Cl)c2)cc1)[C@H](O)[C@@H](O)C(=O)OC]

Some embodiments disclosed herein relate to a compound of Formula (Ia). Some embodiments disclosed herein relate to a compound of Formula (Ib). Some embodiments disclosed herein relate to a compound of Formula (Ic). Some embodiments disclosed herein relate to a compound of Formula (Id).

Some embodiments disclosed herein relate to a compound of Formula (Ic), or a pharmaceutically acceptable salt thereof, wherein: n can be 2; both $R^1$ can be chloro; $R^2$ can be methoxymethyl; $R^3$ can be —OH; $R^4$ can be

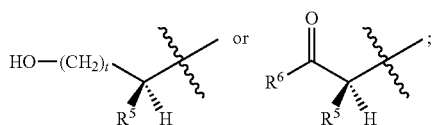

$R^5$ can be —OH; $R^6$ can be —OH, —NHR$^7$, or methoxy; and at least one of $Z^1$, $Z^2$, $Z^3$, and $Z^4$ can be —N—.

Some embodiments disclosed herein relate to a compound of Formula (Id), or a pharmaceutically acceptable salt thereof, wherein: n can be 2; both $R^1$ can be chloro; $R^2$ can be methoxymethyl or phenyl; $R^3$ can be hydrogen; $R^4$ can be

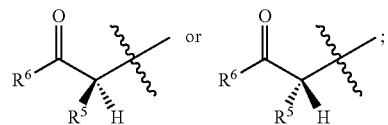

$R^5$ can be hydrogen; $R^6$ can be —OH; and at least one of $Z^1$, $Z^2$, $Z^3$, and $Z^4$ can be —N—.

Some embodiments disclosed herein relate to a compound of Formula (Ia) or (Ic), or a pharmaceutically acceptable salt thereof, wherein: n can be 2; both $R^1$ are chloro; $R^2$ can be methoxymethyl; $R^3$ and $R^4$ together form an optionally substituted heterocyclic ring; and at least one of $Z^1$, $Z^2$, $Z^3$, and $Z^4$ can be —N—.

In some embodiments, n can be selected from the group consisting of 1, 2, 3, 4, and 5. In some embodiments, n can be 1 or 2. In some embodiments, n can be 2.

In some embodiments, each $R^1$ can be independently halo. In some embodiments, each $R^1$ can be independently chloro, fluoro, or bromo. In some embodiments, each $R^1$ can be chloro.

In some embodiments, $Z^1$ and $Z^2$ are each —CH—. In some embodiments, $Z^3$ and $Z^4$ are each —CH—. In some embodiments, $Z^3$ and $Z^4$ are each —N—. In some embodiments, $Z^3$ can be —CH—, and $Z^4$ can be —N—. In some embodiments, $Z^3$ can be —N—, and $Z^4$ can be —CH—. In some embodiments, each of $Z^1$, $Z^2$, $Z^3$, and $Z^4$ can be —CH—.

In some embodiments, $R^2$ can be (C$_{1-6}$ alkoxy)C$_{1-6}$ alkyl. In some embodiments, $R^2$ can be methoxymethyl. In some embodiments, $R^2$ can be ethoxymethyl. In some embodiments, $R^2$ can be C$_{6-10}$ aryl. In some embodiments, $R^2$ can be phenyl. In some embodiments, $R^2$ can be C$_{5-10}$ heteroaryl. In some embodiments, $R^2$ can be furanyl. In some embodiments, $R^2$ can be (aryloxy)C$_{1-6}$ alkyl. In some embodiments, $R^2$ can be phenoxymethyl. In some embodiments, $R^2$ can be C$_{3-7}$ heterocyclyl. In some embodiments, $R^2$ is selected from optionally substituted tetrahydrofuranyl or optionally substituted pyrrolidinyl. In some embodiments, the nitrogen atom in pyrrolidinyl is protected with a t-butyloxycarbonyl (Boc) protecting group. In some embodiments, $R^2$ can be $C_{3-7}$ cycloalkyl. In some embodiments, $R^2$ can be cyclopentyl. In some embodiments, $R^2$ can be haloalkyl. In some embodiments, $R^2$ can be selected from —CH$_2$Cl, —CH$_2$Br, —CH$_2$CH$_2$Cl, —CH$_2$CH$_2$Br, —CH(Cl)CH$_3$ or —CH(Br)CH$_3$. In some embodiments, $R^2$ can be optionally substituted aminoalkyl. In some embodiments, $R^2$ can be selected from —CH$_2$NH$_2$, —CH$_2$NH(Boc), —CH(NH$_2$)CH$_3$, and —CH(Boc-NH)CH$_3$.

In some embodiments, $R^3$ can be hydrogen. In some embodiments, $R^3$ can be —OH.

In some embodiments, $R^4$ can be C$_{3-6}$ cycloalkyl. In some embodiments, $R^4$ can be cyclohexyl. In some embodiments, $R^4$ can be C$_{3-6}$ heterocyclyl. In some embodiments, $R^4$ can be 1,4,-dioxan-2-one-3-yl. In some embodiments, $R^4$ can be C$_{6-10}$ aryl. In some embodiments, $R^4$ can be phenyl. In some embodiments, $R^4$ can be phenol-2-yl. In some embodiments, $R^4$ can be C$_{5-10}$ heteroaryl. In some embodiments, $R^4$ can be

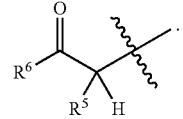

In some embodiments, $R^4$ can be

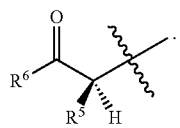

In some embodiments, $R^4$ can be

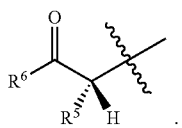

In some embodiments, $R^5$ can be hydrogen. In some embodiments, $R^5$ can be —OH.

In some embodiments, $R^6$ can be selected from the group consisting of —OH, —$NHR^7$, an optionally substituted $C_{1-6}$ alkoxy, and an optionally substituted arylalkoxy. In some embodiments, $R^6$ can be —OH. In some embodiments, $R^6$ can be —$OCH_2Ph$. In some embodiments, $R^6$ can be —$OCH_2CH_3$. In some embodiments, $R^6$ can be a substituted $C_{1-6}$ alkyl. In some embodiments, the $C_{1-6}$ alkyl can be substituted with one or more groups selected from among halogen, —OH, —COOH, —$NR^8R^9$, $C_{1-6}$ alkoxy, and $C_{5-10}$ heteroaryl; wherein $R^8$ and $R^9$ are each independently hydrogen or $C_{1-6}$ alkyl. In some embodiments, the $C_{1-6}$ alkyl can be substituted with —COOH or $C_{5-10}$ heteroaryl. In some embodiments, $R^6$ can be $C_{6-10}$ aryl. In some embodiments, $R^6$ can be phenyl. In some embodiments, $R^6$ can be —$NHR^7$.

In some embodiments, $R^7$ can be an optionally substituted $C_{1-6}$ alkyl. In some embodiments, the $C_{1-6}$ alkyl can be substituted with one or more groups selected from $C_{1-6}$ alkoxy and —$NR^8R^9$; wherein $R^8$ and $R^9$ are each independently hydrogen or $C_{1-6}$ alkyl.

In some embodiments, $R^3$ and $R^4$ together form an optionally substituted $C_{3-6}$ heterocyclic ring.

In some embodiments, the compound of Formula (I)-(VI) (which can include a compound of Formula (Ia), (Ib), (Ic), or (Id)) can be enriched in the (R) or (S) enantiomer or diastereomer with respect to any chiral carbon atom. For example, a compound of Formula (I)-(VI) can be enriched in the (R) or (S) configuration at any chiral carbon atom in an amount >50%, ≥60%, ≥70%, ≥80%, ≥90%, ≥95%, or ≥98% compared to the amount of the other of the (R) or (S) configuration. Some compounds of Formula (I)-(VI) can be enriched in a diastereomer having two or more chiral carbon atoms. In some embodiments, the compound can include a single enantiomer or diastereomer of a compound of Formula (I) at a concentration of greater than 99% compared to the total concentration of the other enantiomers or diastereomers. In other embodiments, the compound can include a mixture of two or more diastereomers. For example, the compound can include a concentration of one diastereomer of >50%, ≥60%, ≥70%, ≥80%, ≥90%, ≥95%, or ≥98%, as compared to the total concentration of the other diastereomers. In some embodiments, the compound includes a 1:1 mixture of two diastereomers.

With respect to compounds of Formula (I) and (II), in some embodiments, the compounds are enriched in the (R) or (S) enantiomer or diastereomer with respect to any chiral carbon. In some embodiments, the compound of Formula (I) or (II) can be enriched in the (R) or (S) configuration at the sp³ hybridized carbon connected to the nitrogen atom of the —NHC(=O)— group. In some embodiments, the enrichment can be >50%, ≥60%, ≥70%, ≥80%, ≥90%, ≥95%, or ≥98%, as compared to the total concentration of other stereoisomers.

In some embodiments, the compound of Formula (I) or (II) can be enriched in the (R) or (S) configuration at the carbon connected to $R^3$ and $R^4$. In some embodiments, the enrichment can be >50%, ≥60%, ≥70%, ≥80%, ≥90%, ≥95%, or ≥98%, as compared to the total concentration of other stereoisomers.

In some embodiments, when $R^4$ of Formula (I) or (II) is

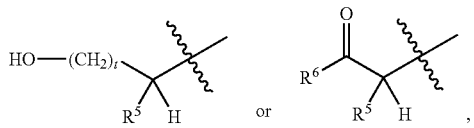

then the compound of Formula (I) or (II) can be enriched in the (R) or (S) configuration at the carbon connected to $R^5$ and $(CH_2)_t$—OH or the carbon connected to $R^5$ and C(=O)$R^6$. In some embodiments, the enrichment can be >50%, ≥60%, ≥70%, ≥80%, ≥90%, ≥95%, or ≥98%, as compared to the total concentration of other stereoisomers.

In some embodiments, the compound of Formula (I) or (II) can be enriched in the (R) or (S) configuration at the sp³ hybridized carbon connected to the nitrogen atom of the —NHC(=O)— group; and the compound can be enriched in the (R) or (S) configuration at the carbon connected to $R^3$ and $R^4$. In some embodiments, the enrichment can be >50%, ≥60%, ≥70%, ≥80%, ≥90%, ≥95%, or ≥98%, as compared to the total concentration of other stereoisomers.

In some embodiments, when $R^4$ of Formula (I) or (II) is

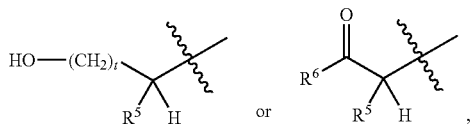

then the compound of Formula (I) or (II) can be enriched in the (R) or (S) configuration at the carbon connected to $R^5$ and $(CH_2)_t$—OH or the carbon connected to $R^5$ and C(=O)$R^6$; and the compound can be enriched in the (R) or (S) configuration at the sp³ hybridized carbon connected to the nitrogen atom of the —NHC(=O)— group. In some embodiments, the enrichment can be >50%, ≥60%, ≥70%, ≥80%, ≥90%, ≥95%, or ≥98%, as compared to the total concentration of other stereoisomers.

In some embodiments, when $R^4$ of Formula (I) or (II) is

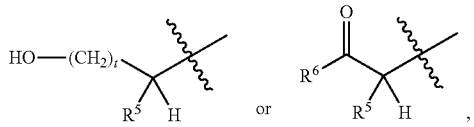

then the compound of Formula (I) or (II) can be enriched in the (R) or (S) configuration at the carbon connected to $R^5$ and $(CH_2)_t$—OH or the carbon connected to $R^5$ and C(=O)$R^6$; and the compound can be enriched in the (R) or (S) configuration at the carbon connected to $R^3$ and $R^4$. In some embodiments, the enrichment can be >50%, ≥60%, ≥70%, ≥80%, ≥90%, ≥95%, or ≥98%, as compared to the total concentration of other stereoisomers.

In some embodiments, when R⁴ of Formula (I) or (II) is

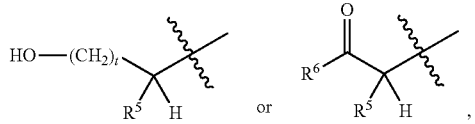

then the compound of Formula (I) or (II) can be enriched in the (R) or (S) configuration at the carbon connected to R⁵ and (CH₂)ₜ—OH or the carbon connected to R⁵ and C(=O)R⁶; and the compound can be enriched in the (R) or (S) configuration at the sp³ hybridized carbon connected to the nitrogen atom of the —NHC(=O)— group; and the compound can be enriched in the (R) or (S) configuration at the carbon connected to R³ and R⁴. In some embodiments, the enrichment can be >50%, ≥60%, ≥70%, ≥80%, ≥90%, ≥95%, or ≥98%, as compared to the total concentration of other stereoisomers.

In some embodiments, the compound of Formula (III)-(VI), (Ia), (Ib), (Ic), or (Id) can be enriched with respect to the shown stereochemistry in an amount >50%, ≥60%, ≥70%, ≥80%, ≥90%, ≥95%, or ≥98% as compared to the amount of other stereoisomer impurities. In some embodiments, the compound can be enriched with respect to the shown stereochemistry in an amount >99% as compared to the amount of other stereoisomer impurities.

IV. Screening

Compounds of Formula (I)-(VI) (which can include a compound of Formula (Ia), (Ib), (Ic) or (Id)) can be screened for their ability to inhibit Cdc34. In some embodiments, the compounds of Formula (I)-(IV) can be screened by using a high-throughput (HTP) compatible assay. This assay can be based on ubiquitination of the human cyclin-dependent kinase (CDK) inhibitor p27$^{Kip1}$ by SCF$^{Skp2}$, which is a Skp1-Cullin1-F-box (SCF) E3 complex. The SKP2 locus is often amplified and overexpressed in human cancer, thus SCF$^{Skp2}$ is a candidate for therapeutic intervention.

The HTP assay can contain biotinylated-ubiquitin, the E1 enzyme Uba1, the E2 enzyme hCcd34, the SCF$^{Skp2}$ complex, cyclin-dependent kinase regulatory subunit 1 (Cks1), and p27$^{Kip1}$ that is phosphorylated by cyclin E-Cdk2. Ubiquitination of p27$^{Kip1}$ can be assessed by capture onto an anti-p27$^{Kip1}$ antibody affinity surface and quantitative detection with a europium-streptavidin conjugate. See Ceccarelli et al., "An allosteric inhibitor of the human Cdc34 ubiquitin-conjugating enzyme," Cell 145:1075-1087, 2011, the disclosure of which is incorporated herein by reference in its entirety.

If the compound of Formula (I)-(VI) significantly reduces the extent of ubiquitination of p27$^{Kip1}$, then the compound can be a candidate therapeutic compound. If the compound of Formula (I)-(VI) significantly reduces the extent of ubiquitin chain initiation or ubiquitin chain length on p27$^{Kip1}$, then the compound can be a candidate therapeutic compound. Methods for screening compounds of Formula (I)-(VI) for their effects on the UPS are described in Ceccarelli et al., "An allosteric inhibitor of the human Cdc34 ubiquitin-conjugating enzyme," Cell 145:1075-1087, 2011, the disclosure of which is incorporated herein by reference in its entirety.

V. Properties

For more than a decade, researchers have been developing ways to target the ubiquitin-proteasome pathway in cancer. However, only one marketed therapy actually acts on this pathway, which is the proteasome inhibitor Velcade bortezomib [(R¹R)-3-methyl-1-(1-{(2S)-3-phenyl-2-[(pyrazin-2-ylcarbonyl)amino]propanoyl}-amino)butyl]boronic acid) that is marketed by Takeda Pharmaceutical Co. Ltd.'s Millennium Pharmaceuticals to treat multiple myeloma and mantle cell lymphoma. Kotz, "Celgene skips SKP2," SciBX 4(28) 2011, the disclosure of which is incorporated herein by reference in its entirety. Velcade's broad side-effect profile has prompted a search for better alternatives.

Researchers are interested in targeting the ubiquitin-proteasome pathway at points upstream from the proteasome. Ceccarelli et al. identified a small number of compounds that are able to somewhat regulate the ubiquitin-proteasome system (UPS). Ceccarelli et al., "An allosteric inhibitor of the human Cdc34 ubiquitin-conjugating enzyme," Cell 145:1075-1087, 2011. Specifically, Ceccarelli et al. demonstrated that compound CC0651 inhibits the E2 ubiquitin-conjugating enzyme hCdc34. However, the Ceccarelli team thought that it was too difficult to optimize CC0651 for the clinic and subsequently abandoned their program. Kotz, "Celgene skips SKP2," SciBX 4(28) 2011.

CC0651 is only a first step toward targeting an E2 enzyme, and a much more potent drug-like molecule is needed for clinical therapy. Kotz, "Celgene skips SKP2," SciBX 4(28) 2011 at page 1. Furthermore, David Webb, the Vice President of research at Celgene stated that the company does not plan to pursue CC0651 as a drug lead or Cdc34 target because "it was difficult to see a way forward to get below a micromolar IC$_{50}$." Id. Webb goes on to state that "The chemistry didn't look to us like it was going to get us to the potency needed for a drug." Id. Celgene had worked on the project for seven years, used an 11-protein assay, screened an enormous library twice, and could not advance any of the resulting compounds. Id. After two failed attempts to produce a nanomolar-potency inhibitor, the Celgene program was stopped. Id. "The ubiquitin ligases themselves are incredibly difficult to drug; we consider them relatively undruggable," said Webb. Id.

VI. Synthesis

The compounds described herein can be prepared in various ways. General synthetic routes to the compound of Formulae (I)-(VI) (which can include a compound of Formula (Ia), (Ib), (Ic) or (Id)), and some examples of materials and intermediates used to synthesize the compounds of Formulae (I)-(VI) are shown in Schemes 1-10, and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

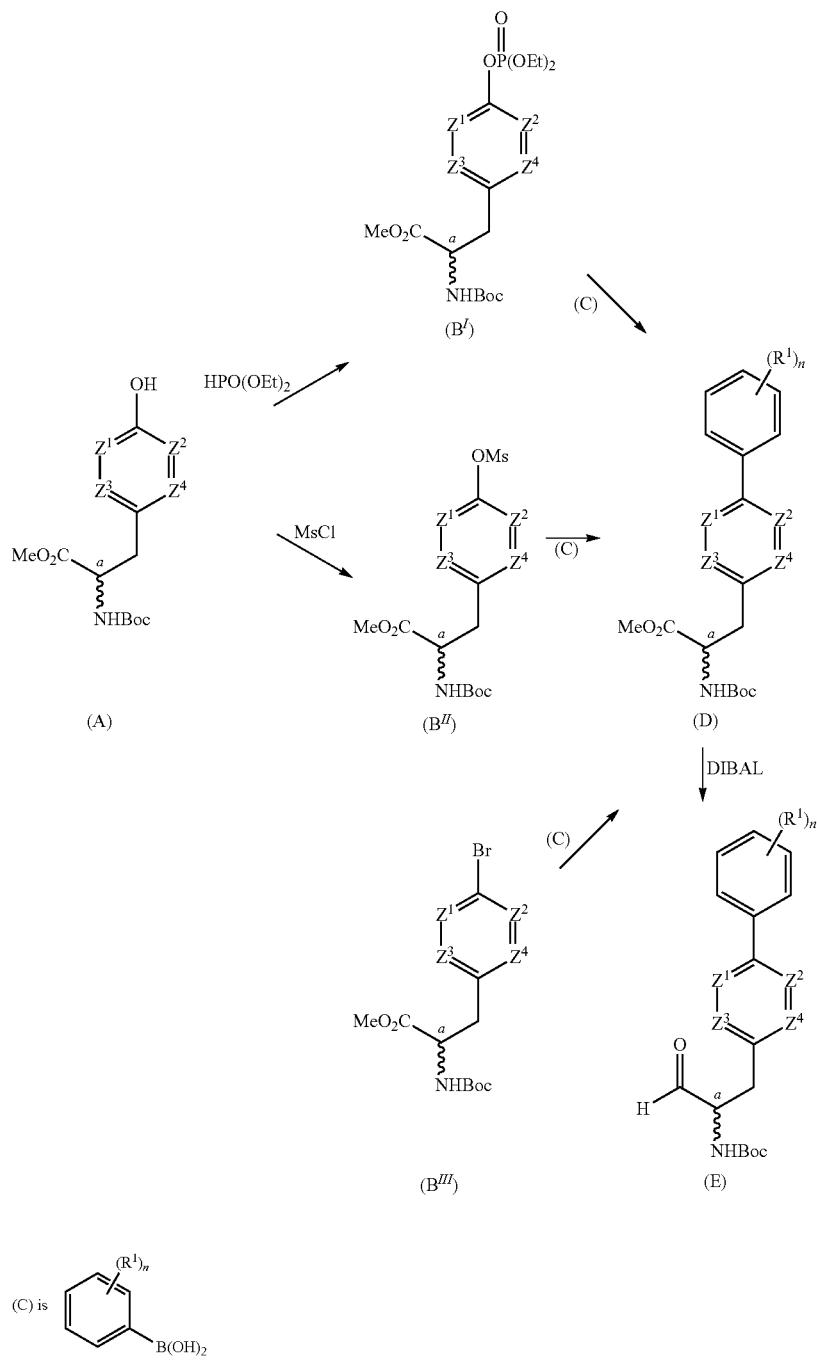

Scheme 1

Some methods for preparing a compound of Formula (E) are shown in Scheme 1. In Scheme 1, $Z^1$, $Z^2$, $Z^3$, $Z^4$, $R^1$ and n can be the same as $Z^1$, $Z^2$, $Z^3$, $Z^4$, $R^1$ and n as described herein for Formula (I). The compound of Formula (A) can be a racemic mixture of enantiomers. In some embodiments, the compound of Formula (A) can be stereospecific, having an (R) configuration about carbon 'a'. In some embodiments, the compound of Formula (A) can be stereospecific, having an (S) configuration about carbon 'a'. A compound of Formula ($B^I$) can be prepared by reacting a compound of Formula (A) with HPO(OEt)$_2$. A compound of Formula ($B^{II}$) can be prepared by reacting a compound of Formula (A) with methanesulfonyl chloride (MsCl).

A compound of Formula (D) can be prepared by reacting a compound of Formula ($B^I$), ($B^{II}$), or ($B^{III}$) with a compound of Formula (C). The reaction of a compound of Formula (B), ($B^{II}$), or ($B^{III}$) with a compound of Formula (C) results in inversion of the stereochemistry about carbon 'a'. A compound of Formula (E) can be prepared by reducing a compound of Formula (D). Suitable reducing agents include, but are not limited to, diisobutylaluminium hydride (DIBAL), lithium aluminium hydride (LiAlH$_4$), and sodium borohydride (NaBH$_4$).

Scheme 2

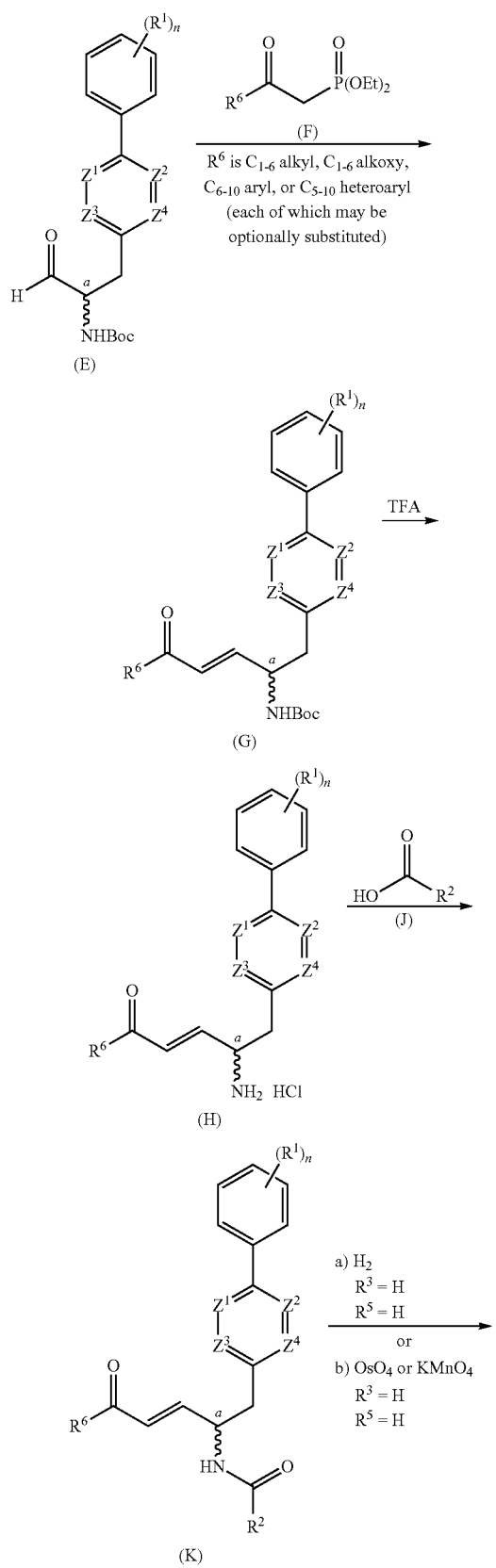

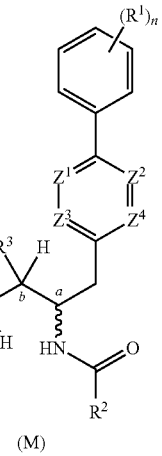

(L)

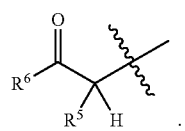

(M)

Some methods for preparing a compound of Formula (L) or (M) are shown in Scheme 2. In Scheme 2, $Z^1$, $Z^2$, $Z^3$, $Z^4$, $R^1$, $R^2$, $R^3$, $R^5$ and n can be the same as $Z^1$, $Z^2$, $Z^3$, $Z^4$, $R^1$, $R^2$, $R^3$, $R^5$ and n as described herein for Formula (I). In Scheme 2, $R^6$ can be an optionally substituted $C_{1-6}$ alkyl, an optionally substituted $C_{1-6}$ alkoxyl, an optionally substituted $C_{6-10}$ aryl or an optionally substituted $C_{5-10}$ heteroaryl. In Scheme 2, the compounds can be a racemic mixture of enantiomers or diastereomers. In some embodiments, the compounds can be stereospecific, with carbons 'a', 'b', and 'c' each independently having either an (R) or (S) configuration. The compound of Formula (L) can be a compound of Formula (I), where $R^4$ of Formula (I) is A compound of Formula (G) can be prepared by reacting a compound of Formula (E) with a compound of Formula (F). A compound of Formula (H) can be prepared by removing the t-butyloxycarbonyl (Boc) protecting group from a compound of Formula (G). Suitable deprotection reagents include, but are not limited to, trifluoroacetic acid (TFA), hydrochloric acid, and sulfuric acid. A compound of Formula (K) can be prepared by reacting a compound of Formula (H) with a compound of Formula (J).

A compound of Formula (L) can be prepared by reducing a compound of Formula (K), with H$_2$ such that R$^3$ and R$^5$ are both hydrogen.

Alternatively, a compound of Formula (L) can be prepared by reacting a compound of Formula (K) with OsO$_4$ or KMnO$_4$, such that R$^3$ and R$^5$ are both hydroxyl. In some embodiments, reacting a compound of Formula (K) with OsO$_4$ or KMnO$_4$ can result in isolating a compound of Formula (L) having an (R,R) configuration about carbons 'b' and 'c', respectively. In some embodiments, reacting a compound of Formula (K) with OsO$_4$ or KMnO$_4$ can result in isolating a compound of Formula (L) having an (S,S) configuration about carbons 'b' and 'c', respectively. For example, reacting a compound of Formula (K) with OsO$_4$ in the presence of hydroquinine 1,4-phthalazinediyl diether ((DHQ)$_2$PHAL), K$_3$Fe(CN)$_6$, and MeSO$_2$NH$_2$ can result in syn addition about the carbon-carbon double bond.

In some embodiments, reacting a compound of Formula (K) with OsO$_4$ can result in isolating a compound of Formula (L) having an (R,S) configuration about carbons 'b' and 'c', respectively. In some embodiments, reacting a compound of Formula (K) with OsO$_4$ can result in isolating a compound of Formula (L) having an (S,R) configuration about carbons 'b' and 'c', respectively. For example, reacting a compound of Formula (K) with OsO$_4$ in the presence of N-methylmorpholine-N-oxide (NMO) followed by treatment with NaHSO$_3$ can result in anti addition about the carbon-carbon double bond.

A compound of Formula (M) can be prepared by hydrolyzing a compound of Formula (L). Suitable hydrolyzing reagents include, but are not limited to, NaOH, KOH, LiOH, KHCO$_3$, H$_2$SO$_4$, and HCl.

Scheme 3

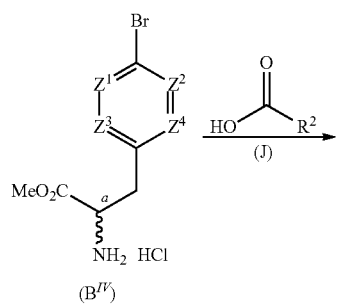

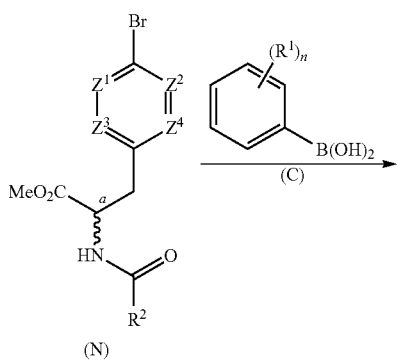

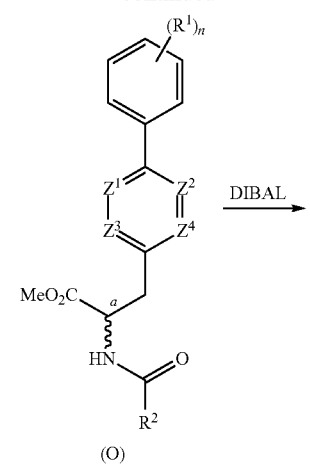

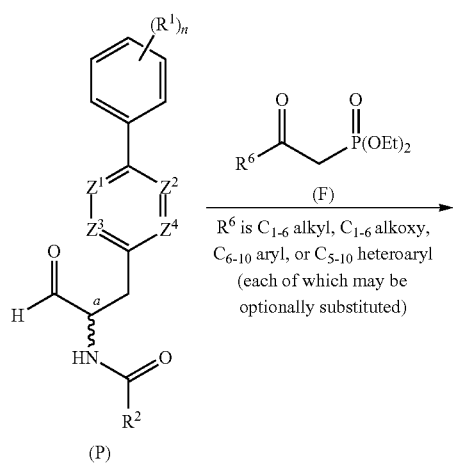

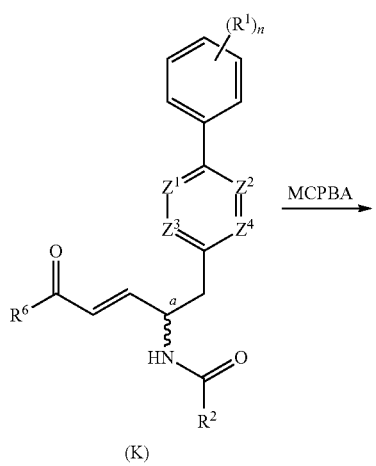

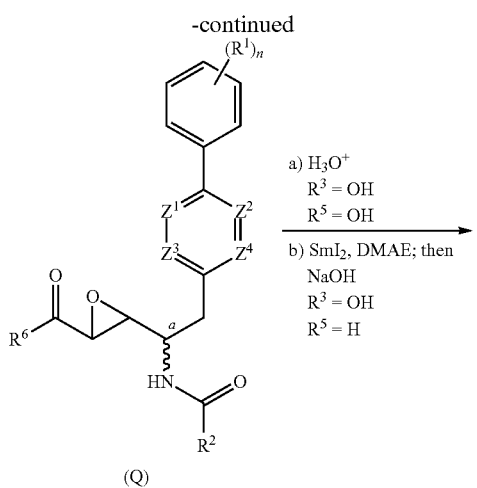

(Q)

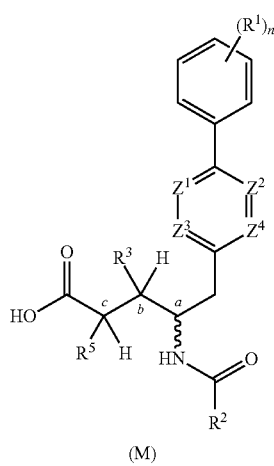

(M)

Some methods for preparing a compound of Formula (M) are shown in Scheme 3. In Scheme 3, $Z^1$, $Z^2$, $Z^3$, $Z^4$, $R^1$, $R^2$, $R^3$, $R^5$ and n can be the same as $Z^1$, $Z^2$, $Z^3$, $Z^4$, $R^1$, $R^2$, $R^3$, $R^5$ and n as described herein for Formula (I). In Scheme 3, $R^6$ can be an optionally substituted $C_{1-6}$ alkyl, an optionally substituted $C_{1-6}$ alkoxyl, an optionally substituted $C_{6-10}$ aryl or an optionally substituted $C_{5-10}$ heteroaryl. In Scheme 3, the compounds can be a racemic mixture of enantiomers or diastereomers. In some embodiments, the compounds can be stereospecific, with carbons 'a', 'b', and 'c' each independently having either an (R) or (S) configuration. The compound of Formula (M) can be a compound of Formula (I), where $R^4$ of Formula (I) is

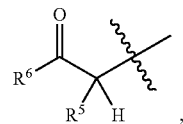

and $R^6$ is —OH.

A compound of Formula (N) can be prepared by reacting a compound of Formula ($B^{IV}$) with a compound of Formula (J). A compound of Formula (O) can be prepared by reacting a compound of Formula (N) with a compound of Formula (C). The reaction of a compound of Formula (N) with a compound of Formula (C) results in inversion of the stereochemistry about carbon 'a'.

A compound of Formula (P) can be prepared by reducing a compound of Formula (O). Suitable reducing agents include, but are not limited to, diisobutylaluminium hydride (DIBAL), lithium aluminium hydride (LiAlH$_4$), and sodium borohydride (NaBH$_4$). A compound of Formula (K) can be prepared by reacting a compound of Formula (P) with a compound of Formula (F). A compound of Formula (O) can be prepared by epoxidation of a compound of Formula (K). Suitable epoxidation reagents include, but are not limited to, a peroxyacid (e.g. meta-chloroperoxybenzoic acid (MCPBA), hydrogen peroxide, and alkyl hydroperoxides (e.g. t-butyl hydroperoxide, and ethylbenzene hydroperoxide).

A compound of Formula (M) can be prepared by reacting of a compound of Formula (O) with aqueous acid, such that $R^3$ and $R^5$ are both hydroxy. In some embodiments, reacting a compound of Formula (O) with aqueous acid can result in isolating a compound of Formula (M) having an (R,S) configuration about carbons 'b' and 'c', respectively. In some embodiments, reacting a compound of Formula (O) with aqueous acid can result in isolating a compound of Formula (M) having an (S,R) configuration about carbons 'b' and 'c', respectively.

Alternatively, a compound of Formula (M) can be prepared by reacting a compound of Formula (Q) with SmI$_2$ and dimethylethanolamine (DMAE), followed by NaOH, such that $R^3$ is hydroxyl and $R^5$ is hydrogen. In some embodiments, reacting a compound of Formula (Q) with SmI$_2$ and dimethylethanolamine (DMAE), followed by NaOH can result in isolating a compound of Formula (M) having an (R) configuration about carbon 'b'. In some embodiments, reacting a compound of Formula (Q) with SmI$_2$ and dimethylethanolamine (DMAE), followed by NaOH can result in isolating a compound of Formula (M) having an (S) configuration about carbon 'b'.

Scheme 4

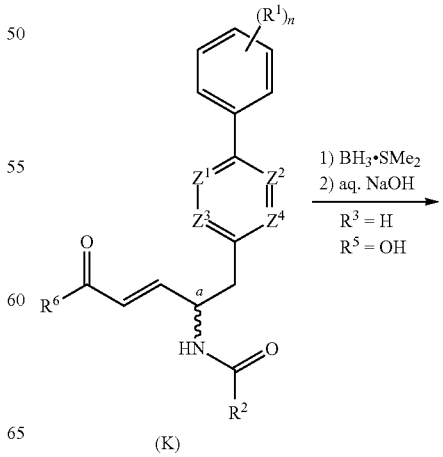

(K)

-continued

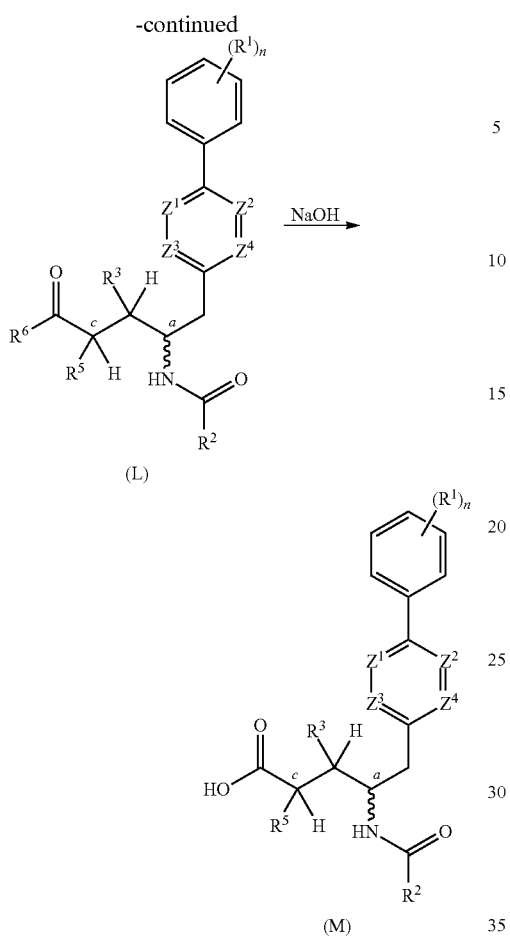

One method for preparing a compound of Formula (L) or (M) is shown in Scheme 4. In Scheme 4, $Z^1$, $Z^2$, $Z^3$, $Z^4$, $R^1$, $R^2$, $R^3$, $R^5$ and n can be the same as $Z^1$, $Z^2$, $Z^3$, $Z^4$, $R^1$, $R^2$, $R^3$, $R^5$ and n as described herein for Formula (I). In Scheme 4, $R^6$ can be an optionally substituted $C_{1-6}$ alkyl, an optionally substituted $C_{1-6}$ alkoxyl, an optionally substituted $C_{6-10}$ aryl or an optionally substituted $C_{5-10}$ heteroaryl. In Scheme 4, the compounds can be a racemic mixture of enantiomers or diastereomers. In some embodiments, the compounds can be stereospecific, with carbons 'a' and 'c' each independently having either an (R) or (S) configuration. The compound of Formula (L) can be a compound of Formula (I), where $R^4$ of Formula (I) is A compound of Formula (L) can be prepared by reacting of a compound of Formula (K) with $BH_3.SMe_2$ followed by aqueous NaOH, such that $R^3$ is hydrogen and $R^5$ is hydroxy. In some embodiments, reacting a compound of Formula (L) with $BH_3.SMe_2$ followed by aqueous NaOH can result in isolating a compound of Formula (L) having an (R) configuration about carbon 'c'. In some embodiments, reacting a compound of Formula (L) with $BH_3.SMe_2$ followed by aqueous NaOH can result in isolating a compound of Formula (L) having an (S) configuration about carbon 'c'.

A compound of Formula (M) can be prepared by hydrolyzing a compound of Formula (L). Suitable hydrolyzing reagents include, but are not limited to, NaOH, KOH, LiOH, $KHCO_3$, $H_2SO_4$, and HCl.

Scheme 5

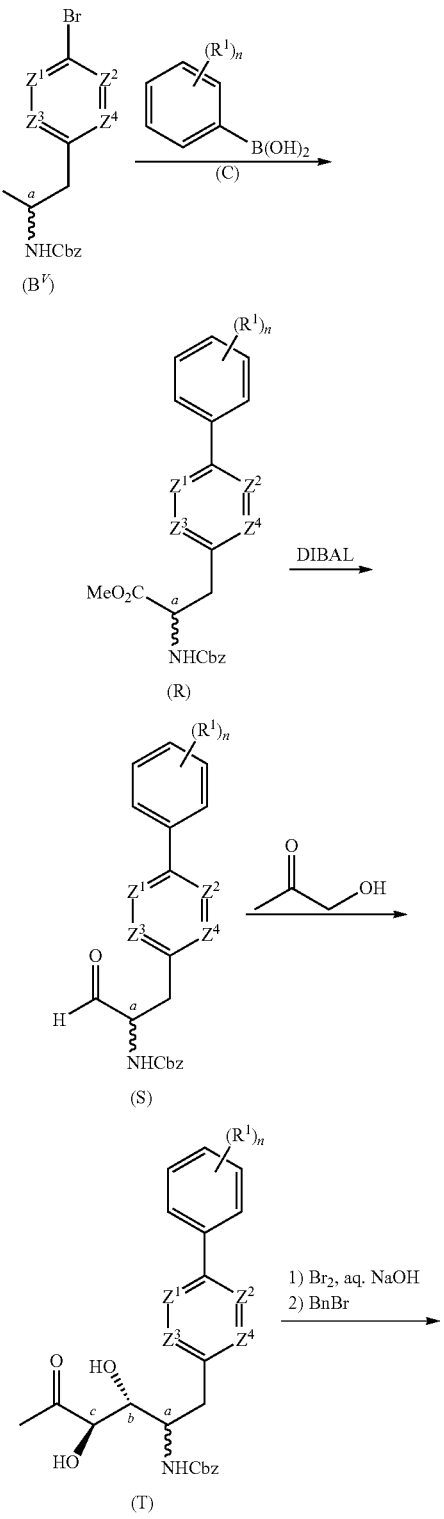

-continued

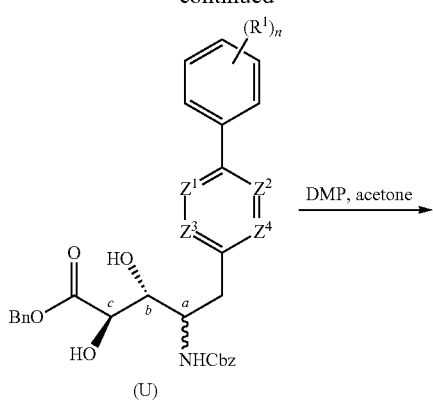

(U)

DMP, acetone →

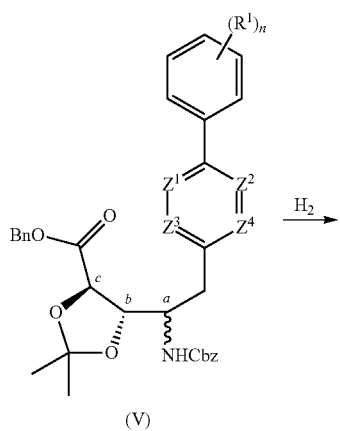

(V)

H₂ →

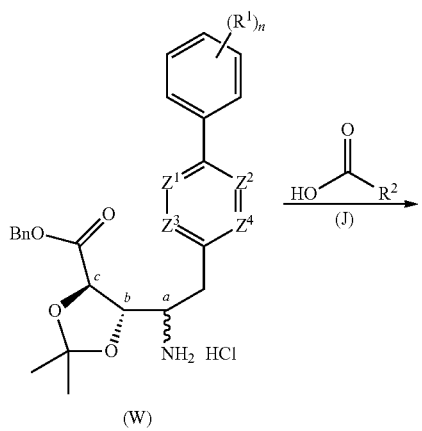

(W)

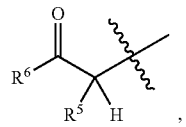
(J)

→

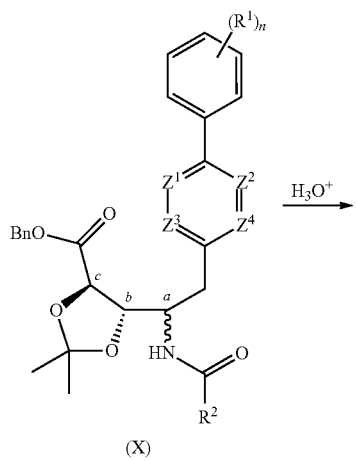

(X)

H₃O⁺ →

-continued

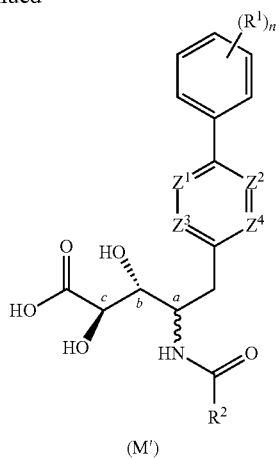

(M')

A method for preparing a compound of Formula (M') is shown in Scheme 5. In Scheme 5, $Z^1$, $Z^2$, $Z^3$, $Z^4$, $R^1$ and n can be the same as $Z^1$, $Z^2$, $Z^3$, $Z^4$, $R^1$ and n as described herein for Formula (I). In Scheme 5, the compounds can be a racemic mixture of enantiomers or diastereomers. In some embodiments, the compounds can be stereospecific, with carbon 'a' having either an (R) or (S) configuration, and carbons 'b' and 'c' having the shown stereochemistry. The compound of Formula (M') can be a compound of Formula (I), where $R^4$ of Formula (I) is and $R^3$, $R^5$, and $R^6$ are each hydroxyl.

A compound of Formula (R) can be prepared by reacting a compound of Formula ($B^V$) with a compound of Formula (C). The reaction of a compound of Formula ($B^V$) with a compound of Formula (C) results in inversion of the stereochemistry about carbon 'a'. A compound of Formula (S) can be prepared by reducing a compound of Formula (R). Suitable reducing agents include, but are not limited to, diisobutylaluminium hydride (DIBAL), lithium aluminium hydride (LiAlH₄), and sodium borohydride (NaBH₄).

A compound of Formula (T) can be prepared by reacting a compound of Formula (S) with 1-hydroxypropan-2-one. A compound of Formula (U) can be prepared by reacting a compound of Formula (T) with Br₂ in aqueous NaOH, followed by treatment with benzyl bromide. A compound of Formula (V) can be prepared by reacting a compound of Formula (U) with 2,2-dimethoxypropane (DMP) in acetone.

A compound of Formula (W) can be prepared by removing the benzyloxycarbonyl (Cbz) protecting group from a compound of Formula (V). Suitable deprotection reagents include, but are not limited to, catalytic hydrogenolysis, KOH, and HBr. A compound of Formula (X) can be prepared by reacting a compound of Formula (W) with a compound of Formula (J). A compound of Formula (M') can be prepared by reacting of a compound of Formula (X) with aqueous acid.

Scheme 6

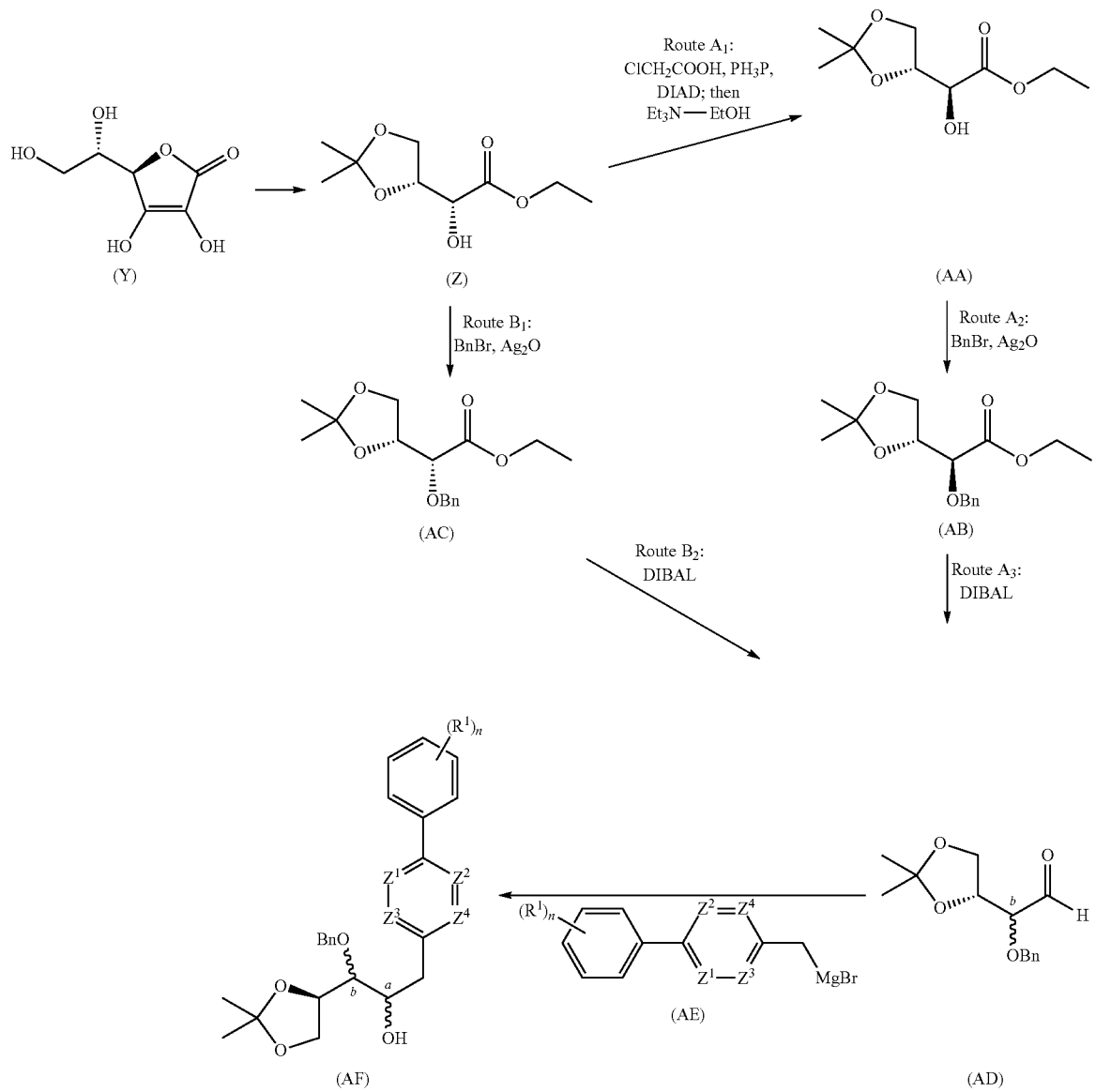

Some methods for preparing a compound of Formula (AF) are shown in Scheme 6. In Scheme 6, $Z^1$, $Z^2$, $Z^3$, $Z^4$, $R^1$ and n can be the same as $Z^1$, $Z^2$, $Z^3$, $Z^4$, $R^1$ and n as described herein for Formula (I). In Scheme 6, the compounds can be a racemic mixture of enantiomers or diastereomers. In some embodiments, the compounds can be stereospecific, with carbons 'a' and 'b' each independently having either an (R) or (S) configuration.

A compound of Formula (Z) can be prepared by reacting a compound of Formula (Y) with $CuSO_4$ in acetone, followed by treatment with $K_2CO_3$ and $H_2O_2$, and followed by treatment with ethyl iodide. A compound of Formula (AA) can be prepared by reacting a compound of Formula (Z) with 2-chloroacetic acid, triphenylphosphine, and diisopropyl azodicarboxylate (DIAD), followed by treatment with triethylamine in ethanol. A compound of Formula (AB) can be prepared by reacting a compound of Formula (AA) with benzyl bromide and silver oxide. A compound of Formula (AD) having (S) stereochemistry at carbon 'b' can be prepared by reducing a compound of Formula (AB). Suitable reducing agents include, but are not limited to, diisobutylaluminium hydride (DIBAL), lithium aluminium hydride ($LiAlH_4$), and sodium borohydride ($NaBH_4$).

A compound of Formula (AC) can be prepared by reacting a compound of Formula (Z) with benzyl bromide and silver oxide. A compound of Formula (AD) having (R) stereochemistry at carbon 'b' can be prepared by reducing a compound of Formula (AC). Suitable reducing agents include, but are not limited to, diisobutylaluminium hydride (DIBAL), lithium aluminium hydride ($LiAlH_4$), and sodium borohydride ($NaBH_4$).

A compound of Formula (AF) can be prepared by reacting a compound of Formula (AD) with a compound of Formula (AE).

47
Scheme 7
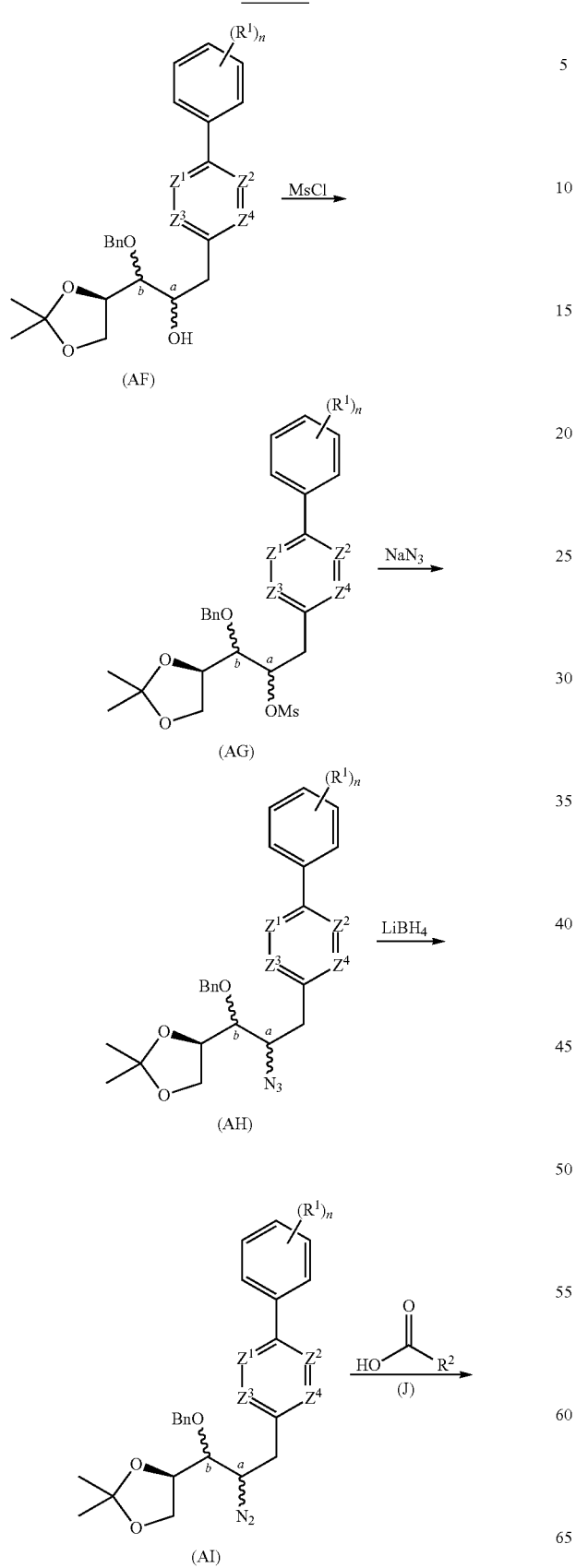
48
-continued
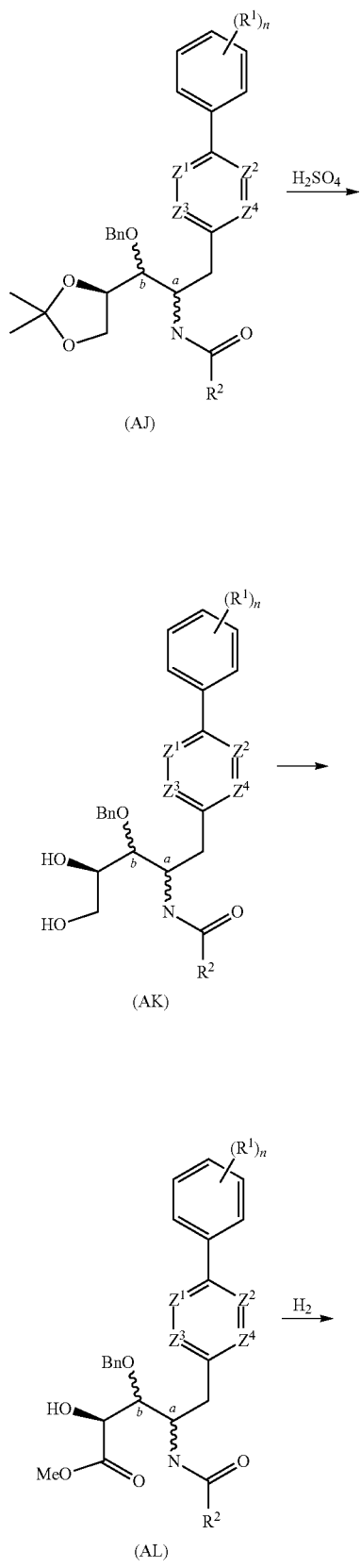

-continued

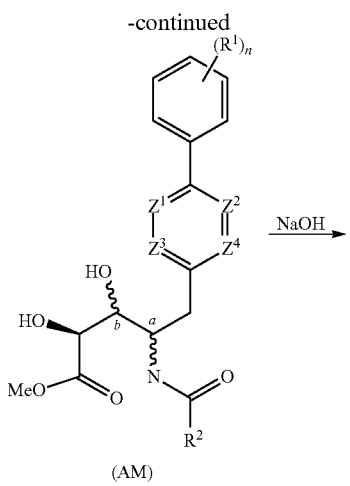

(AM)

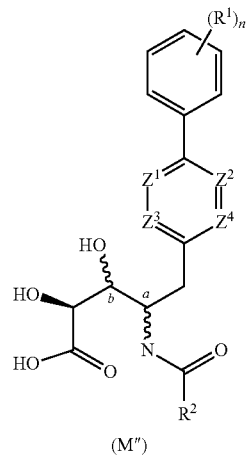

(M")

Methods for preparing a compound of Formula (AM) or (M") are shown in Scheme 7. In Scheme 7, $Z^1$, $Z^2$, $Z^3$, $Z^4$, $R^1$, $R^2$ and n can be the same as $Z^1$, $Z^2$, $Z^3$, $Z^4$, $R^1$, $R^2$ and n as described herein for Formula (I). In Scheme 7, the compounds can be a racemic mixture of enantiomers or diastereomers. In some embodiments, the compounds can be stereospecific, with carbons 'a' and 'b' each independently having either an (R) or (S) configuration. The compound of Formula (AM) can be a compound of Formula (I), where $R^4$ of Formula (I) is

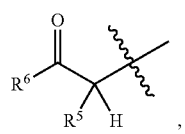

$R^3$ and $R^5$ are each hydroxyl, and $R^6$ is methoxy. The compound of Formula (M") can be a compound of Formula (I), where $R^4$ of Formula (I) is

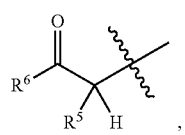

and $R^3$, $R^5$ and $R^6$ are each hydroxy.

A compound of Formula (AG) can be prepared by reacting a compound of Formula (AF) with methanesulfonyl chloride (MsCl). A compound of Formula (AH) can be prepared by reacting a compound of Formula (AG) with sodium azide. A compound of Formula (AI) can be prepared by reducing a compound of Formula (AH) with a reducing agent such as $LiBH_4$. A compound of Formula (AJ) can be prepared by reacting a compound of Formula (AI) with a compound of Formula (J).

A compound of Formula (AK) can be prepared by removing the acetonide protecting group from a compound of Formula (AJ). Suitable deprotection reagents include, but are not limited to, $H_2SO_4$, HCl, acetic acid, trifluoroacetic acid, and cation exchange resins. A compound of Formula (AL) can be prepared by reacting a compound of Formula (AK) with 2,2,6,6-tetramethylpiperidine 1-oxyl (TEMPO), N-chlorosuccinimide (NCS), and tetrabuylammonium chloride (TBACl), followed by treatment with $NaClO_2$, $NaH_2PO_4$, and $H_2O_2$, followed by treatment with $CH_2N_2$.

A compound of Formula (AM) can be prepared by removing the benzyl protecting group from a compound of Formula (AL). Suitable deprotection conditions include, for example, catalytic hydrogenolysis. A compound of Formula (M") can be prepared by hydrolyzing a compound of Formula (AM). Suitable hydrolyzing reagents include, but are not limited to, NaOH, KOH, LiOH, $KHCO_3$, $H_2SO_4$, and HCl.

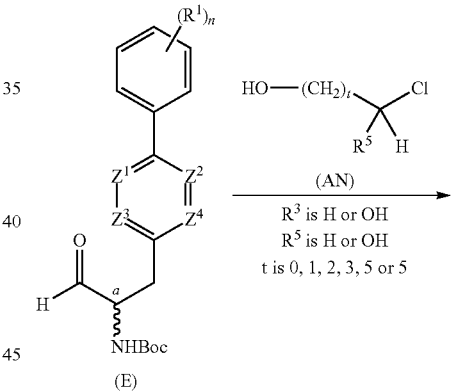

(E) → (AN) $R^3$ is H or OH, $R^5$ is H or OH, t is 0, 1, 2, 3, 5 or 5

(AO) TFA

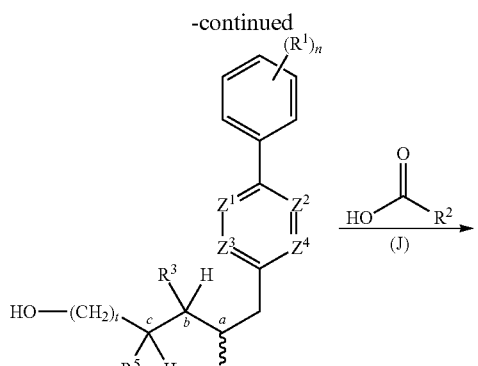

Methods for preparing a compound of Formula (AQ) are shown in Scheme 8. In Scheme 8, $Z^1$, $Z^2$, $Z^3$, $Z^4$, $R^1$, $R^2$, $R^3$, $R^5$, n and t can be the same as $Z^1$, $Z^2$, $Z^3$, $Z^4$, $R^1$, $R^2$, $R^3$, $R^5$, n and t as described herein for Formula (I). In Scheme 8, the compounds can be a racemic mixture of enantiomers or diastereomers. In some embodiments, the compounds can be stereospecific, with carbons 'a', 'b' and 'c' each independently having either an (R) or (S) configuration. The compound of Formula (AQ) can be a compound of Formula (I), where $R^4$ of Formula (I) is

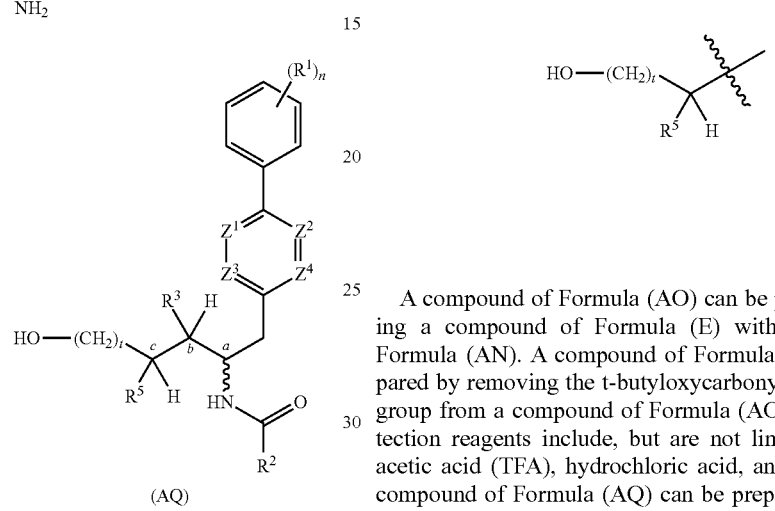

A compound of Formula (AO) can be prepared by reacting a compound of Formula (E) with a compound of Formula (AN). A compound of Formula (AP) can be prepared by removing the t-butyloxycarbonyl (Boc) protecting group from a compound of Formula (AO). Suitable deprotection reagents include, but are not limited to, trifluoroacetic acid (TFA), hydrochloric acid, and sulfuric acid. A compound of Formula (AQ) can be prepared by reacting a compound of Formula (AP) with a compound of Formula (J).

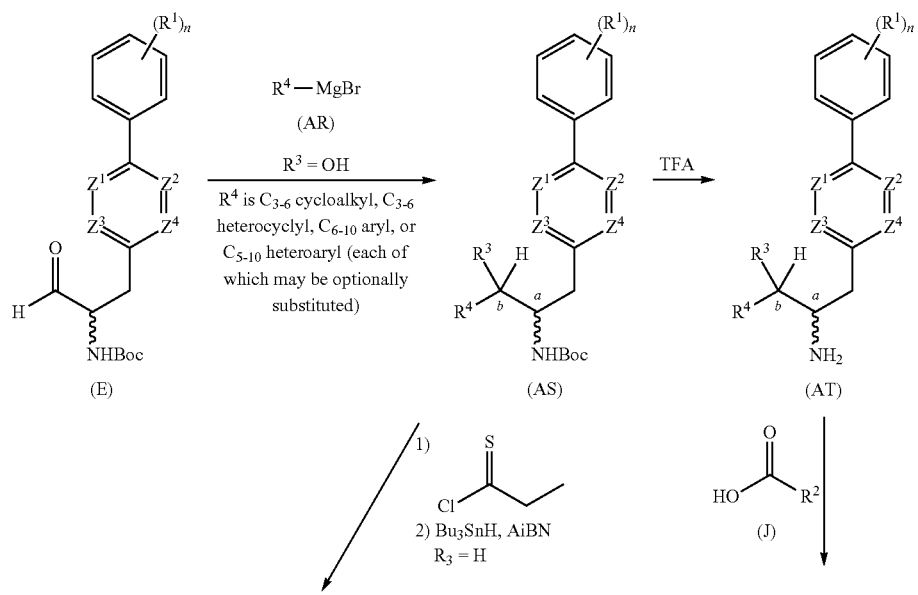

-continued

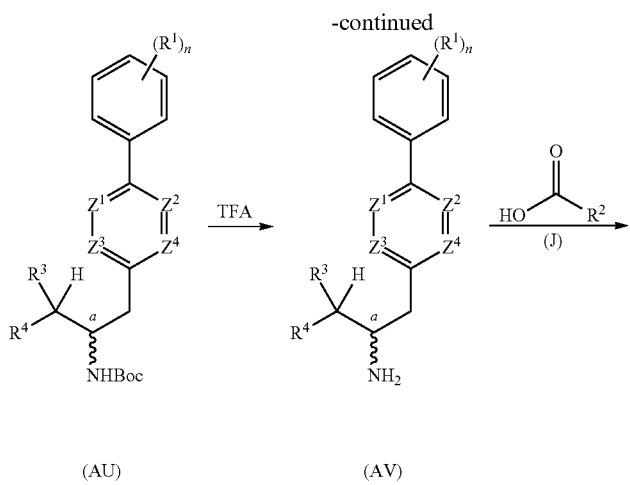
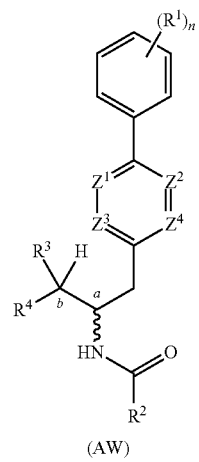

Methods for preparing a compound of Formula (AW) are shown in Scheme 9. In Scheme 9, $Z^1$, $Z^2$, $Z^3$, $Z^4$, $R^1$, $R^2$, $R^3$, $R^4$ and n can be the same as $Z^1$, $Z^2$, $Z^3$, $Z^4$, $R^1$, $R^2$, $R^3$, $R^4$ and n as described herein for Formula (I). In Scheme 9, the compounds can be a racemic mixture of enantiomers or diastereomers. In some embodiments, the compounds can be stereospecific, with carbons 'a' and 'b' each independently having either an (R) or (S) configuration. The compound of Formula (AW) can be a compound of Formula (I), where $R^4$ of Formula (I) is an optionally substituted $C_{3-6}$ cycloalkyl, an optionally substituted $C_{3-6}$ heterocyclyl, an optionally substituted $C_{6-10}$ aryl, or an optionally substituted $C_{5-10}$ heteroaryl.

A compound of Formula (AS) where $R^3$ is hydroxyl can be prepared by reacting a compound of Formula (E) with a compound of Formula (AR). A compound of Formula (AT) where $R^3$ is hydroxyl can be prepared by removing the t-butyloxycarbonyl (Boc) protecting group from a compound of Formula (AS). Suitable deprotection reagents include, but are not limited to, trifluoroacetic acid (TFA), hydrochloric acid, and sulfuric acid. A compound of Formula (AW) where $R^3$ is hydroxyl can be prepared by reacting a compound of Formula (AT) with a compound of Formula (J).

A compound of Formula (AU) where $R^3$ is hydrogen can be prepared by subjecting a compound of Formula (AS) to Barton-McCombie conditions, such as propanethioyl chloride followed by azobis-isobutyronitrile (AiBN) and tributyltin hydride. A compound of Formula (AV) where $R^3$ is hydrogen can be prepared by removing the t-butyloxycarbonyl (Boc) protecting group from a compound of Formula (AU). Suitable deprotection reagents include, but are not limited to, trifluoroacetic acid (TFA), hydrochloric acid, and sulfuric acid. A compound of Formula (AW) where $R^3$ is hydrogen can be prepared by reacting a compound of Formula (AV) with a compound of Formula (J).

Scheme 10

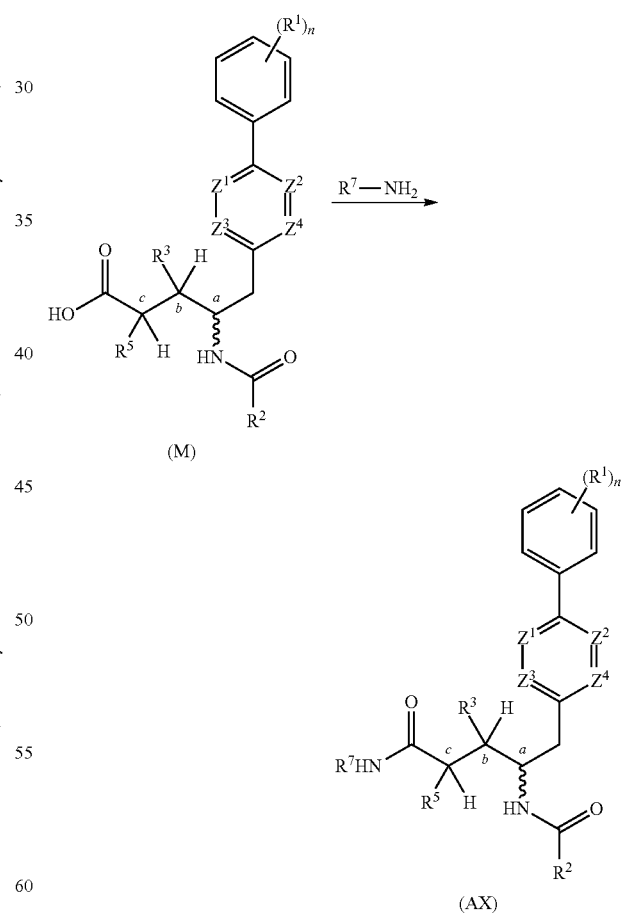

Methods for preparing a compound of Formula (AX) are shown in Scheme 10. In Scheme 10, $Z^1$, $Z^2$, $Z^3$, $Z^4$, $R^1$, $R^2$, $R^3$, $R^5$, $R^7$ and n can be the same as $Z^1$, $Z^2$, $Z^3$, $Z^4$, $R^1$, $R^2$, $R^3$, $R^5$, $R^7$ and n as described herein for Formula (I). In Scheme 10, the compounds can be a racemic mixture of enantiomers or diastereomers. In some embodiments, the compounds can be stereospecific, with carbons 'a', 'b' and 'c' each independently having either an (R) or (S) configuration. The compound of Formula (AX) can be a compound of Formula (I), where $R^4$ of Formula (I) is

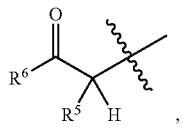

and $R^6$ is —$NHR^7$. As shown in Scheme 10, a compound of Formula (AX) can be prepared by reacting a compound of Formula (M) with $R^7$—$NH_2$.

VII. Pharmaceutical Compositions

Some embodiments described herein relate to a pharmaceutical composition that can include a therapeutically effective amount of one or more compounds described herein (e.g., a compound of Formulae (I), or a pharmaceutically acceptable salt thereof) and a pharmaceutically acceptable carrier, diluent, excipient or combination thereof. Acceptable carriers and diluents for therapeutic use are well known in the pharmaceutical art, and are described, for example, in Remington's Pharmaceutical Sciences, Mack Publishing Co. (A. R. Gennaro edit. 1985), the disclosure of which is incorporated herein by reference in its entirety. A carrier can facilitate the incorporation of a compound into cells or tissues. For example, without limitation, dimethyl sulfoxide (DMSO) is a commonly utilized carrier that facilitates the uptake of many organic compounds into cells or tissues of a subject. A diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood. Preservatives, stabilizers, dyes and even flavoring agents may be provided in the pharmaceutical composition. For example, sodium benzoate, ascorbic acid and esters of p-hydroxybenzoic acid may be added as preservatives. In addition, antioxidants and suspending agents may be used.

In some embodiments, the pharmaceutical composition can include a single diastereomer of a compound of Formula (I)-(VI) (which can include a compound of Formula (Ia), (Ib), (Ic), or (Id)), or a pharmaceutically acceptable salt thereof, (for example, a single diastereomer is present in the pharmaceutical composition at a concentration of greater than 99% compared to the total concentration of the other diastereomers). In other embodiments, the pharmaceutical composition can include a mixture of diastereomers of a compound of Formula (I), or a pharmaceutically acceptable salt thereof. For example, the pharmaceutical composition can include a concentration of one diastereomer of >50%, ≥60%, ≥70%, ≥80%, ≥90%, ≥95%, or ≥98%, as compared to the total concentration of the other diastereomers. In some embodiments, the pharmaceutical composition includes a 1:1 mixture of two diastereomers of a compound of Formula (I), or a pharmaceutically acceptable salt thereof.

A pharmaceutical composition can facilitate administration of one or more compounds described herein to an organism. Pharmaceutical compositions can be obtained by reacting compounds described herein with inorganic or organic acids such as hydrochloric acid, hydrobromic acid, sulfuric acid, nitric acid, phosphoric acid, methanesulfonic acid, ethanesulfonic acid, p-toluenesulfonic acid and salicylic acid. Pharmaceutical compositions will generally be tailored to the specific intended route of administration.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The compounds and compositions disclosed herein may be formulated and used as tablets, capsules, or elixirs for oral administration; suppositories for rectal administration; sterile solutions, suspensions for injectable administration; patches for transdermal administration, and sub-dermal deposits and the like. Injectables can be prepared in conventional forms, either as liquid solutions or suspensions, solid forms suitable for solution or suspension in liquid prior to injection or infusion, or as emulsions. Suitable excipients are, for example, water, saline, dextrose, mannitol, lactose, lecithin, albumin, sodium glutamate, cysteine hydrochloride, human serum albumin and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), may be utilized.

Pharmaceutical formulations for parenteral administration include aqueous solutions of the compounds in water-soluble form. Additionally, suspensions of the compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use may be obtained by combining the compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. Such formulations can be made using methods known in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes will be targeted to and taken up selectively by the organ.

The compounds or compositions may, if desired, be presented in a package or dispenser device which may contain one or more unit dosage forms containing the active ingredient. The compound or composition described herein can be packaged alone, or can be packaged with another compound or another ingredient or additive. The package can contain one or more containers filled with one or more of the ingredients of the pharmaceutical compositions. The package may for example comprise metal or plastic foil, such as a blister pack. The package or dispenser device may be accompanied by instructions for administration, such as instructions for administering the compounds or compositions for treating a neoplastic disease. The package or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

VIII. Methods of Use

Some embodiments disclosed herein relate to a method of treating and/or ameliorating a disease or condition that can include administering to a subject a therapeutically effective amount of one or more compounds described herein, such as a compound of Formula (I)-(VI) (which can include a compound of Formula (Ia), (Ib), (Ic), or (Id)), or a pharmaceutically acceptable salt thereof, or a pharmaceutical composition that includes a compound described herein. In some embodiments, the disease or condition can be a neoplastic disease, an age-related disease, a neurological disease, an immunological disease, or an infectious disease. In an embodiment, the neoplastic disease can be cancer. In some embodiments, the cancer can be B-cell related cancers. In some embodiments, the neoplastic disease can be a tumor such as a solid tumor. In some embodiments, the cancer can be melanoma. In some embodiments, the cancer can be, breast cancer or pancreatic cancer. In some embodiments, the cancer can be multiple myeloma. In some embodiments, the cancer can be non-Hodgkin's lymphoma. In some embodiment, the cancer can be T cell acute lympho-blastic leukemia. In some embodiments, the cancer can be mantel cell lymphoma. In some embodiments, the tumor can be glioma. In some embodiments, the specific diseases described herein (e.g., melanoma, breast cancer, pancreatic cancer, multiple myeloma, non-Hodgkin's lymphoma, T cell acute lympho-blastic leukemia, mantel cell lymphoma or glioma) can be ameliorated by a compound of Formula (I)-(VI) (which can include a compound of Formula (Ia), (Ib), (Ic), or (Id)), or a pharmaceutically acceptable salt thereof, or a pharmaceutical composition that includes a compound described herein through inhibiting the ubiquitin-proteasome system. In some embodiments, the cancer can be a type with low levels of let-7 microRNA expression, such as lung, colon or breast cancer.

Some embodiments disclosed herein relates to a method for inhibiting the ubiquitin-proteasome system in a subject that can include administering to a subject a therapeutically effective amount of one or more compounds described herein, such as a compound of Formula (I)-(VI) (which can include a compound of Formula (Ia), (Ib), (Ic), or (Id)), or a pharmaceutically acceptable salt thereof, or a pharmaceutical composition that includes a compound described herein to inhibit the ubiquitin-proteasome system in said subject.

Some embodiments disclosed herein relates to a method for inhibiting Cdc34 in a subject that can include administering to a subject a therapeutically effective amount of one or more compounds described herein, such as a compound of Formula (I)-(VI) (which can include a compound of Formula (Ia), (Ib), (Ic), or (Id)), or a pharmaceutically acceptable salt thereof, or a pharmaceutical composition that includes a compound described herein to inhibit Cdc34 in said subject. In one embodiment, Cdc34 can be hCdc34.

Some embodiments disclosed herein relate to a method for inhibiting cellular proliferation in a subject that can include administering to the subject a therapeutically effective amount of one or more compounds compound described herein, such as a compound of Formula (I)-(VI) (which can include a compound of Formula (Ia), (Ib), (Ic), or (Id)), or a pharmaceutically acceptable salt thereof, or a pharmaceutical composition thereof that includes a compound described herein to inhibit cellular proliferation in said subject.

Some embodiments disclosed herein relate to a method for identifying a candidate therapeutic compound that can include determining the effective amount of a compound described herein, such as a compound of Formula (I)-(VI) (which can include a compound of Formula (Ia), (Ib), (Ic), or (Id)), on the extent of ubiquitination of $p27^{Kip1}$ by a $SCF^{Skp2}$ E3 complex, wherein said compound is identified as a candidate therapeutic compound if said compound significantly reduces said extent of ubiquitination.

Some embodiments disclosed herein relate to a method for determining the effect of a candidate therapeutic compound include determining the effective amount of a compound described herein, such as a compound of Formula (I)-(VI) (which can include a compound of Formula (Ia), (Ib), (Ic), or (Id)), on the extent of ubiquitin chain initiation or ubiquitin chain length, wherein said compound is identified as a candidate therapeutic compound if said compound significantly reduces said extent of ubiquitin chain initiation or ubiquitin chain length.

Some embodiments disclosed herein relate to a method for determining the effect of a candidate therapeutic compound that can include determining the effective amount of a compound described herein, such as a compound of Formula (I)-(VI) (which can include a compound of Formula (Ia), (Ib), (Ic), or (Id)), on the extent of cellular proliferation, wherein said compound is identified as a candidate therapeutic compound if said compound significantly reduces said extent of cellular proliferation.

Some embodiments disclosed herein relate to a method of ameliorating or treating a neoplastic disease that can include administering to a subject suffering from a neoplastic disease a therapeutically effective amount of one or more compounds described herein (e.g., a compound of Formula (I)-(VI) (which can include a compound of Formula (Ia), (Ib), (Ic), or (Id)), or a pharmaceutically acceptable salt thereof, or a pharmaceutical composition that includes a compound described herein). In an embodiment, the neoplastic disease can be cancer. In some embodiments, the neoplastic disease can be a tumor such as a solid tumor. In some embodiments, the cancer can be melanoma, breast cancer or pancreatic cancer. In some embodiments, the cancer can be multiple myeloma. In some embodiments, the cancer can be non-Hodgkin's lymphoma. In some embodiments, the cancer can be T cell acute lympho-blastic leukemia. In some embodiments, the cancer can be a type with low levels of let-7 microRNA expression such as lung, colon or breast cancer. Some studies have suggested that Cdc34 protein levels can be strongly down-regulated by let-7 overexpression. Reporter assays has demonstrated direct regulation of the cdc34 3'-untranslated region by let-7. See, Legesse-Miller et al, "let-7 Overexpression leads to an increased fraction of cells in G2/M, direct down-regulation of Cdc34, and stabilization of Wee1 kinase in primary fibroblasts," J. Biol. Chem. 2009, 284(11):6605-6609.

Some embodiments disclosed herein relate to a method of inhibiting the growth of a tumor that can include administering to a subject having a tumor a therapeutically effective amount of one or more compounds described herein (for example, a compound of Formula (I)), or a pharmaceutical composition that includes one or more compounds described herein. In some embodiments, the tumor can be glioma.

In any of the method of treatment described herein by administration of a compound of Formula (I)-(VI) (which can include a compound of Formula (Ia), (Ib), (Ic), or (Id)) described herein, the method may further comprise administering at least one additional therapeutic agent in addition to the compounds of Formula (I)-(VI) (which can include a compound of Formula (Ia), (Ib), (Ic), or (Id)). In some embodiments, the additional therapeutic agent is bortezomib (Velcade®). Velcade® is the first proteasome inhibitor to reach clinical use as a chemotherapy agent. Bortezomib is used in the treatment of multiple myeloma. In some embodiments, the additional therapeutic agent is ritonavir. Ritonovir has been shown to inhibit proteasomes as well as free proteases. Some studies indicate that ritonavir may have inhibitory effects on the growth of glioma cells. In some embodiment, the additional therapeutic agent is cisplatin. It has been reported that cisplatin increased ATF5 protein expression via preventing its ubiquitin-dependent degradation, which might be associated with its promoting the nucleus-to-cytoplasm translocation of E2 ubiquitin-conjugating enzyme Cdc34 and reducing the interaction between ATF5 and Cdc34. A down-regulation of proteasome-mediated degradation of ATF5 might contribute to cisplatin-induced apoptosis, providing a new mechanism of cisplatin-induced apoptosis. See, Wei et al. "Cdc34-mediated degradation of ATF5 is blocked by cisplatin," J. Biol. Chem. 2008, 283(27):18773-81.

A therapeutically effective amount of a compound disclosed herein can prevent, alleviate or ameliorate symptoms of disease or prolong the survival of the subject being treated. This response may occur in a tissue, system, animal or human and includes alleviation of the signs or symptoms of the disease being treated. Determination of a therapeutically effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years. In some embodiments, a compound of Formula (I), or a pharmaceutically acceptable salt thereof, can be administered less frequently compared to the frequency of administration of an agent within the standard of care. In some embodiments, a compound of Formula (I), or a pharmaceutically acceptable salt thereof, can be administered one time per day. For example, a compound of Formula (I), or a pharmaceutically acceptable salt thereof, can be administered one time per day to a subject suffering from a neoplastic disease. In some embodiments, the total time of the treatment regime with a compound of Formula (I), or a pharmaceutically acceptable salt thereof, can less compared to the total time of the treatment regime with the standard of care.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

The exact formulation, route of administration and dosage can be chosen by the individual physician in view of the patient's condition. See for example, Fingl et al., in The Pharmacological Basis of Therapeutics, 1975, the disclosure of which is incorporated herein by reference in its entirety. It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. Determination of the effective amount of a compound disclosed herein is well within the capability of those skilled in the art. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

EXAMPLES

Additional embodiments are disclosed in further detail in the following examples, which are not in any way intended to limit the scope of the claims.

Example 1

The following compounds can be prepared according to the reaction conditions shown below.

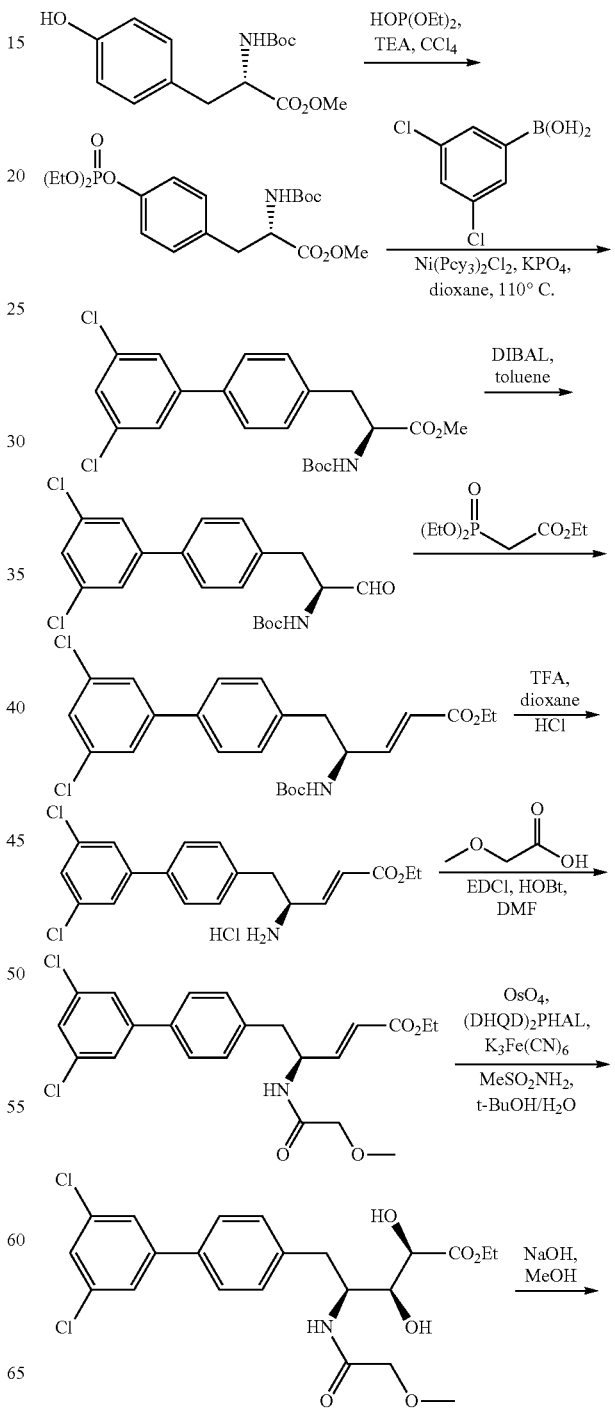

63
-continued
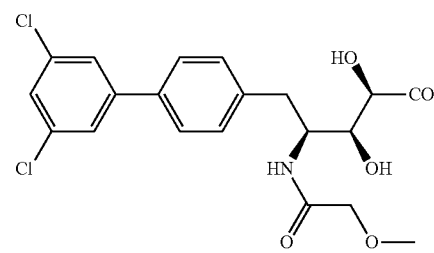
Example 2
The following compounds can be prepared according to the reaction conditions shown below.
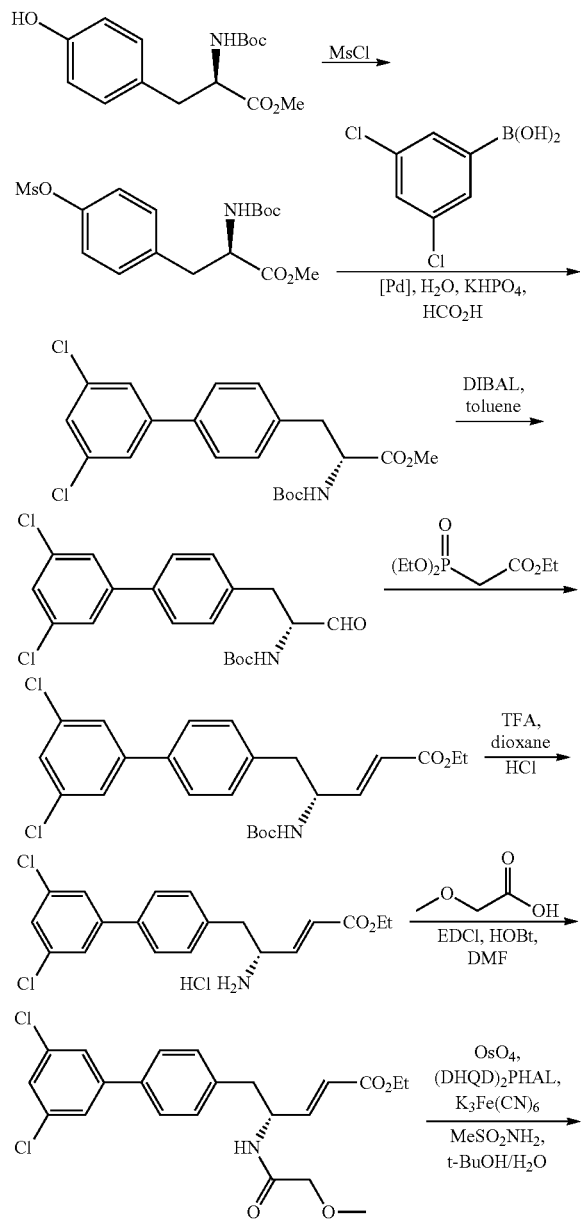
64
-continued
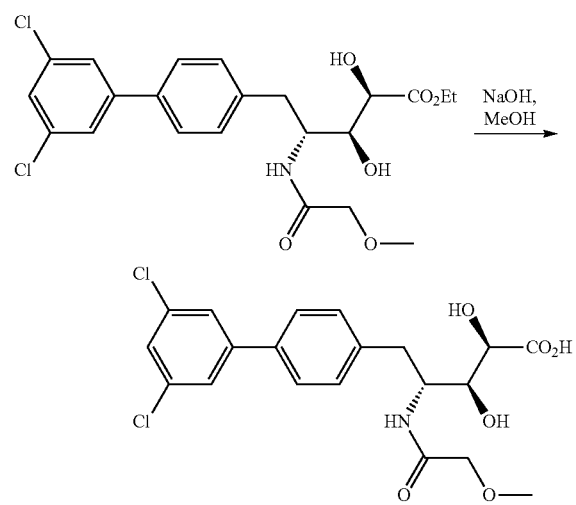
Example 3
The following compounds can be prepared according to the reaction conditions shown below.
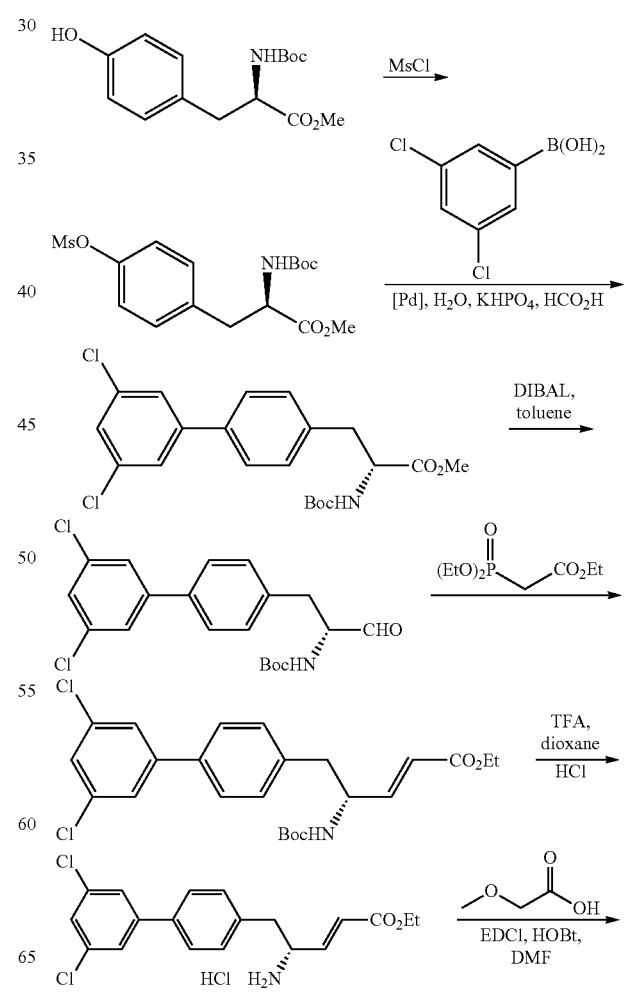

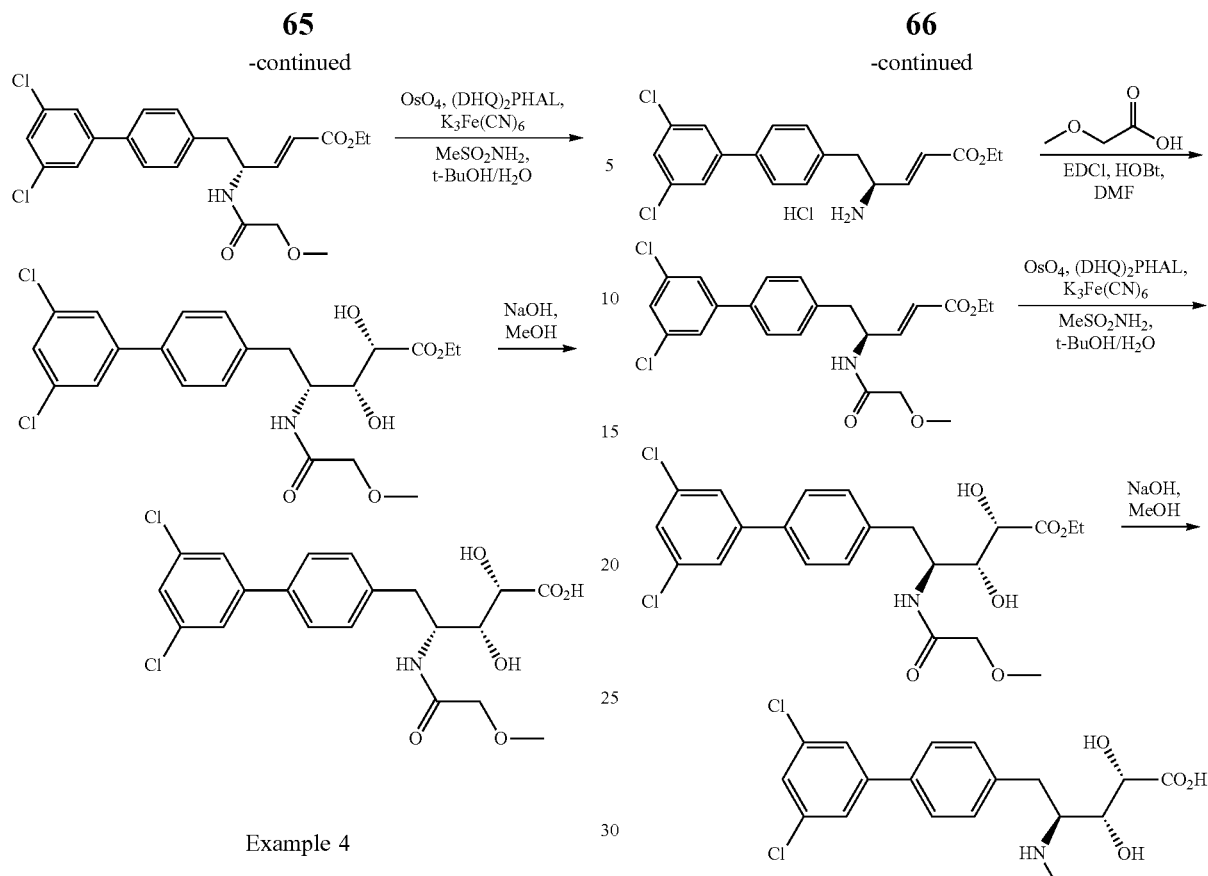
Example 4
The following compounds can be prepared according to the reaction conditions shown below.
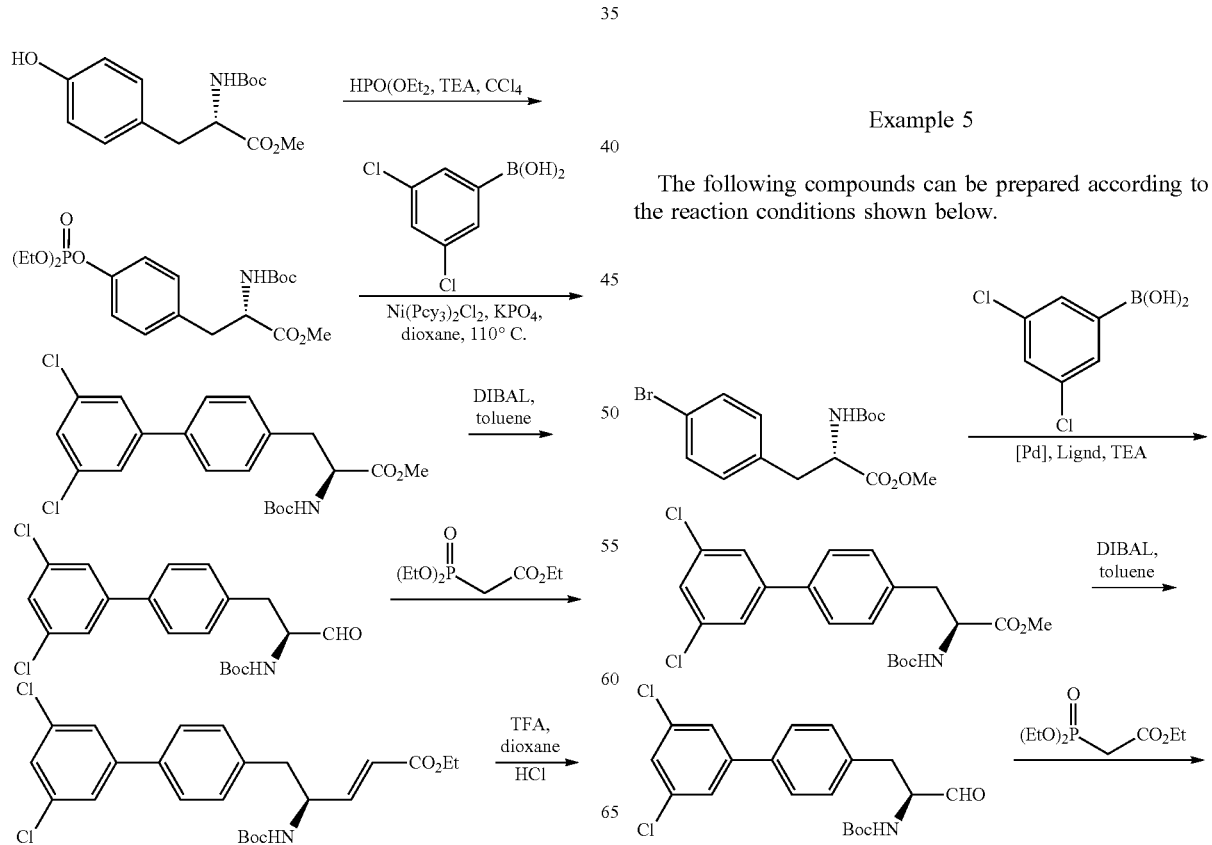
Example 5
The following compounds can be prepared according to the reaction conditions shown below.

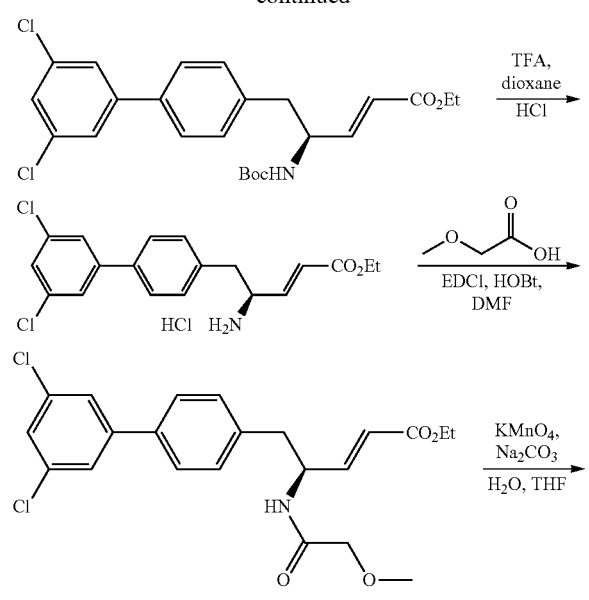
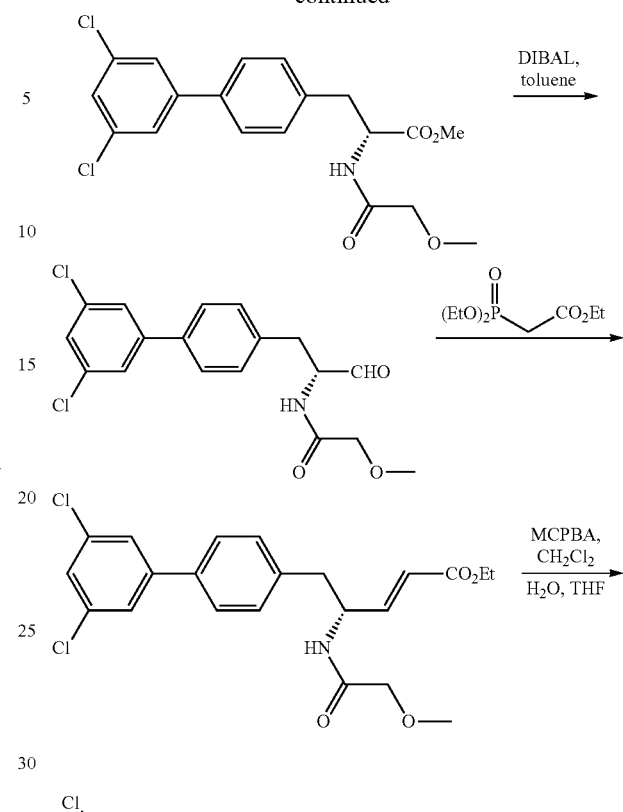
Example 6
The following compounds can be prepared according to the reaction conditions shown below.
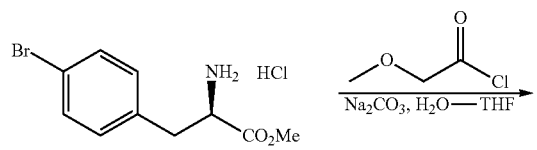
Example 7
The following compounds can be prepared according to the reaction conditions shown below.
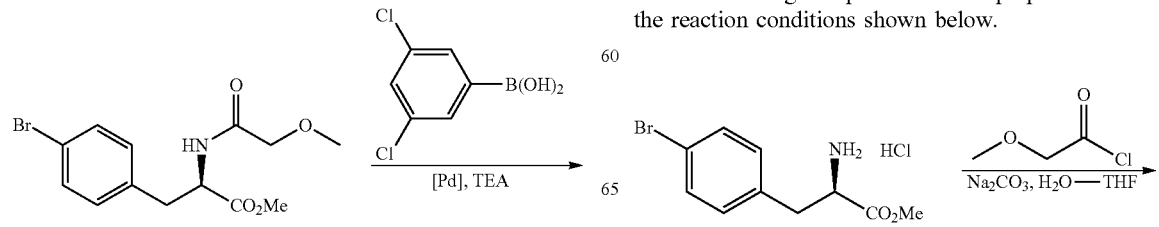

-continued
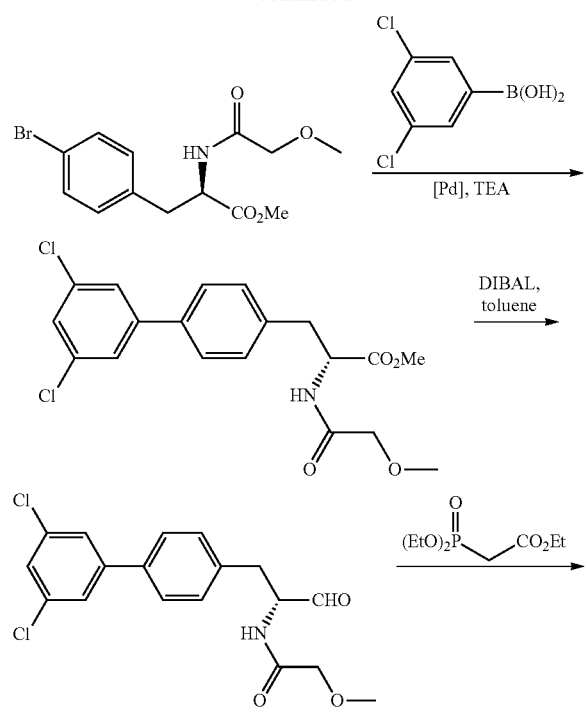
Example 8
The following compounds can be prepared according to the reaction conditions shown below.
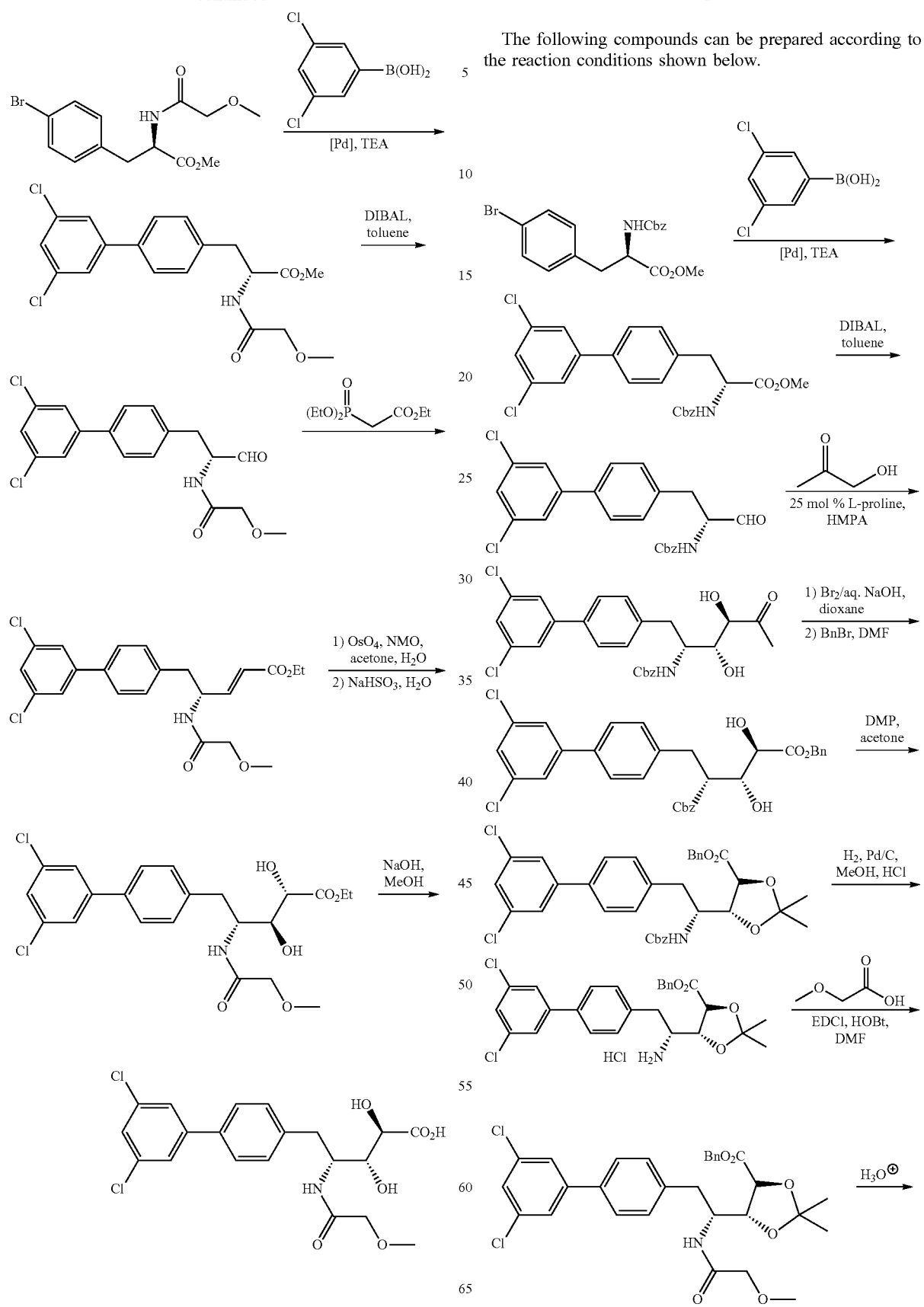

-continued
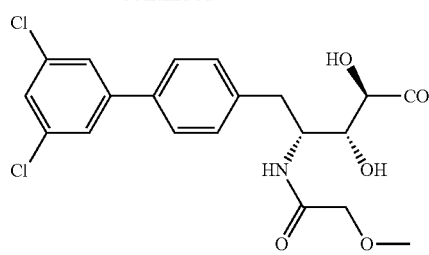
Example 9
The following compounds can be prepared according to the reaction conditions shown below.
-continued
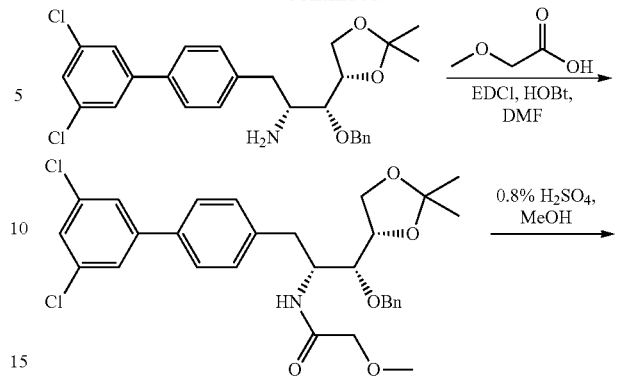
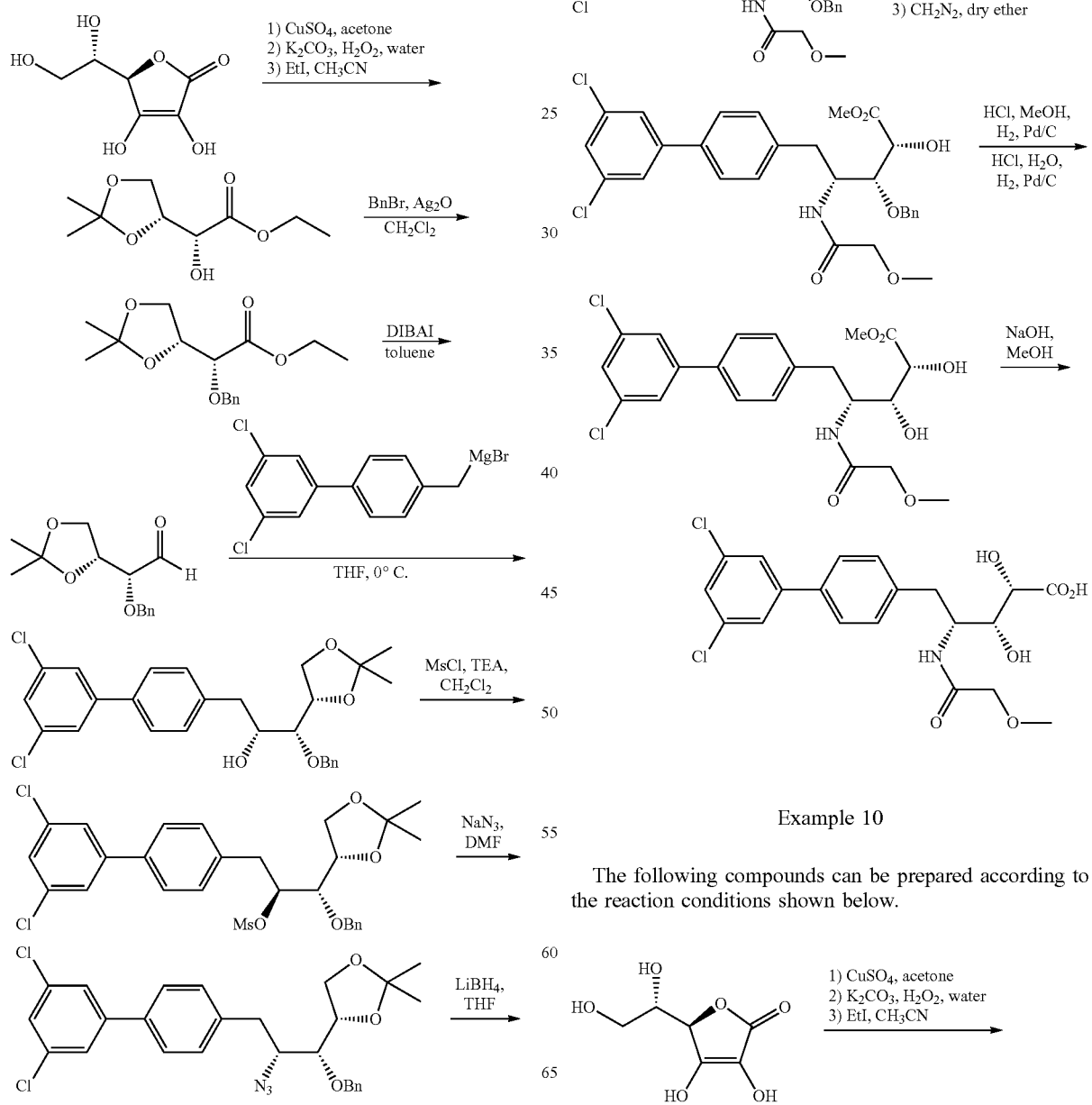
Example 10
The following compounds can be prepared according to the reaction conditions shown below.
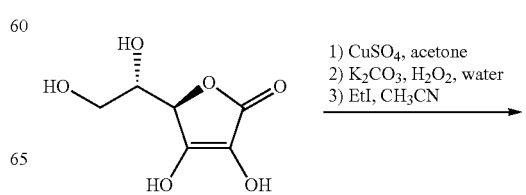

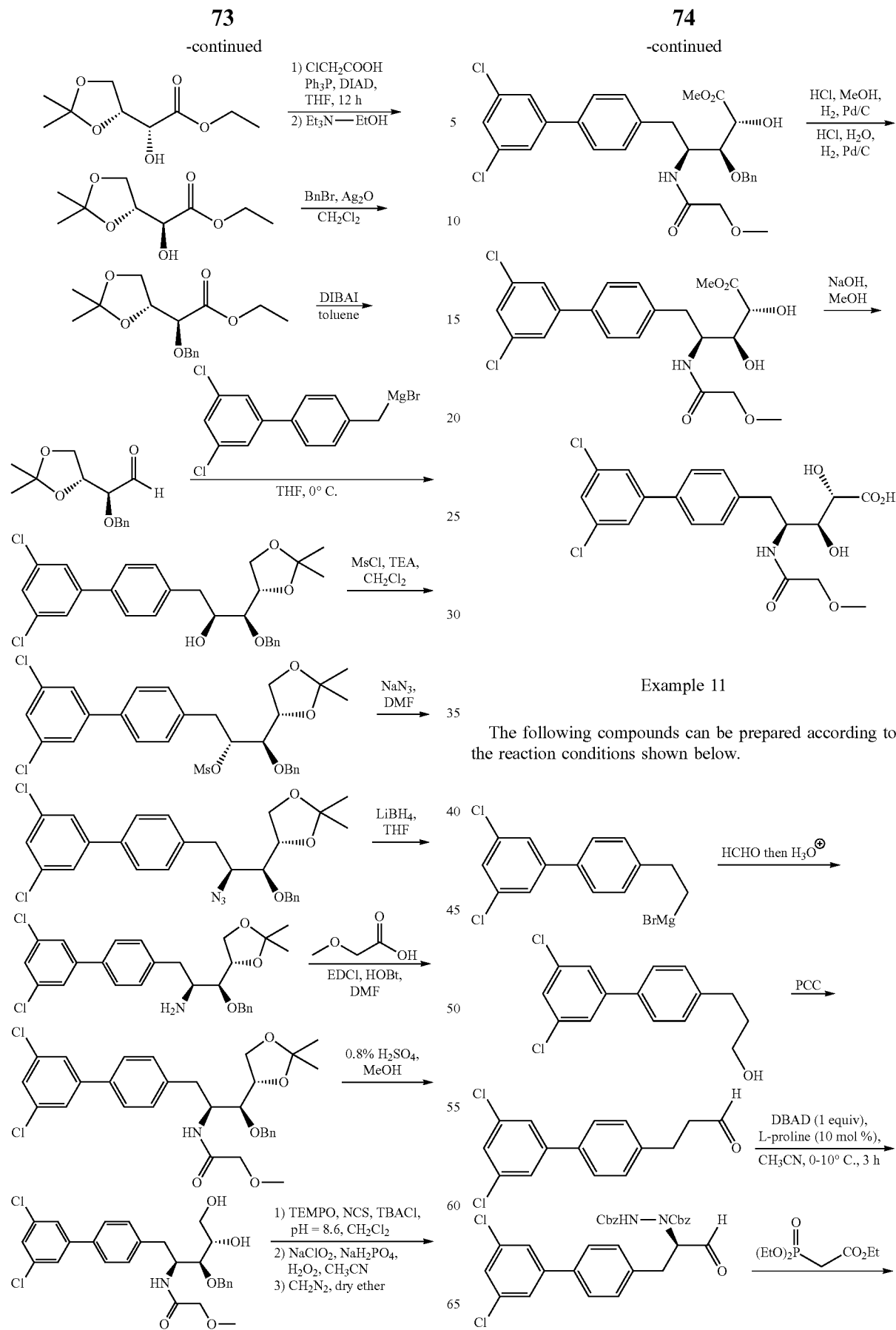
Example 11
The following compounds can be prepared according to the reaction conditions shown below.

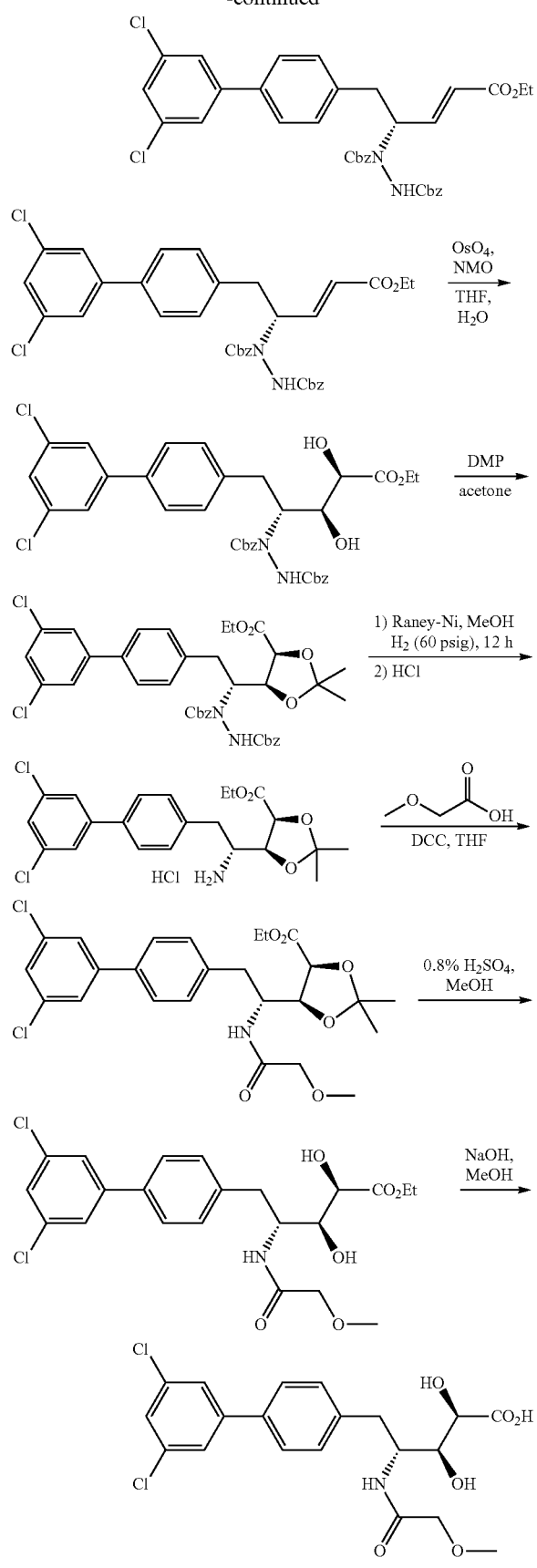
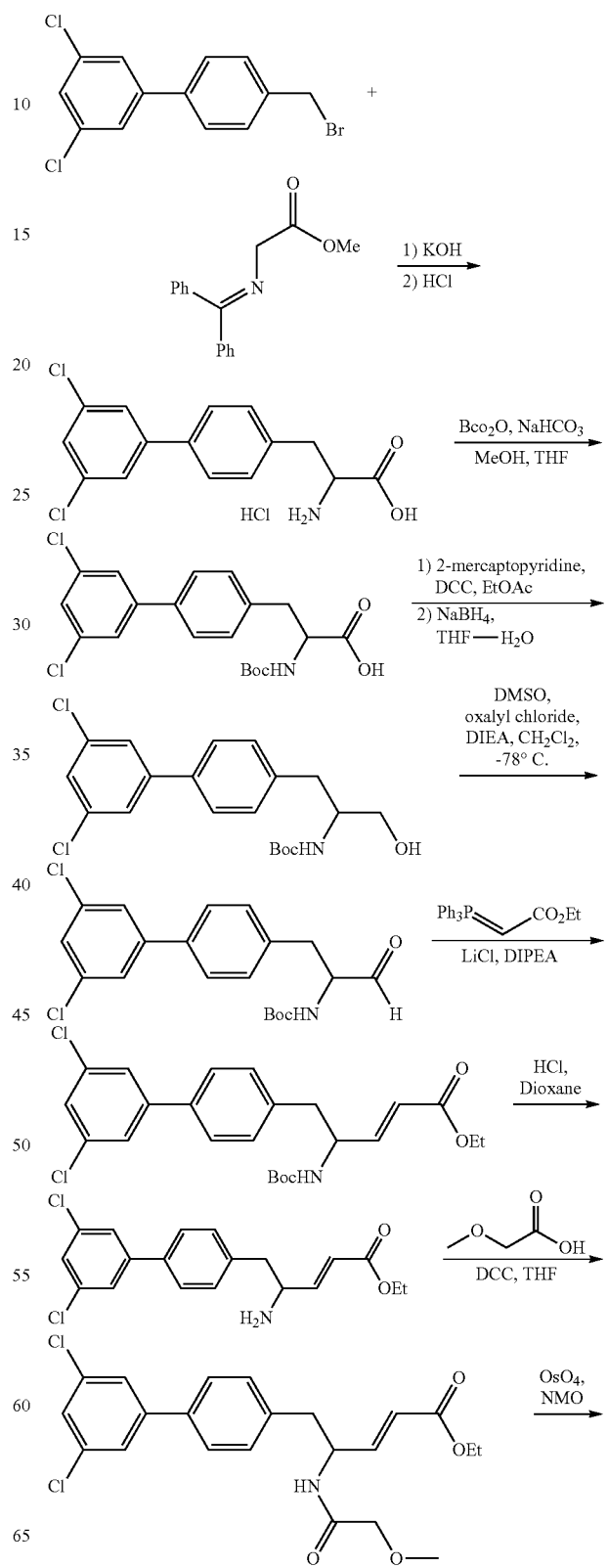
Example 12
The following compounds can be prepared according to the reaction conditions shown below.

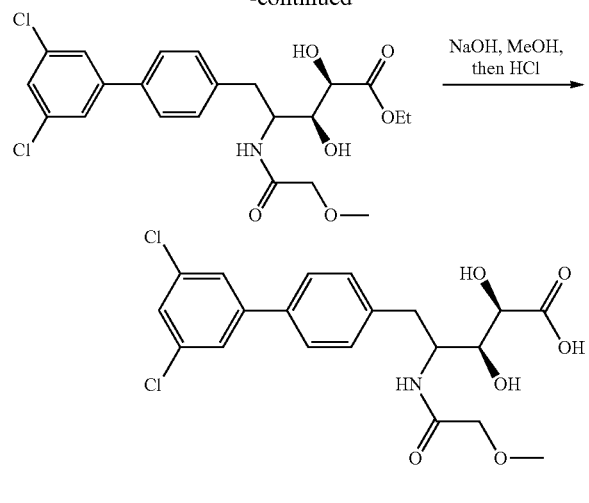
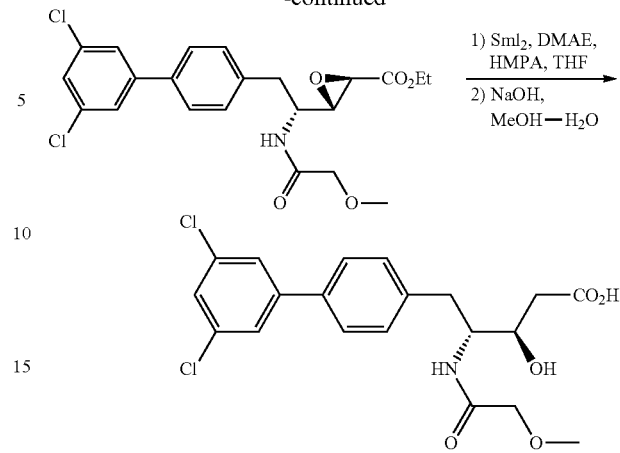
Example 13
The following compounds can be prepared according to the reaction conditions shown below.
Example 14
The following compounds can be prepared according to the reaction conditions shown below.
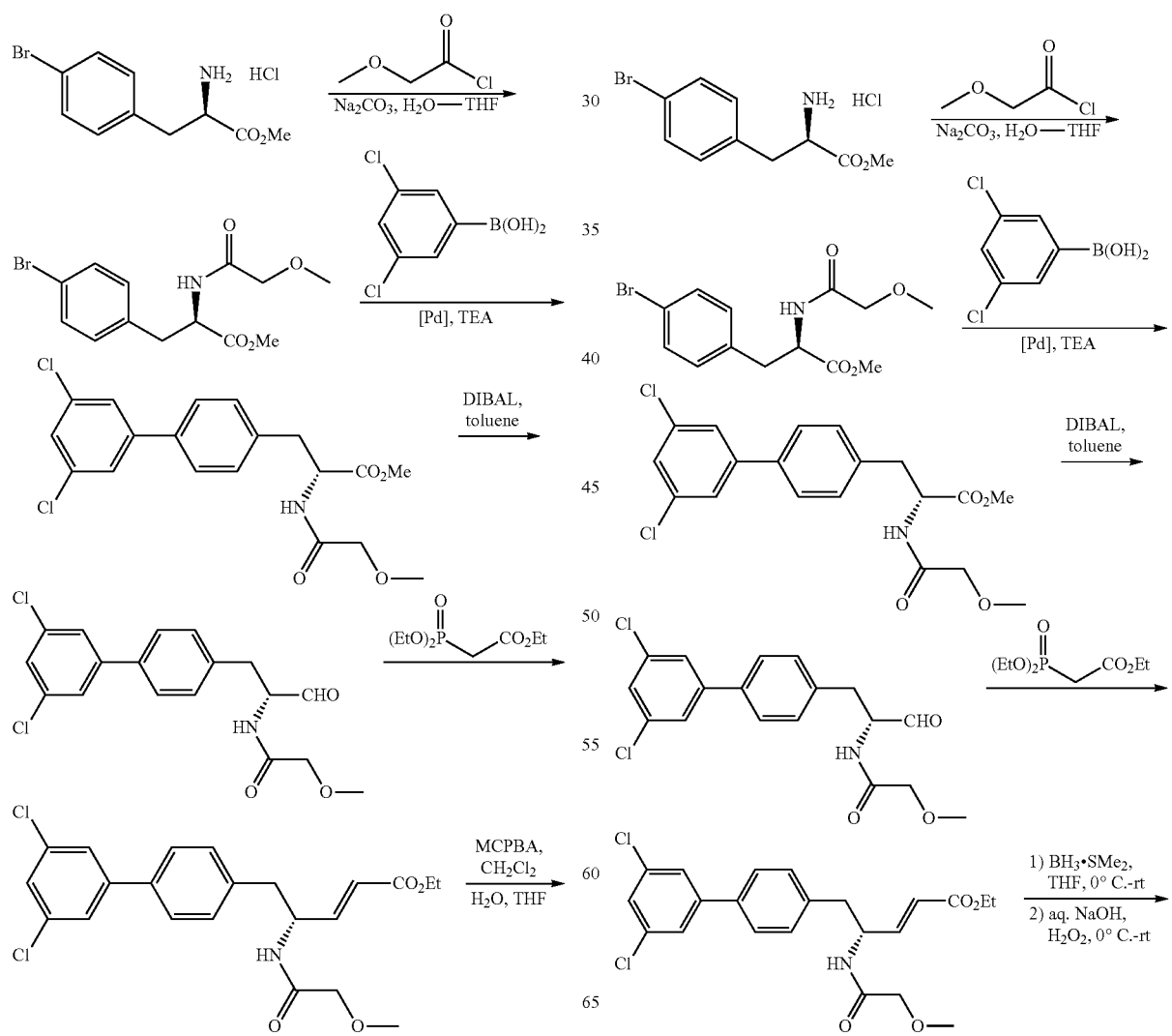

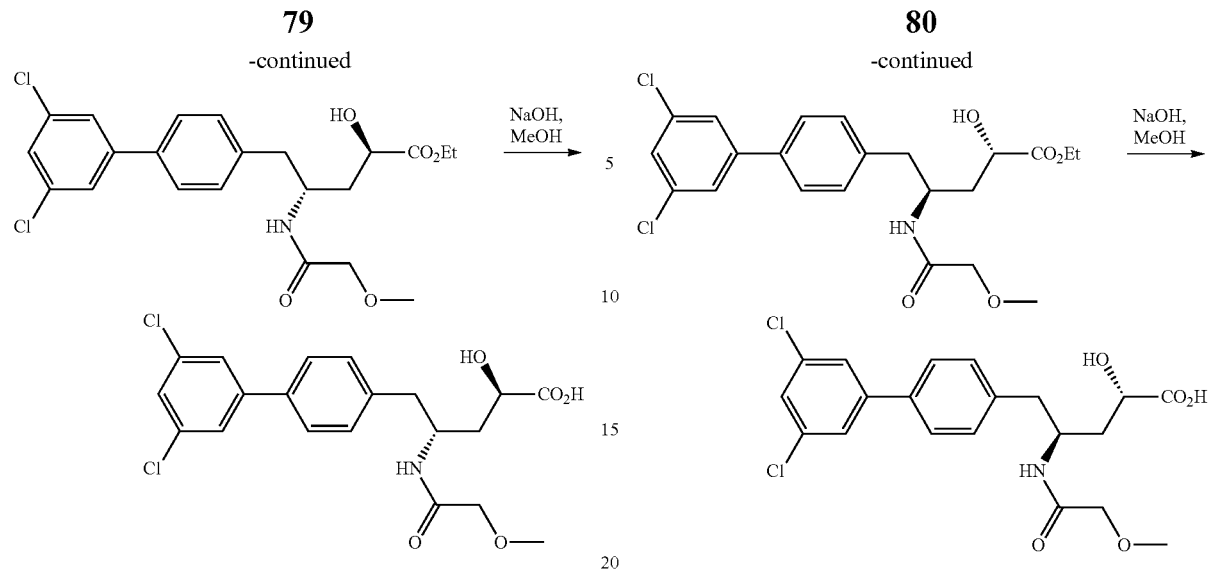
Example 15
The following compounds can be prepared according to the reaction conditions shown below.
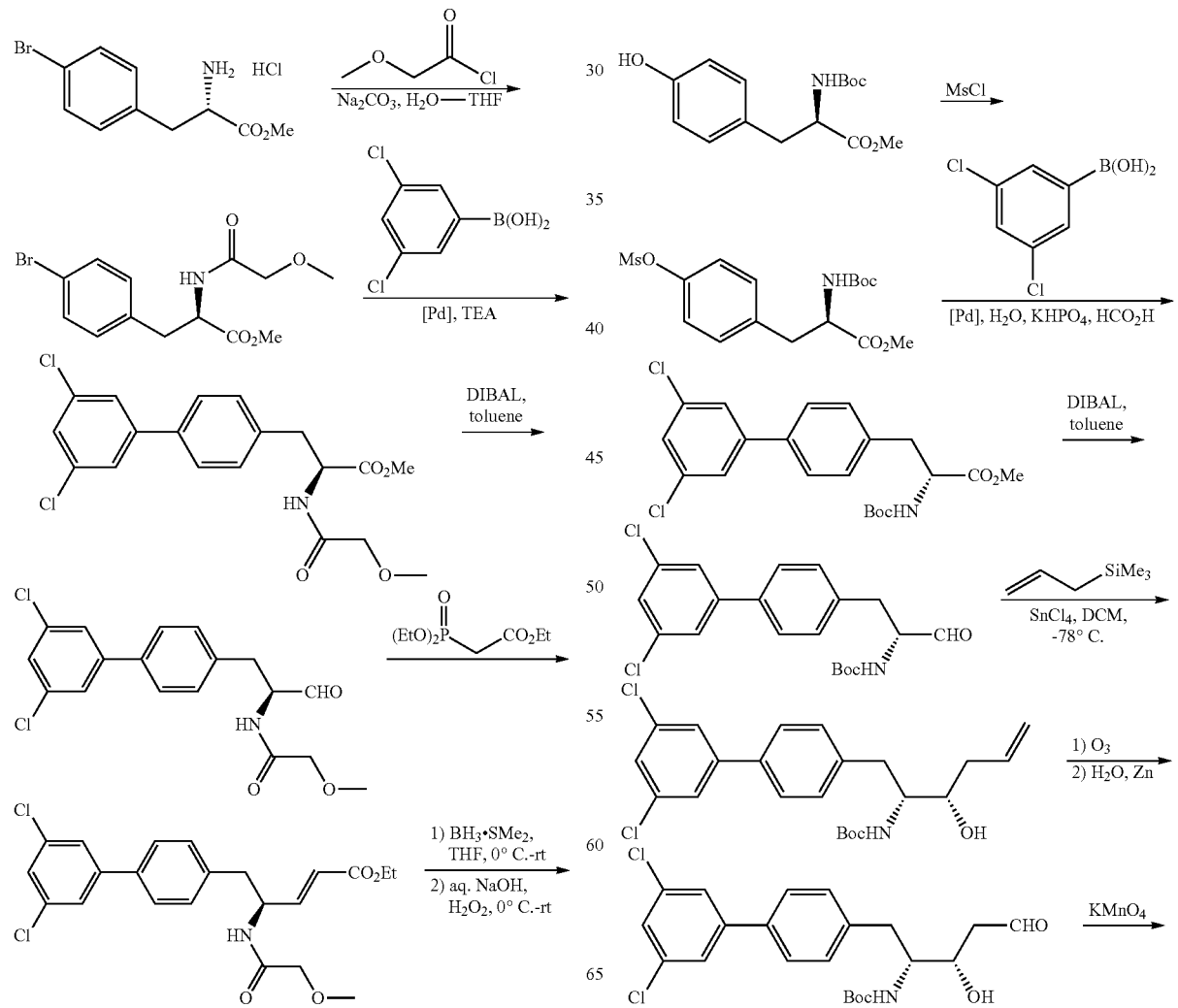
Example 16
The following compounds can be prepared according to the reaction conditions shown below.

-continued

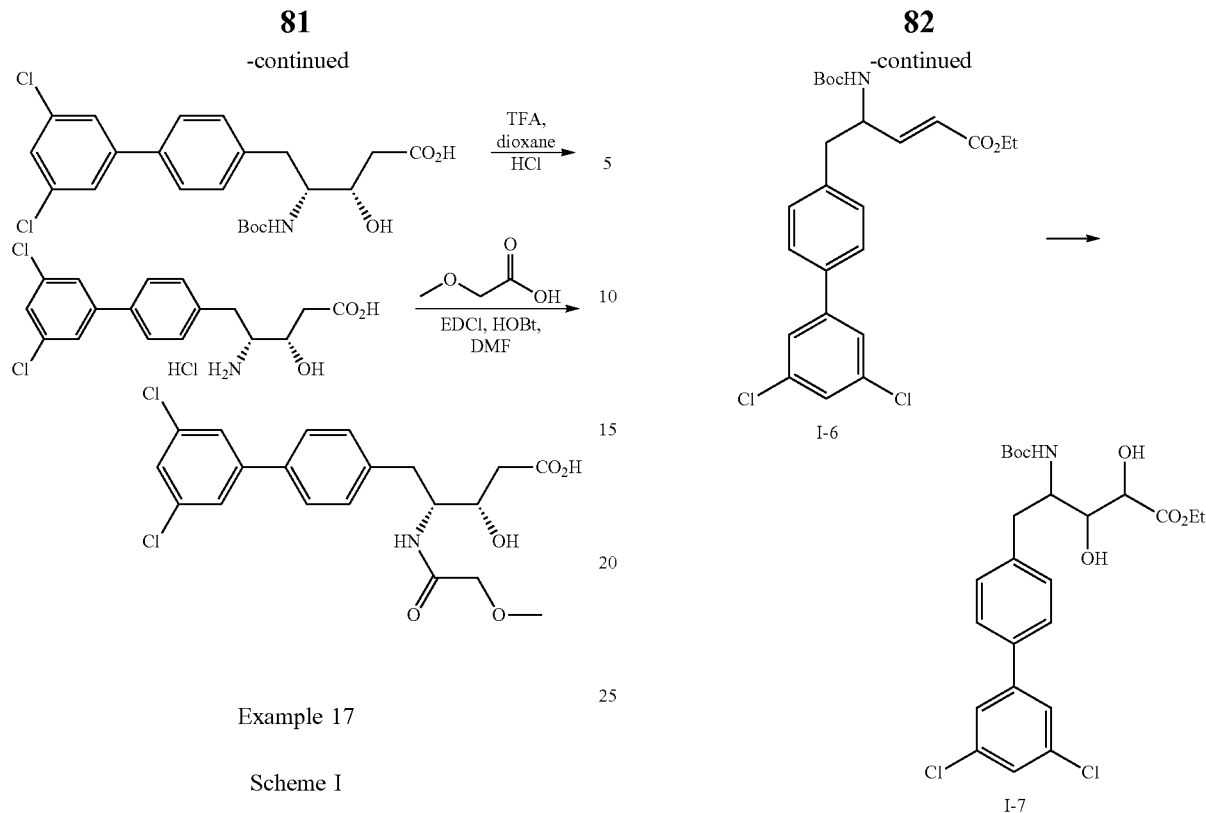

Example 17

Scheme I

The following Boc-protected compounds were prepared according to synthetic Scheme I as shown below.

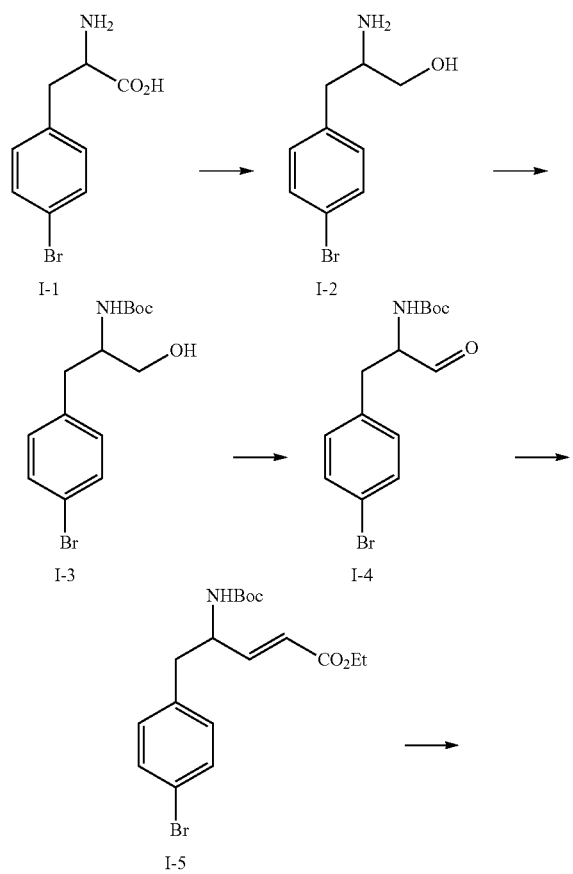

To the solution of DL-p-Bromophenylalanine (1-1) (24.40 g, 100 mmol) in 350 mL of anhydrous tetrahydrofuran was added sodium borohydride (15.20 g, 400 mmol) in small portions at 0° C. The solution was allowed to stir for 30 min. Iodine (50.80 g, 200 mmol) was then dissolved in 85 mL of anhydrous tetrahydrofuran and added dropwise to the original reaction flask slowly in an ice water bath. After stirred for additional 30 min, the resulting mixture was heated to reflux for 30 hrs, cooled to room temperature and added dropwise 300 mL of 20% KOH. The resulting solution was stirred at 50° C. for 2 hrs, cooled to room temperature, and extracted with dichloromethane (3×300 mL). The combined organic extracts were dried by $Na_2SO_4$. Removal of the solvent in vacuo afforded a residue 1-2 that was used in the next step without further purification.

To the above residue in 200 mL of anhydrous MeOH was added dropwise di-tert-butyl dicarbonate (33.00 g, 150 mmol) slowly in an ice water bath. After stirred for additional 30 min, the resulting mixture was heated to 50° C. for 1 h. Removal of the solvent in vacuo afforded white solid that was washed with petroleum ether twice to give the desired product I-3 as a white solid (23.00 g, 70%) which was pure enough for the next reaction. $^1$H-NMR (400 MHz, DMSO-$d_6$): δ 7.46 (d, J=8.4 Hz, 2H), 7.16 (d, J=8 Hz, 2H), 6.62 (d, J=8.4 Hz, 1H), 3.56 (brs, 1H), 3.36-3.23 (m, 2H), 2.83-2.78 (m, 1H), 2.53 (d, J=11.2 Hz, 1H), 1.30 (s, 9H).

To the solution of I-3 (23.00 g, 70 mmol) and TEMPO (0.47 g, 3 mmol) in 750 mL of anhydrous dichloromethane was added trichloroisocyanuric acid (17.44 g, 75 mmol) in small portions at 0° C. After stirred for additional 20 min, the resulting mixture was filtered and washed with dichloromethane. The filtrate was washed with saturated sodium thiosulfate (400 mL) and saturated brine (400 mL). The organic extract was added ethyl (triphenylphosphoranylidene) acetate and refluxed for 2 hrs. Removal of the solvent in vacuo afforded a residue that was purified by flash column chromatography to afford I-5 (15.50 g, 59%) as a white solid. $^1$H-NMR (400 MHz, DMSO-d$_6$): δ7.48 (d, J=8 Hz, 2H), 7.20 (d, J=8 Hz, 3H), 6.88 (dd, J=16, 5.6 Hz, 1H), 5.85 (d, J=15.2 Hz, 1H), 4.34 (brs, 1H), 4.14 (q, J=7.2 Hz, 2H), 2.88-2.83 (m, 1H), 2.71-2.64 (m, 1H), 1.30 (s, 9H), 1.20 (t, J=7.2 Hz, 3H).

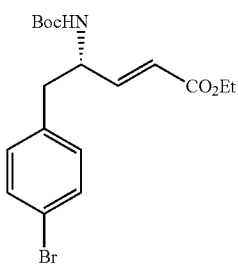

(I-5A)

Compound I-5A was prepared in 65% yield following the general procedure described in the synthesis of I-5. $^1$H-NMR (400 MHz, DMSO-d$_6$): δ 7.48 (d, J=8 Hz, 2H), 7.20 (d, J=8.4 Hz, 2H), 7.16 (s, 1H), 6.88 (dd, J=15.6, 5.6 Hz, 1H), 5.85 (m, 1H), 4.35 (brs, 1H), 4.14 (q, J=6.8 Hz, 2H), 2.88-2.83 (m, 1H), 2.68-2.62 (m, 1H), 1.30 (s, 9H), 1.22 (t, J=7.2 Hz, 3H).

To the solution of I-5 (21.54 g, 57 mmol) and 3,5-dichlorophenylboronic acid (13.00 g, 68 mmol) in 260 mL of N,N-dimethylformamide was added Pd(dppf)Cl$_2$ (0.64 g) and 2 M Na$_2$CO$_3$(75.00 g) under nitrogen. The resulting mixture was stirred at 95° C. for 6 hrs, cooled to room temperature, poured into 600 mL of water, extracted with ethyl acetate (2×400 mL) and washed with saturated brine. Removal of the solvent in vacuo afforded a residue that was purified by flash column chromatography to afford I-6 (15.00 g, 56%) as a white solid. $^1$H-NMR (400 MHz, DMSO-d$_6$): δ 7.71-7.67 (m, 4H), 7.57 (s, 1H), 7.36 (d, J=8.0 Hz, 2H), 7.23 (d, J=8.4 Hz, 1H), 6.92 (dd, J=15.6, 5.2 Hz, 1H), 5.88 (d, J=15.6 Hz, 1H), 4.40 (brs, 1H), 4.15 (q, J=6.8 Hz, 2H), 2.94-2.90 (m, 1H), 2.77-2.72 (m, 1H), 1.31 (s, 9H), 1.23 (t, J=6.8 Hz, 3H).

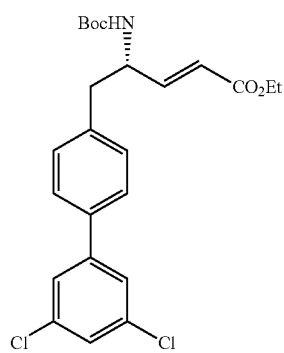

(I-6A)

I-6A was prepared in 60% yield following the general procedure described in the synthesis of I-6. $^1$H-NMR (400 MHz, DMSO-d$_6$) δ 7.72-7.67 (m, 4H), 7.57 (s, 1H), 7.36 (d, J=8.0 Hz, 2H), 7.23 (d, J=8.8 Hz, 1H), 6.91 (dd, J=15.6, 5.2 Hz, 1H), 5.88 (d, J=15.6 Hz, 1H), 4.40 (brs, 1H), 4.15 (q, J=7.2 Hz, 2H), 2.94-2.90 (m, 1H), 2.77-2.71 (m, 1H), 1.31 (s, 9H), 1.23 (t, J=6.8 Hz, 3H).

To the solution of I-6 (9.28 g, 20 mmol) in 60 mL of tetrahydrofuran, 60 mL of acetone and 60 mL of water was added 0.1 M OsO$_4$ in toluene (6 mL) in an ice water bath. The resulting mixture was stirred for additional 15 min. NMO (4.68 g, 40 mmol) was added to the reaction, stirred at room temperature for overnight, poured into diluted solution of sodium thiosulfate (300 mL), extracted with ethyl acetate (2×300 mL) and washed with saturated brine. Removal of the solvent in vacuo afforded a residue that was purified by flash column chromatography to afford I-7(7.40 g, 74%) as a white solid. $^1$H-NMR (400 MHz, DMSO-d$_6$) δ7.70-7.64 (m, 4H), 7.56 (s, 1H), 7.30 (d, J=7.6 Hz, 2H), 6.77 (d, J=8.8 Hz, 0.5H), 6.51 (d, J=8.8 Hz, 0.5H), 4.14-4.05 (m, 3H), 3.75-3.67 (m, 2H), 3.12-2.62 (m, 2H), 1.28-1.13 (m, 12H).

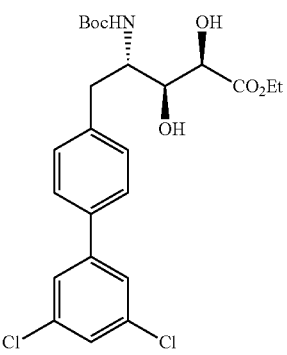

(I-7A)

To the solution of I-6A (4.64 g, 10 mmol) in 40 mL of tetrahydrofuran, 40 mL of acetone and 40 mL of water was added (DHQ)$_2$PHAL (0.78 g, 1 mmol) and 0.1 M OsO$_4$ in toluene (3 mL) in an ice water bath. The resulting mixture was stirred for additional 15 min. NMO (2.34 g, 20 mmol) was added to the reaction, stirred in an ice water bath for overnight, poured into diluted solution of sodium thiosulfate (100 mL), extracted with ethyl acetate (2×200 mL) and washed with saturated brine. Removal of the solvent in vacuo afforded a residue that was purified by flash column chromatography to afford I-7 (3.00 g, 60%) as a white solid. $^1$H-NMR (400 MHz, DMSO-d$_6$) δ 7.69-7.64 (m, 4H), 7.55 (s, 1H), 7.29 (d, J=5.2 Hz, 2H), 6.74 (d, J=6.0 Hz, 1H), 5.00 (brs, 1H), 4.95 (brs, 1H), 4.14-4.10 (m, 3H), 3.76-3.69 (m, 2H), 3.11-3.09 (m, 1H), 2.64-2.60 (m, 1H), 1.28-1.13 (m, 12H).

General Procedure for the Synthesis of Active Esters:

To the solution of acid (30 mmol) and N-hydroxysuccinimide (3.68 g, 32 mmol) in 120 mL of dichloromethane was slowly added DCC (6.60 g, 32 mmol) in small portions in an ice water bath. The reaction was stirred for additional 2 hrs, filtered with a pad of silica-gel, washed with dichloromethane. Removal of the solvent in vacuo afforded the desired product which was used in the next step without further purification.

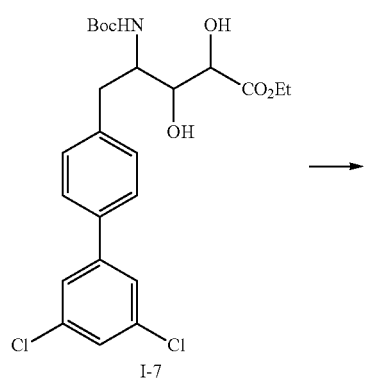

I-7

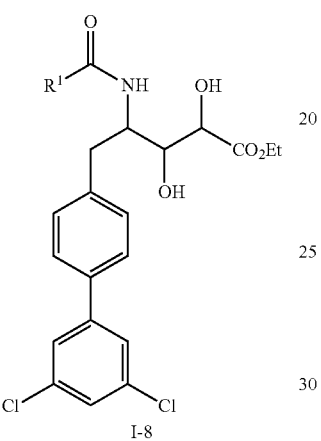

I-8

To the solution of I-7 (1.00 g, 2 mmol) in 8 mL of dichloromethane and 8 mL of ethanol was added 6 M HCl in dioxane (6 mL). The reaction was stirred at 30° C. for 2 hrs. Removal of the solvent in vacuo afforded a residue that was dissolved in 10 mL of N,N-dimethylformamide in an ice water bath. 14% $Na_2CO_3$ (3.03 g, 4 mmol) and active ester (3 mmol) was added to the reaction, stirred at room temperature for 3 hrs, poured into diluted solution of ammonium chloride (100 mL), extracted with ethyl acetate (2×100 mL) and washed with saturated brine. Removal of the solvent in vacuo afforded a residue that was purified by flash column chromatography to afford I-8.

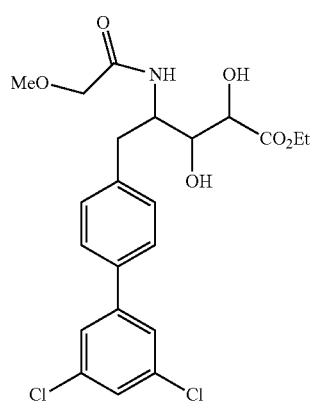

(A1)

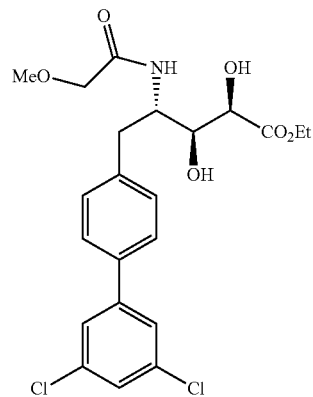

(A2)

A1 was prepared in 64% yield following the general procedure described in the synthesis of I-8. $^1$H-NMR (400 MHz, DMSO-$d_6$) δ 7.83 (d, J=9.2 Hz, 0.5H), 7.72-7.65 (m, 4H), 7.56 (d, J=1.6 Hz, 1H), 7.45 (d, J=8.8 Hz, 0.5H), 7.30 (d, J=7.6 Hz, 2H), 4.16-4.04 (m, 4H), 3.75-3.64 (m, 3H), 3.24 (s, 1.5H), 3.20 (s, 1.5H), 3.12-2.79 (m, 2H), 1.22-1.14 (m, 3H).

A2 was prepared in 60% yield following the general procedure described in the synthesis of I-8. $^1$H-NMR (400 MHz, DMSO-$d_6$) δ 7.83 (d, J=9.2 Hz, 1H), 7.72-7.65 (m, 4H), 7.56 (s, 1H), 7.31 (d, J=8.0 Hz, 2H), 4.16-4.10 (m, 4H), 3.79-3.60 (m, 3H), 3.20 (s, 3H), 3.12-3.07 (m, 1H), 2.82-2.76 (m, 1H), 1.23 (t, J=7.2 Hz, 3H).

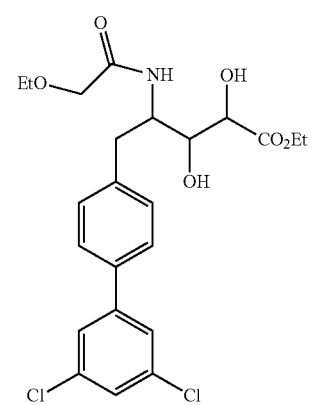

(B1)

B1 was prepared in 70% yield following the general procedure described in the synthesis of I-8. $^1$H-NMR (400 MHz, DMSO-$d_6$) δ 7.72-7.65 (m, 4H), 7.56 (s, 1H), 7.37-7.28 (m, 3H), 4.17-4.03 (m, 4H), 3.78-3.70 (m, 3H), 3.39-3.31 (m, 2H), 2.90-2.79 (m, 2H), 1.21-1.08 (m, 6H).

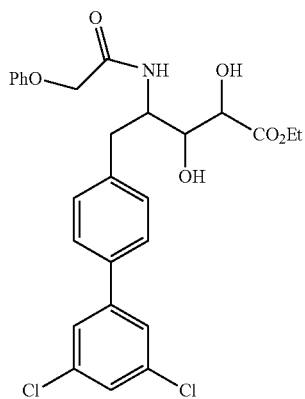
(B2)

B2 was prepared in 55% yield following the general procedure described in the synthesis of I-8. ¹H-NMR (400 MHz, DMSO-$d_6$) δ 8.09-7.56 (m, 6H), 7.29-7.23 (m, 4H), 6.93-6.84 (m, 3H), 4.41-4.36 (m, 2H), 4.18-4.06 (m, 4H), 3.78-3.77 (m, 1H), 2.89-2.73 (m, 2H), 1.22-1.15 (m, 3H).

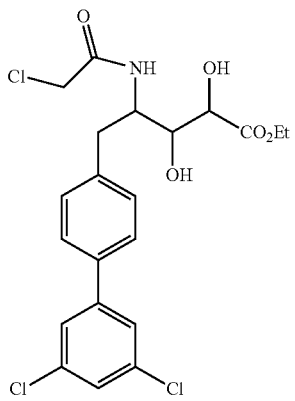
(B3)

B3 was prepared in 50% yield following the general procedure described in the synthesis of I-8. ¹H-NMR (400 MHz, DMSO-$d_6$) δ 8.19 (d, J=6.0 Hz, 0.4H), 8.02 (d, J=5.6 Hz, 0.6H), 7.72-7.56 (m, 5H), 7.30 (d, J=5.2 Hz, 2H), 5.35-5.07 (m, 2H), 4.08-3.95 (m, 6H), 3.25 (brs, 1H), 3.10-2.73 (m, 2H), 1.21-1.15 (m, 3H).

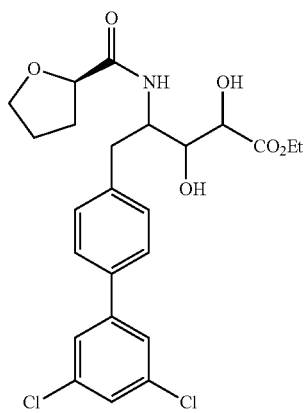
(B4)

B4 was prepared in 58% yield following the general procedure described in the synthesis of I-8. ¹H-NMR (400 MHz, DMSO-$d_6$) δ 7.73-7.64 (m, 5H), 7.55 (S, 1H), 7.29-7.27 (m, 2H), 4.15-4.06 (m, 5H), 3.78-3.69 (m, 3H), 3.15-2.78 (m, 2H), 1.40-1.16 (m, 7H).

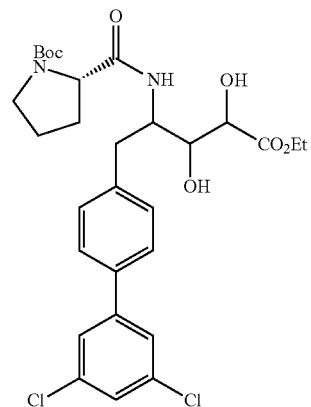
(B5)

B5 was prepared in 66% yield following the general procedure described in the synthesis of I-8. ¹H-NMR (400 MHz, DMSO-$d_6$) δ 8.09-7.56 (m, 5H), 7.36-7.30 (m, 3H), 4.17-3.70 (m, 6H), 3.28-3.13 (m, 2H), 2.89-2.73 (m, 2H), 1.91-1.14 (m, 3H), 0.85-0.82 (m, 13H).

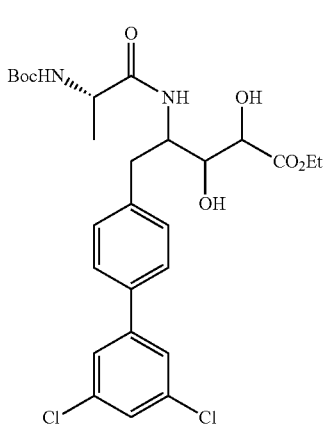
(B6)

B6 was prepared in 72% yield following the general procedure described in the synthesis of I-8. ¹H-NMR (400 MHz, DMSO-$d_6$) δ 8.01 (d, J=6.0 Hz, 0.5H), 7.69-7.61 (m, 4.5H), 7.56 (s, 1H), 7.30 (m, 2H), 6.81-6.74 (m, 1H), 4.23-3.67 (m, 6H), 3.20-3.14 (m, 1H), 2.82-2.68 (m, 1H), 1.21-0.89 (m, 15H).

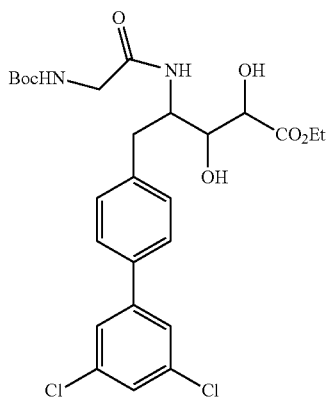

(B7)

B7 was prepared in 46% yield following the general procedure described in the synthesis of I-8. $^1$H-NMR (400 MHz, DMSO-d$_6$) δ 7.80-7.62 (m, 5H), 7.56 (s, 1H), 7.30 (m, J=5.2 Hz, 2H), 6.84 (s, 1H), 5.07 (brs, 1H), 4.90 (brs, 1H), 4.17-3.69 (m, 4H), 3.08-3.05 (m, 1H), 2.83-2.68 (m, 1H), 1.36 (s, 9H), 1.21-1.18 (t, J=4.8 Hz, 3H).

General Procedure for the Synthesis of I-9:

To the solution of I-8 (1 mmol) in 10 mL of tetrahydrofuran and 0.2 mL of water was added lithium hydroxide monohydrate (0.21 g, 5 mmol). The reaction was stirred at 35° C. for 1 h, poured into diluted hydrochloric acid (60 mL), extracted with ethyl acetate (2×60 mL) and washed with saturated brine. Removal of the solvent in vacuo afforded a residue that was purified by flash column chromatography to afford the desired product I-9.

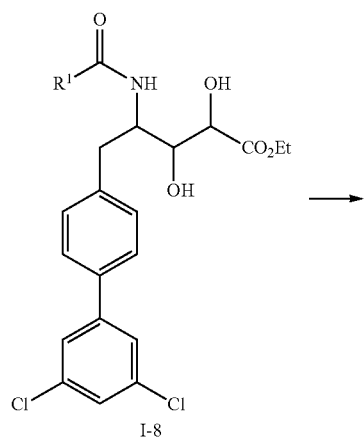

I-8

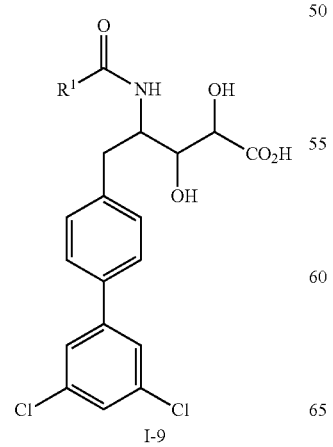

I-9

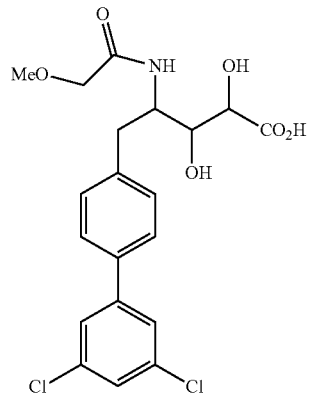

(A3)

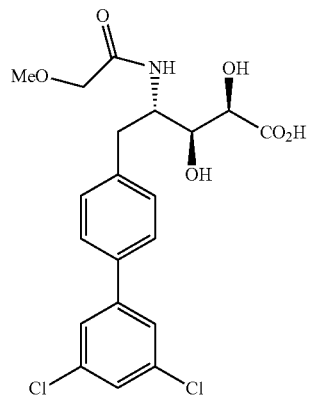

(A4)

A3 was prepared in 40% yield following the general procedure described in the synthesis of I-9. $^1$H-NMR (400 MHz, DMSO-d$_6$) δ 7.80 (d, J=9.2 Hz, 1H), 7.72-7.65 (m, 4H), 7.56 (s, 1H), 7.31 (d, J=7.6 Hz, 1H), 4.16-4.05 (m, 2H), 3.78-3.61 (m, 3H), 3.22-3.20 (ss, 3H), 3.11-3.08 (m, 1H), 2.82-2.76 (m, 1H).

A4 was prepared in 43% yield following the general procedure described in the synthesis of I-9. $^1$H-NMR (400 MHz, DMSO-d$_6$) δ 7.80 (d, J=8.8 Hz, 1H), 7.72-7.65 (m, 4H), 7.56 (s, 1H), 7.31 (d, J=8.0 Hz, 1H), 5.04 (brs, 1H), 4.85 (brs, 1H), 4.17-4.09 (m, 2H), 3.75-3.65 (m, 3H), 3.20 (s, 3H), 3.11-3.07 (m, 1H), 2.82-2.76 (m, 1H).

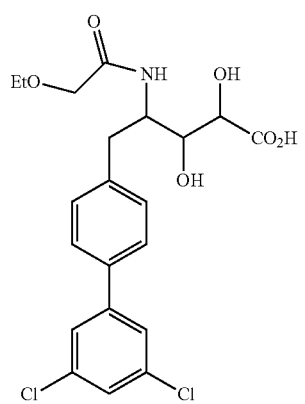

(B8)

B8 was prepared in 50% yield following the general procedure described in the synthesis of I-9. $^1$H-NMR (400

MHz, DMSO-$d_6$) δ 7.82-7.61 (m, 4H), 7.54 (s, 1H), 7.45-7.30 (m, 3H), 3.92-3.55 (m, 4H), 3.39-3.14 (m, 3H), 2.94-2.82 (m, 2H), 1.09-0.99 (m, 3H).

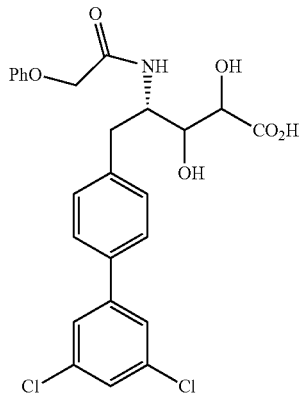
(B9)

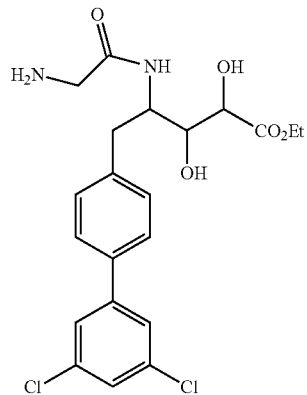
(B11)

B11 was prepared in 43% yield following the general procedure described above. $^1$H-NMR (400 MHz, DMSO-$d_6$) δ 7.71-7.56 (m, 6H), 7.36-7.31 (m, 2H), 4.19-4.12 (m, 4H), 3.73-3.65 (m, 1H), 3.39-3.09 (m, 3H), 2.75 (brs, 1H), 1.21 (brs, 3H).

B9 was prepared in 48% yield following the general procedure described in the synthesis of I-9. $^1$H-NMR (400 MHz, DMSO-$d_6$) δ 8.09-7.56 (m, 6H), 7.30-7.23 (m, 4H), 6.92-6.85 (m, 3H), 4.40-4.38 (m, 2H), 4.20-4.11 (m, 2H), 3.82-3.80 (m, 1H), 3.09-2.79 (m, 2H).

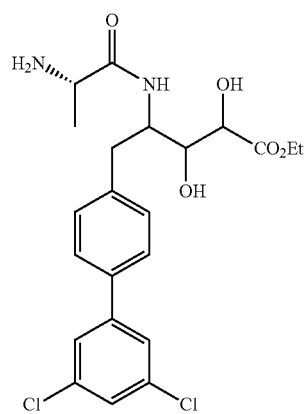
(B12)

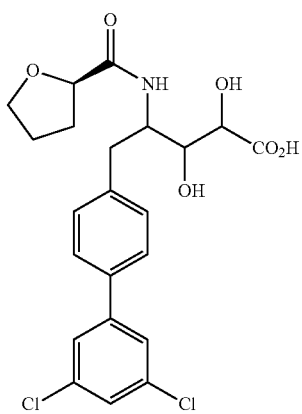
(B10)

B12 was prepared in 55% yield following the general procedure described above. $^1$H-NMR (400 MHz, DMSO-$d_6$) δ 7.93-7.64 (m, 5H), 7.55 (s, 1H), 7.31 (d, J=4.4 Hz, 2H), 4.17-4.03 (m, 4H), 3.73-3.70 (m, 1H), 3.45-3.08 (m, 2H), 2.81-2.75 (m, 1H), 1.21 (brs, 3H), 0.95 (brs, 3H).

B10 was prepared in 60% yield following the general procedure described in the synthesis of I-9. $^1$H-NMR (400 MHz, DMSO-$d_6$) δ 7.69-7.65 (m, 5H), 7.56 (s, 1H), 7.29 (brs, 2H), 4.11-4.04 (m, 3H), 3.78-3.70 (m, 3H), 3.10-2.78 (m, 2H), 1.98-1.17 (m, 4H).

General Procedure for the Synthesis of Amines from Boc-Amide:

To the solution of amide (250 mg) in 10 mL of ethyl acetate was added 5.8 M HCl in ethyl acetate (5 mL). The reaction was stirred at 25° C. for 2 hrs, poured into saturated sodium bicarbonate (60 mL), extracted with ethyl acetate (2×50 mL) and dried over anhydrous sodium sulfate. Removal of the solvent in vacuo afforded a residue that was purified by flash column chromatography to afford the desired product.

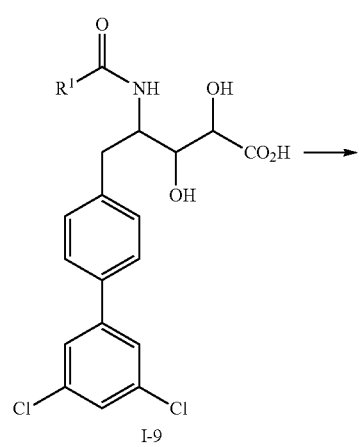
I-9

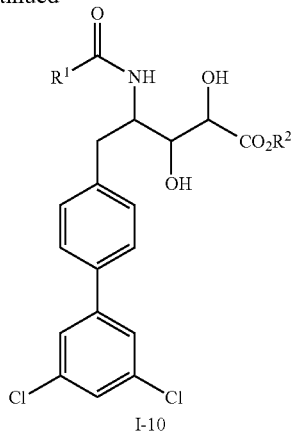

I-10

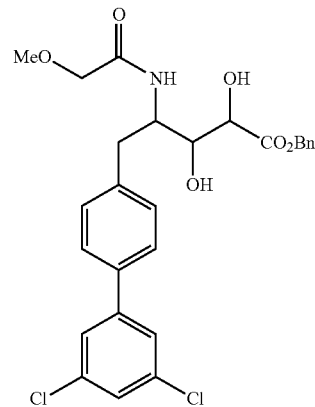

(B14)

B14 was prepared in 57% yield following the general procedure described in the synthesis of I-10. $^1$H-NMR (400 MHz, DMSO-$d_6$): δ7.70 (d, J=0.8 Hz, 2H), 7.65 (d, J=5.2 Hz, 2H), 7.56 (s, 1H), 7.46 (d, J=6.0 Hz, 1H), 7.38-7.22 (m, 7H), 5.15-5.05 (m, 3H), 4.17 (brs, 2H), 3.78-3.63 (m, 3H), 3.21 (s, 3H), 2.93-2.90 (m, 1H), 2.81-2.78 (m, 1H).

Example 18

Assays

Proliferation Assays

Figure 2A:
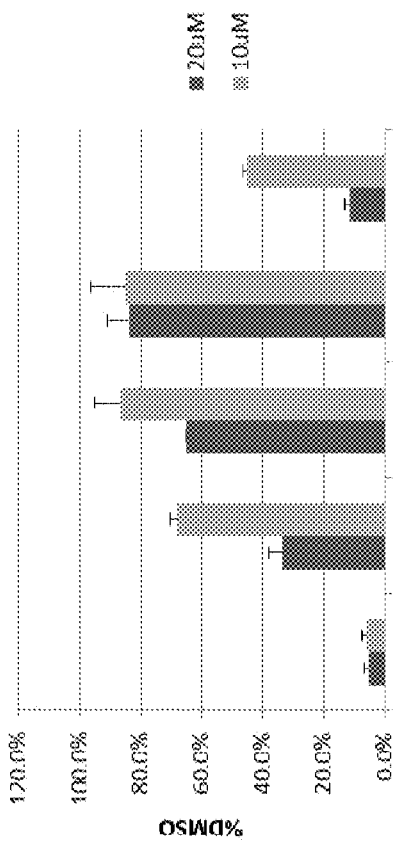
FIG. 2A illustrates the proliferation assay results in the MDA-MB-468 (breast cancer) cell line. Compounds B3, B5, B7, B11 and B12 were tested in 20 μM and 10 μM concentration respectively.
Figure 2B:
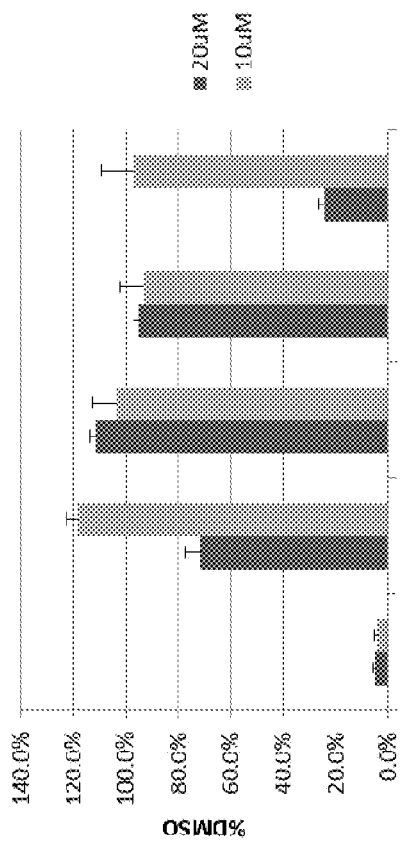
FIG. 2B illustrates the proliferation assay results where Panc-1 (pancreatic cancer) cell line was used. Compounds B3, B5, B7, B11 and B12 were tested in 20 μM and 10 μM concentration respectively.

Proliferation assays were conducted to assess the effects of the compounds described herein on the growth rate of neoplastic cells. For each of the proliferation assays described herein, SK-MEL-28, MDA-MB-468 or Panc-1 cells were grown in RPMI supplemented with 10% FBS and plated onto sterile 96-well tissue culture plates at 20,000 cells per well and allowed to attach overnight. Compounds B1 through B14 were added at 20 µM and 10 µM respectively in the SK-MEL-28 proliferation assay (FIG. 1). Compounds B3, B5, B7, B11 and B12 were added at 20 µM and 10 µM respectively for the MDA-MB-468 (FIG. 2A) and Panc-1 proliferation assays (FIG. 2B). Plates were incubated for 72 h (37° C., 5% $CO_2$). Percent viability compared to DMSO control was determined using an MTS assay (Cell-Titer 96 Aqueous, Promega) according to the manufacturer's standard protocol. The standard used in the SK-MEL-28 assay is MG132, a proteasome inhibitor, at 10 uM concentration. It was used as a positive control for cell killing. All the assays are referenced to DMSO as the control at 100% proliferation.

In particular, Compound B12 demonstrated excellent inhibitory effect at 20 µM concentration, which is about 20 fold more effective than the control (FIG. 1). Compounds B3, B5, B7 and B11 also showed good inhibitory effect.

Compound B3 demonstrated good inhibitory effect in both the MDA-MB-468 assay and the Panc-1 assay at both concentrations, showing 5.5% and 6.0% growth rate in the MDA-MB-468 assay and 5.2% and 4.8% growth rate in the Panc-1 assay at 20 µM and 10 µM respectively. Compound B5 and Compound B12 showed 33.5% and 11.0% growth rate respectively in the MDA-MD-468 assay when used at 20 µM. Compound B12 showed 24.4% growth rate in the Panc-1 assay when used at 20 µM.

General Procedure for the Synthesis of Esters I-10:

To the solution of I-9 (0.9 mmol) in 5 mL of alcohol was added 5.8 M HCl in ethyl acetate (5 mL). The reaction was stirred at 25° C. for 3 hrs, poured into saturated sodium bicarbonate (60 mL), extracted with ethyl acetate (2×50 mL) and dried over anhydrous sodium sulfate. Removal of the solvent in vacuo afforded a residue that was purified by flash column chromatography to afford the desired product I-10.

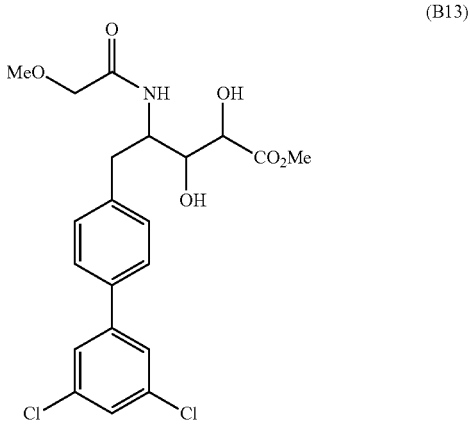 [SMILES: COCC(=O)NC(Cc1ccc(-c2cc(Cl)cc(Cl)c2)cc1)C(O)C(O)C(=O)OC]

(B13)

B13 was prepared in 60% yield following the general procedure described in the synthesis of I-10. $^1$H-NMR (400 MHz, DMSO-$d_6$): δ 7.80 (d, J=6.0 Hz, 1H), 7.71-7.65 (m, 4H), 7.55 (s, 1H), 7.30 (d, J=5.2 Hz, 2H), 5.12 (d, J=5.2 Hz, 2H), 4.18-4.14 (m, 2H), 3.80-3.61 (m, 6H), 3.19 (s, 3H), 3.11-3.08 (m, 1H), 2.81-2.77 (m, 1H).

Figure 3:
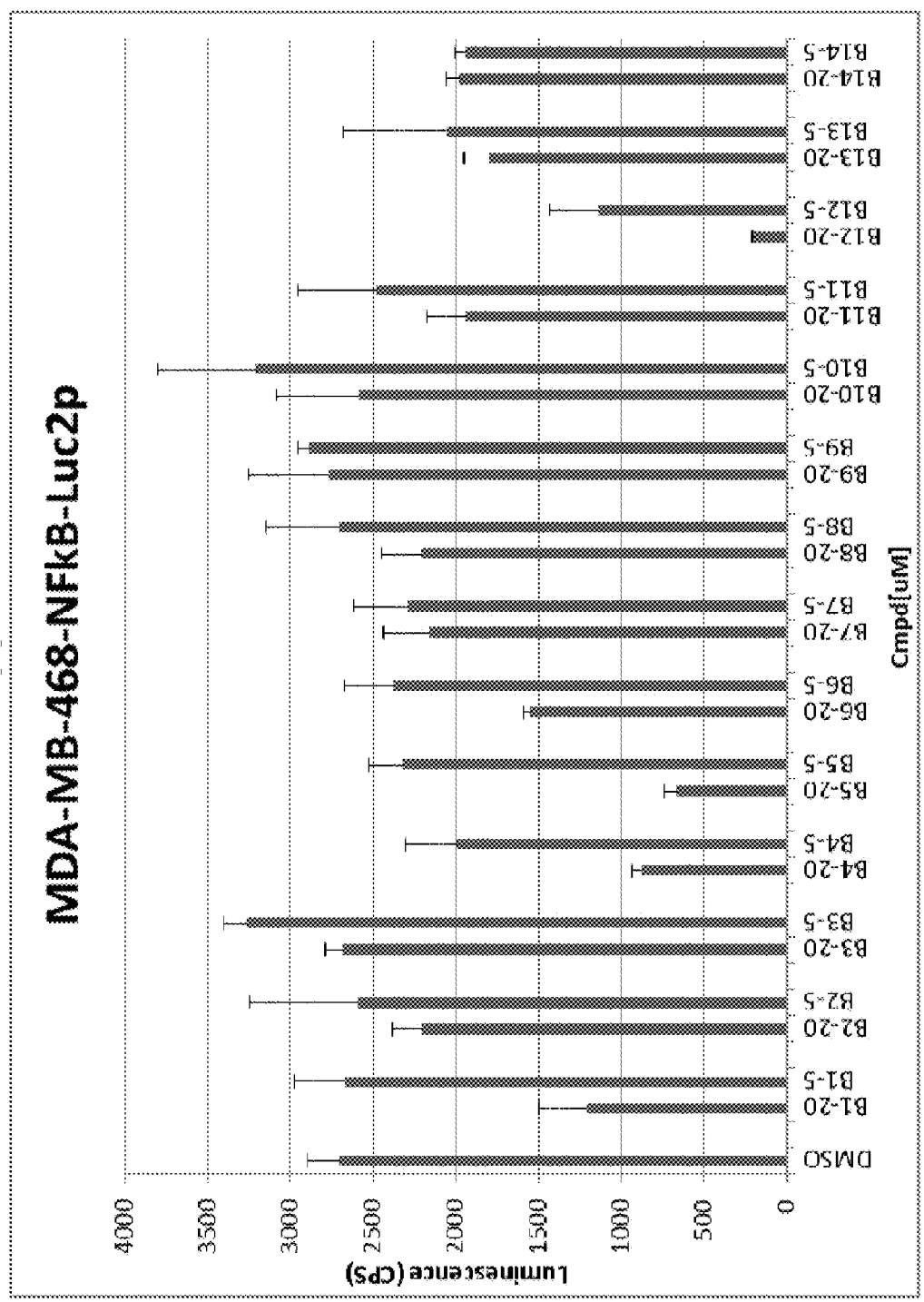
FIG. 3 illustrates TNF-α induced NFkB reporter assay results in the MDA-MB-468-NFkB-Luc2p cell line. Compounds B1 through B14 were tested in 20 μM and 5 μM concentration respectively.

TNF-α Induced NFkB Reporter Assays:

Generation of Stable MDA-MB-468-NFkB-Luc2p Reporter Cell Line:

The effects of the compounds described herein on the activation of TNF-mediated pathways were assessed using an MDA-MB-468NFkB-Luc2p reporter cell line (FIG. 3). To construct this cell line, MDA-MB-468 cells were transfected with pGL4.32[luc2P/NF-kB-RE/Hygro] vector (Promega) using TransFast transfection reagent (Promega) according to manufacturer's standard protocol. Briefly, cells were grown in RPMI supplemented with 10% FBS and plated onto sterile 6-well plates (Nunc). When cells became ~75% confluent, media in each well was removed and replaced with 1 mL RPMI (no FBS) containing pGL4.41 [luc2P/NFkB/Hygro] vector and TransFast for 1 h at 37° C. 2 mL of RPMI with FBS is then added to the well and after 24 h, 500 ug/ml of hygromycin was added for selection to generate a stable reporter cell line.

Assay Results

Stable MDA-MB-468-NFkB-Luc2p cells were plated onto optical-bottom, white wall 96-well plates at 10,000 cells per well and allowed to attach overnight. Compounds B1 through B14 were added at 20 μM and 5 μM respectively for 1 h prior to treatment with 10 ng/ml of recombinant human TNF-α for 6 h. Luciferase signal was determined using the Luciferase Assay System (Promega) and a luminometer. The results are provided in FIG. 3. In particular, Compound B12 demonstrated excellent inhibitory effect at 20 μM concentration. Compounds B1, B4, and B5 also showed good results.

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method for ameliorating a cancer condition selected from the group consisting of melanoma, breast cancer, pancreatic cancer, multiple myeloma, mantle cell lymphoma, glioma, cancers with low levels of the let-7 microRNA, lung cancer, colon cancer, non-hod kin's 1 mphoma, and T cell acute lympho-blastic leukemia, comprising administering a therapeutically effective amount of a compound of Formula (I), or a pharmaceutically acceptable salt thereof, or a pharmaceutical composition thereof to a subject in need thereof:

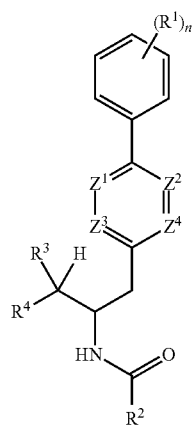

(I)

wherein:
n is selected from the group consisting of 0, 1, 2, 3, 4, and 5;
each $R^1$ is independently selected from the group consisting of halo, cyano, and azido;
$Z^1$, $Z^2$, $Z^3$, and $Z^4$ are each independently —CH—;
$R^2$ is selected from the group consisting of an optionally substituted ($C_{2-6}$ alkoxy)$C_{1-6}$ alkyl, an optionally substituted $C_{6-10}$ aryl, an optionally substituted (aryloxy)$C_{1-6}$ alkyl, an optionally substituted $C_{3-7}$ cycloalkyl, an optionally substituted haloalkyl, and an optionally substituted aminoalkyl;
$R^3$ is —OH;
$R^4$ is

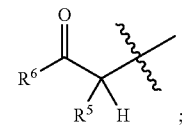

;

$R^5$ is hydrogen —OH;
$R^6$ is selected from the group consisting of —OH, —NHR$^7$, an optionally substituted $C_{1-6}$ alkyl, an optionally substituted $C_{1-6}$ alkoxy, an optionally substituted $C_{6-10}$ aryl, an optionally substituted aryloxy, and an optionally substituted arylalkoxy;
$R^7$ is hydrogen or an optionally substituted $C_{1-6}$ alkyl.

2. The method of claim 1, wherein n is 2.
3. The method of claim 1, wherein each $R^1$ is halo.
4. The method of claim 3, wherein each $R^1$ is chloro.
5. The method of claim 1, wherein $R^2$ is ($C_{2-6}$ alkoxy)$C_{1-6}$ alkyl.
6. The method of claim 5, wherein $R^2$ is ethoxymethyl.
7. The method of claim 1, wherein $R^2$ is (aryloxy)$C_{1-6}$ alkyl.
8. The method of claim 7, wherein $R^2$ is phenoxymethyl.
9. The method of claim 1, wherein $R^2$ is $C_{3-7}$ cycloalkyl.
10. The method of claim 9, wherein $R^2$ is cyclopentyl.
11. The method of claim 1, wherein $R^2$ is haloalkyl.
12. The method of claim 11, wherein $R^2$ is selected from the group consisting of —CH$_2$Cl, —CH$_2$Br, —CH$_2$CH$_2$Cl, —CH$_2$CH$_2$Br, —CH(Cl)CH$_3$ and —CH(Br)CH$_3$.
13. The method of claim 1, wherein $R^2$ is optionally substituted aminoalkyl.
14. The method of claim 13, wherein $R^2$ is selected from the group consisting of —CH$_2$NH$_2$, —CH$_2$NH(Boc), —CH(NH$_2$)CH$_3$, and —CH(Boc-NH)CH$_3$.
15. The method of claim 1, wherein $R^6$ is selected from the group consisting of —OH, —NHR$^7$, an optionally substituted $C_{1-6}$ alkoxy, and an optionally substituted arylalkoxy.
16. The method of claim 15, wherein $R^6$ is selected from the group consisting of —OH, —OCH$_2$Ph and —OCH$_2$CH$_3$.
17. The method of claim 15, wherein $R^6$ is —OCH$_2$CH$_3$.
18. The method of claim 15, wherein $R^6$ is $C_{1-6}$ alkyl substituted with one or more groups selected from the group consisting of halogen, —OH, —COOH, —NR$^8$R$^9$, $C_{1-6}$ alkoxy, and $C_{5-10}$ heteroaryl; wherein $R^8$ and $R^9$ are each independently hydrogen or $C_{1-6}$ alkyl.
19. The method of claim 15, wherein $R^6$ is —NHR$^7$.
20. The method of claim 19, wherein $R^7$ is an optionally substituted $C_{1-6}$ alkyl.

21. The method of claim 1, wherein the compound of Formula (I) is selected from the group consisting of Formula (II), Formula (III), Formula (IV), Formula (V) and Formula (VI), or a pharmaceutically acceptable salt thereof:

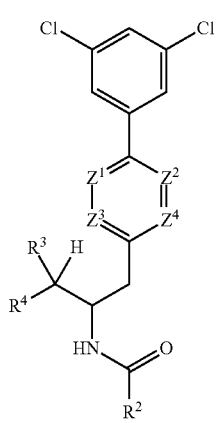

(II)

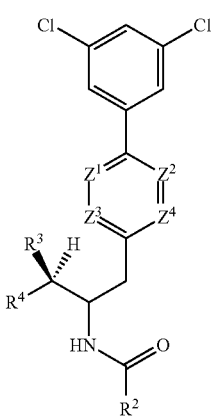

(III)

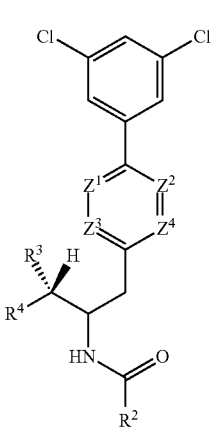

(IV)

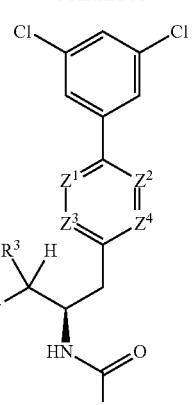

(V)

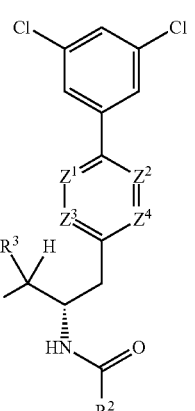

(VI)

wherein R⁴ is selected from

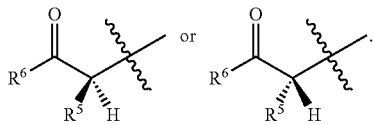

22. The method of claim 21, wherein the compound is enriched with respect to the shown stereochemistry in an amount that is >95% as compared to the amount of other stereoisomer impurities.

23. The method of claim 21, wherein the compound is enriched with respect to the shown stereochemistry in an amount that is >98% as compared to the amount of other stereoisomer impurities.

24. The method of claim 1, wherein the compound of Formula (I) is selected from the group consisting of:

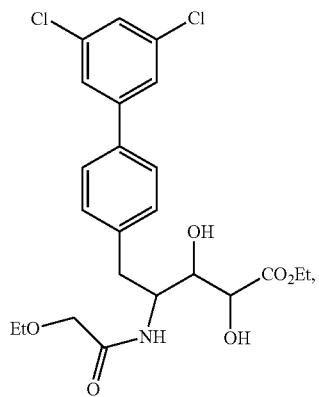

99
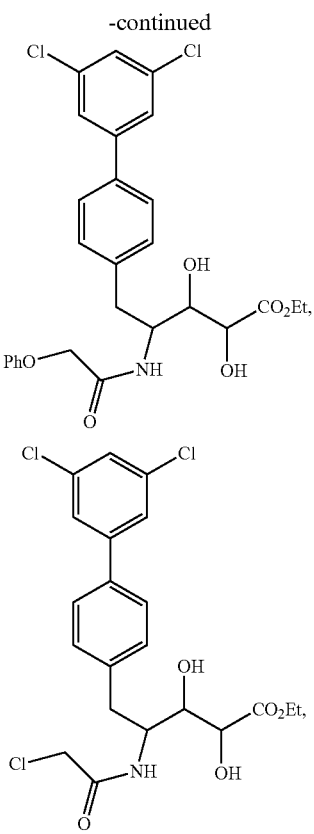
100
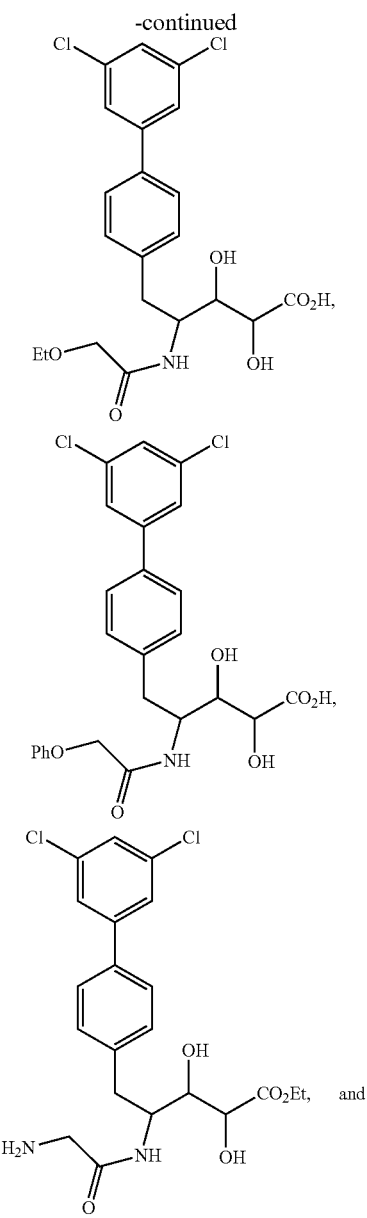
or pharmaceutically acceptable salts thereof.

25. The method of claim 24, wherein the compound is selected from the group consisting of:
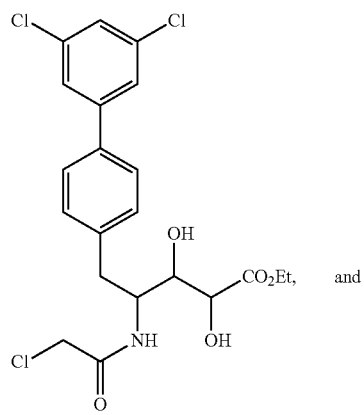
and
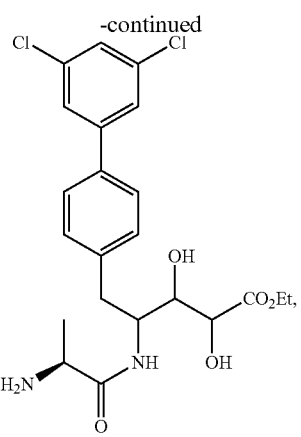
and or pharmaceutically acceptable salts thereof.
26. The method of claim 1, wherein the compound inhibits Cdc34 ubiquitin-conjugating enzyme.
27. The method of claim 26, wherein said Cdc34 is human Cdc34 (hCdc34).
* * * * *

UNITED STATES PATENT AND TRADEMARK OFFICE
CERTIFICATE OF CORRECTION

PATENT NO. : 9,546,131 B2
APPLICATION NO. : 14/447473
DATED : January 17, 2017
INVENTOR(S) : Kyle W. H. Chan It is certified that error appears in the above-identified patent and that said Letters Patent is hereby corrected as shown below:

On the Title Page

Item (72), (Inventors) at Line 2, Change "Sante" for Frank Mercurio to --Santa--.

In the Specification

In Column 3 at Line 5, Change "NFkB" to --NFκB--.

In Column 3 at Line 6, Change "NFkB" to --NFκB--.

In Column 4 at Line 1, Change "Butylithium" to --butyllithium--.

In Column 8 at Line 64, Change "p-toluensulfonic," to --p-toluenesulfonic,--.

In Column 9 at Line 20, Change "p-toluensulfonic" to --p-toluenesulfonic--.

In Column 17 at Lines 25-40, After " 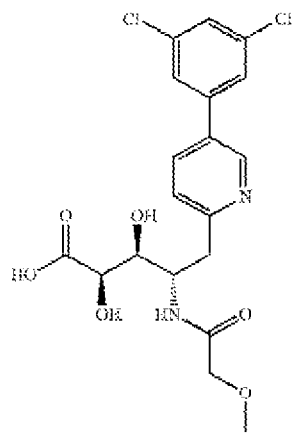 " insert --,--.

Signed and Sealed this
Fifteenth Day of August, 2017

Joseph Matal
*Performing the Functions and Duties of the
Under Secretary of Commerce for Intellectual Property and
Director of the United States Patent and Trademark Office*

In Column 18 at Lines 1-20 (approx.),
Change " 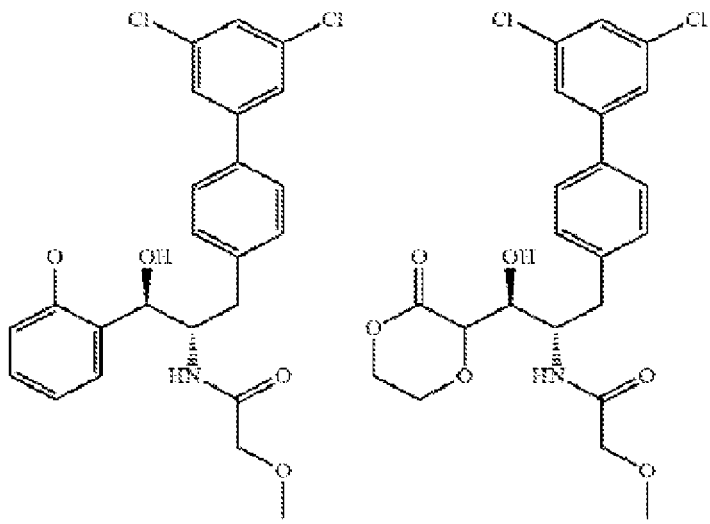 " to
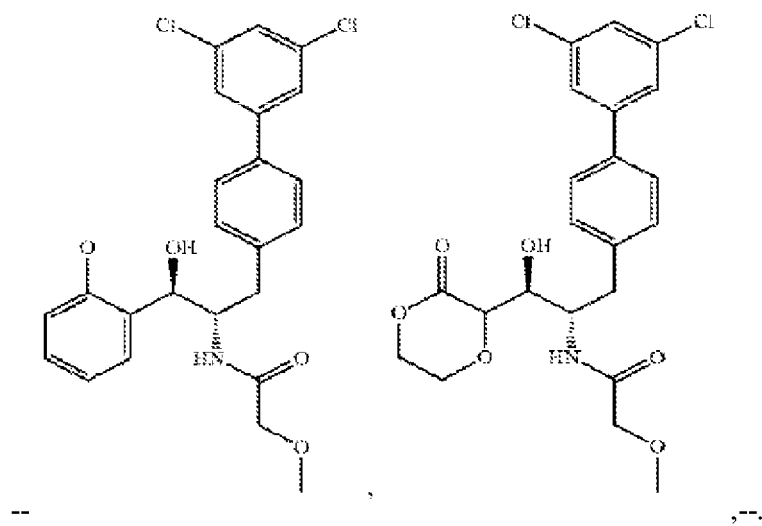
,--.
In Column 32 at Line 12 (approx.), Change "[(R1R)-3-methyl-1-(1-{(2S)" to --([(1R)-3-methyl-1-({(2S)--.
In Column 34 at Line 62 (approx.), Change "Formula (B)," to --Formula (B$^I$),--.
In Column 35 at Lines 59-60 (approx.), Change " $R^3 = H$ $R^5 = H$ " to -- $R^3 = OH$ $R^5 = OH$ --.

CERTIFICATE OF CORRECTION (continued)
U.S. Pat. No. 9,546,131 B2

In Column 36 at Lines 20-36 (approx.),

Change " 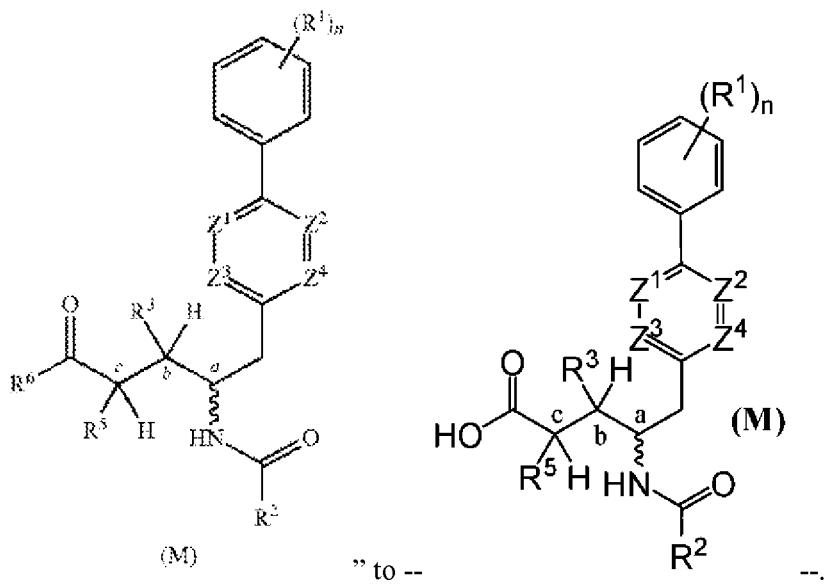 " to -- --.

In Column 39 at Line 9 (approx.), Above "b) SmI₂, DMAE; then" insert --or--.

In Column 40 at Line 12 (approx.), Change "(O)" to --(Q)--.

In Column 40 at Line 22 (approx.), Change "(O)" to --(Q)--.

In Column 40 at Line 24 (approx.), Change "(O)" to --(Q)--.

In Column 40 at Line 28 (approx.), Change "(O)" to --(Q)--.

In Column 50 at Line 18, Change "tetrabuylammonium" to --tetrabutylammonium--.

In Column 50 at Line 30, Above " 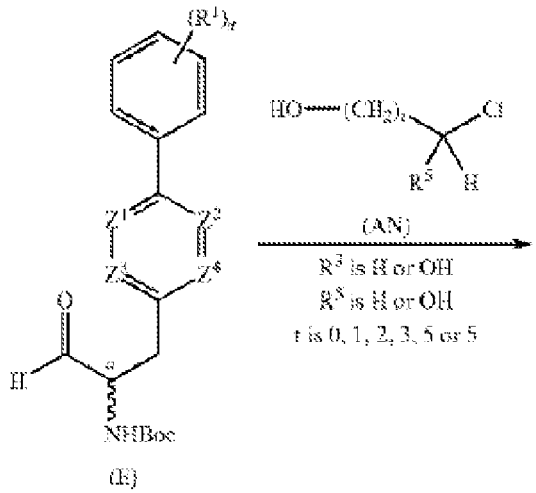 " insert --<u>Scheme 8</u>--.

In Column 50 at Line 42 (approx.), Change "5 or 5" to --4 or 5--.

CERTIFICATE OF CORRECTION (continued)
U.S. Pat. No. 9,546,131 B2

In Column 59 at Line 35, Change "al," to --al.,--.

In Column 59 at Line 37, Change "Weel" to --Wee1--.

In Column 59 at Line 57, Change "Ritonovir" to --Ritonavir--.

In Column 66 at Line 51 (approx.), Change "Lignd," to --Ligand,--.

In Column 73 at Line 1, After "ClCH$_2$COOH" insert --,--.

In Column 82 at Line 32 (approx.), Change "(1-1)" to --(I-1)--.

In Column 82 at Line 45, Change "1-2" to --I-2--.

In Column 94 at Line 65, Change "MDA-MD-468" to --MDA-MB-468--.

In Column 95 at Line 1, Change "NFkB" to --NFκB--.

In Column 95 at Line 2, Change "NFkB" to --NFκB--.

In Column 95 at Line 6 (approx.), Change "468NFkB" to --468-NFκB--.

In Column 95 at Line 8 (approx.), Change "NF-kB" to --NFκB--.

In Column 95 at Line 14 (approx.), Change "NFkB/" to --NFκB/--.

In Column 95 at Line 18 (approx.), Change "NFkB" to --NFκB--.

In the Claims

In Column 95 at Line 42, In Claim 1, change "non-hod kin's 1 mphoma," to --non-hodgkin's lymphoma,--.

In Column 96 at Line 24 (approx.), In Claim 1, after "is" delete "hydrogen".

In Column 102 at Line 18 (approx.), In Claim 25, after "and" delete "or".